United States Patent
Larsen

(10) Patent No.: US 11,096,407 B2
(45) Date of Patent: Aug. 24, 2021

(54) REDUCED NEGATIVE ZETA POTENTIAL SANITIZATION METHOD AND SYSTEM

(71) Applicant: CESCO SOLUTIONS, INC., Bellingham, WA (US)

(72) Inventor: Karl W. Larsen, Bellingham, WA (US)

(73) Assignee: CESCO SOLUTIONS, INC., Bellingham, WA (US)

( * ) Notice: Subject to any disclaimer, the term of this patent is extended or adjusted under 35 U.S.C. 154(b) by 190 days.

(21) Appl. No.: 16/111,095

(22) Filed: Aug. 23, 2018

(65) Prior Publication Data

US 2019/0059420 A1    Feb. 28, 2019

Related U.S. Application Data

(60) Provisional application No. 62/550,163, filed on Aug. 25, 2017.

(51) Int. Cl.
*A23L 3/358* (2006.01)
*A23B 4/24* (2006.01)
(Continued)

(52) U.S. Cl.
CPC .............. *A23L 3/358* (2013.01); *A23B 4/24* (2013.01); *A23B 5/18* (2013.01); *A23B 7/157* (2013.01);
(Continued)

(58) Field of Classification Search
CPC .. A23B 5/18; A23B 4/24; A23B 7/157; A61L 2/18; A61L 2/035; A61L 2202/11;
(Continued)

(56) References Cited

U.S. PATENT DOCUMENTS 7,547,413 B2    6/2009  Bauer
7,906,025 B2    3/2011  Bauer
(Continued)

OTHER PUBLICATIONS

Wilder (Thesis (2016) available online May 15, 2015—Evaluation of a novel commercial ground beef production system using a chlorinated nanobubble antimicrobial technology to control Shiga toxin-producing *Escherichia coli* and *Salmonella* spp. surrogates) (Year: 2016).*

(Continued)

*Primary Examiner* — Subbalakshmi Prakash
(74) *Attorney, Agent, or Firm* — FisherBroyles, LLP; Susan M. Oiler

(57) ABSTRACT

Methods and systems for sanitization of liquid solutions and food products are provided. In some embodiments, methods are provided for treating a food product or food product preparation or packaging surface to reduce microbial content, comprising contacting the food product or food product preparation or packaging surface with a chlorinated nanobubble solution comprising electrolyzed water. In some embodiments, methods are provided for reducing the growth of bacteria and reversing the growth of biofilm in a water system, comprising chlorinating source water and passing the chlorinated source water through a low zeta potential crystal generator. In some embodiments, methods are provided for purifying water, comprising chlorinating the water and passing the chlorinated water through a low zeta potential crystal generator.

11 Claims, 27 Drawing Sheets

(51) Int. Cl.
  *A23B 5/18*    (2006.01)
  *A23B 7/157*   (2006.01)
  *A61L 2/18*    (2006.01)
  *C02F 1/467*   (2006.01)
  *A61L 2/03*    (2006.01)
  *C02F 1/00*    (2006.01)

(52) U.S. Cl.
  CPC .............. *A61L 2/035* (2013.01); *A61L 2/18* (2013.01); *C02F 1/005* (2013.01); *C02F 1/4674* (2013.01); *A23V 2002/00* (2013.01); *A61L 2202/11* (2013.01); *A61L 2202/23* (2013.01); *C02F 2303/04* (2013.01); *C02F 2303/20* (2013.01); *C02F 2303/26* (2013.01)

(58) Field of Classification Search
  CPC .... A61L 2202/23; C02F 1/005; C02F 1/4674; C02F 2303/26; C02F 2303/20; C02F 2303/04; A23L 3/358; A23V 2002/00
  See application file for complete search history.

(56) References Cited

U.S. PATENT DOCUMENTS

| | | | |
|---|---|---|---|
| 8,454,837 B2 | 6/2013 | Bauer | |
| 8,826,714 B2 | 9/2014 | Bauer et al. | |
| 9,167,843 B2 | 10/2015 | Garwood | |
| 2016/0029602 A1* | 2/2016 | Nakamoto | C02F 1/4618 134/56 R |
| 2016/0236158 A1 | 8/2016 | Bauer | |
| 2018/0134583 A1 | 5/2018 | Bauer | |

OTHER PUBLICATIONS

Najjar, M. B., & Meng, J. (2009). Risk Assessment of Disinfection Byproducts in Poultry Chilled in Chlorinated Water. Joint Institute for Food Safety and Nutrition and Department of Nutrition and Food Science.

Vizzier-Thaxton, Y., et al. (2010). Generation and detection of trihalomethanes in chicken tissue from chlorinated chill water. The Journal of Applied Poultry Research, 19(2), 169-173.

Laufer, A. S., et al. (2015). Outbreaks of *Salmonella* infections attributed to beef—United States, 1973-2011. Epidemiology and Infection, 143(9), 2003-2013.

Park, H., et al. (2004). Effects of chlorine and pH on efficacy of electrolyzed water for inactivating *Escherichia coli* O157:H7 and Listeria monocytogenes. International Journal of Food Microbiology, 91(1), 13-18.

Stopforth, J. D., et al. (2008). Effect of Acidified Sodium Chlorite, Chlorine, and Acidic Electrolyzed water on *Escherichia coli* O157:H7, *Salmonella*, and Listeria monocytogenes Inoculated on Leafy Greens. Journal of Food Protection, 71(3), 625-628.

Guentzel, J. L., et al. (2008). Reduction of bacteria on spinach, lettuce, and surfaces in food service areas using neutral electrolyzed oxidizing water. Food Microbiology, 25(1), 36-41.

Niebuhr, S. E., et al. (2008). Evaluation of nonpathogenic surrogate bacteria as process validation indicators for *Salmonella enterica* for selected antimicrobial treatmeants, cold storage, and fermentation in meat. Journal of Food Protection, 71(4), 714-718.

Soli, K. W. et al. (2010). Decontamination of fresh produce by the use of slightly acidic hypochlorous water following pretreatment with sucrose fatty acid ester under microbubble generation. Food Control, 21(9), 1240-1244.

Agarwal, A. et al. (2011). Principle and applications of microbubble and nanobubble technology for water treatment. Chemosphere, 84(9), 1175-1180.

Dos Santos, M. S., et al. (2011). Determination of THMs in soft drink by solid-phase microextraction and gas chromatography. Food Chemistry, 127(1), 290-295.

Yang, Y., et al. (2012). Enhanced Chlorine Efficacy against Bacterial Pathogens in Wash Solution with High Organic Loads: Enhanced Chlorine Efficacy against Pathogens. Journal of Food Processing and Preservation, 36(6), 560-566.

Zhou, B., et al. (2015). Inactivation dynamics of *Salmonella enterica*, Listeria monocytogenes, and *Escherichia coli* O157:H7 in wash water during simulated chlorine depletion and replenishment processes. Food Microbiology, 50,88-96.

Laster, B. A., et al. (2012). Efficacy of trimming chilled beef during fabrication to control *Escherichia coli* O157:H7 surrogates on subsequent subprimals. Meat Science, 90(2), 420-425.

Waters, B. W., & Hung, Y.-C. (2014). The effect of organic loads on stability of various chlorine-based sanitisers. International Journal of Food Science & Technology, 49(3), 867-875.

Sohaib, M. et al. (2016) Postharvest intervention technologies for safety enhancement of meat and meat based products; a critical review. Journal of Food Science and Technology, 53(1), 19-30, 2016.

Bauer (2016) Nanobubbles from www.nanobubbles.com, Retrieved Jul. 10, 2019.

*Salmonella*, retrieved Jul. 10, 2019, from www.cdc.gov/Salmonella/.

CDC—Disinfection & Sterilization Guideline:Disinfection—HICPAC. Retrieved Jul. 10, 2019, from http://www.cdc.gov/infectioncontrol/guidelines/disinfection/index.html.

Particle Sciences. (2012). Zeta Potential (ZP): An Overview—Particle Sciences, Drug Development (Technical Brief No. vol. 2). Bethlehem, PA, retrieved from www.particlesciences.com/news/technical-briefs/2012/overview-of-zeta-potential.html; Tsuge, H. (Ed.). (2014).

* cited by examiner

|  |  | Vortex | | | Manifold | | | Flotation Tank | | | Post-Particle Filter | | |
|---|---|---|---|---|---|---|---|---|---|---|---|---|---|
|  |  | A | B | C | A | B | C | A | B | C | A | B | C |
| Day 1 | FAC | 1.19 | 3.3 | 4.0 | 0.18 | 0.06 | 0.49 | 0.20 | 0.03 | 0.11 | 0.04 | 0.06 | 0.11 |
|  | Total Cl | 9.0 | 15.0 | 10.5 | 6.4 | 6.3 | 4.6 | 6.1 | 4.2 | 5.9 | 5.9 | 5.6 | 5.9 |
|  | pH | 5.15 | 4.69 | 4.93 | 5.03 | 4.8 | 5.03 | 5.08 | 5.12 | 4.72 | 5.15 | 5.20 | 4.90 |
|  | ORP | 826 | 836 | 878 | 843 | 618 | 915 | 783 | 570 | 841 | 515 | 423 | 537 |
|  | CFU/mL | - | - | - | 0.014 | - | - | - | - | - | - | - | - |
| Day 2 | FAC | 2.5 | 2.3 | 3.3 | 0.04 | 0.16 | 0.62 | 0.04 | 0.02 | 0.49 | 0.48 | 0.06 | 0.05 |
|  | Total Cl | 9.8 | 12.2 | 12.3 | 6.3 | 7.8 | 10.0 | 5.4 | 5.5 | 8.5 | 5.6 | 6.6 | 9.1 |
|  | pH | 5.38 | 5.42 | 5.51 | 5.11 | 5.15 | 5.49 | 4.91 | 5.08 | 4.04 | 5.33 | 5.39 | 5.18 |
|  | ORP | 833 | 828 | 811 | 761 | 640 | 903 | 735 | 592 | 920 | 441 | 399 | 538 |
|  | CFU/mL | - | - | - | 0.092 | 0.026 | - | - | - | - | - | - | - |
| Day 3 | FAC | 4.1 | 4.2 | 3.4 | 0.04 | 0.04 | 2.4 | 0.07 | 0.16 | 0.31 | 0.06 | 0.05 | 0.32 |
|  | Total Cl | 10.2 | 14.6 | 13.7 | 6.7 | 7.9 | 11.0 | 7.7 | 7.2 | 9.5 | 7.0 | 6.4 | 9.3 |
|  | pH | 5.49 | 5.49 | 5.83 | 5.15 | 5.18 | 5.96 | 4.84 | 4.94 | 4.92 | 5.38 | 5.39 | 5.64 |
|  | ORP | 861 | 870 | 800 | 774 | 671 | 870 | 785 | 629 | 875 | 496 | 399 | 538 |
|  | CFU/mL | - | - | - | 0.002 | 0.051 | 0.004 | - | - | - | 0.002 | - | - |
| Day 4 | FAC | 3.9 | 3.7 | 3.6 | 1.51 | 0.06 | 2.9 | 0.12 | 0.04 | 0.82 | 0.06 | 0.84 | 0.89 |
|  | Total Cl | 13.7 | 11.2 | 12.3 | 10.1 | 7.5 | 9.5 | 8.1 | 8.5 | 7.4 | 9.3 | 8.3 | 7.0 |
|  | pH | 5.47 | 5.46 | 5.68 | 5.21 | 5.19 | 5.83 | 4.76 | 4.9 | 4.57 | 5.28 | 5.33 | 5.39 |
|  | ORP | 873 | 867 | 817 | 831 | 747 | 885 | 827 | 641 | 904 | 468 | 376 | 633 |
|  | CFU/mL | - | - | - | - | - | - | - | - | - | - | - | - |
| Day 5 | FAC | 3.0 | 4.5 | 4.2 | 0.07 | 0.16 | 2.3 | 0.18 | 0.21 | 1.17 | 0.89 | 0.04 | 1.12 |
|  | Total Cl | 9.9 | 17.9 | 10.0 | 5.9 | 8.4 | 7.8 | 5.2 | 4.9 | 6.9 | 5.3 | 5.6 | 6.6 |
|  | pH | 5.52 | 5.54 | 5.49 | 5.29 | 5.31 | 5.56 | 4.88 | 4.97 | 4.58 | 5.37 | 5.41 | 5.25 |
|  | ORP | 852 | 866 | 848 | 751 | 725 | 910 | 763 | 676 | 927 | 433 | 388 | 674 |
|  | CFU/mL | - | - | - | - | - | - | 0.006 | - | - | 0.005 | - | - |
| Day 6 | FAC | 5.3 | 3.3 | 2.7 | 0.07 | 0.11 | 0.66 | 0.05 | 0.02 | 0.2 | 0.19 | 0.03 | 0.18 |
|  | Total Cl | 12.4 | 12.9 | 12.9 | 5.6 | 6.8 | 9.5 | 5.7 | 6.2 | 9.9 | 4.9 | 6.1 | 8.2 |
|  | pH | 5.58 | 5.69 | 6.3 | 5.37 | 5.47 | 6.41 | 4.95 | 5.13 | 5.4 | 5.37 | 5.51 | 6.00 |
|  | ORP | 846 | 837 | 743 | 793 | 731 | 830 | 786 | 688 | 815 | 469 | 400 | 416 |
|  | CFU/mL | - | - | - | - | - | - | - | - | - | - | - | - |

FIG. 26

A — Water collected after inoculated meat at beginning of production run. B — Water collected within 10 minutes of inoculated meat during middle of production run. C — Water collected after 4-hr sanitation; Average pH 5.27±0.38; Average ORP 717±164 mV; Average FAC: Vortex 3.47±0.91 ppm, Manifold 0.66±0.92 ppm, Flotation Tank 0.24±0.30 ppm, Post-Particle Filter 0.26±0.33 ppm.

|  |  | Vortex | | | Manifold | | | Flotation Tank | | | Post-Particle Filter | | |
| --- | --- | --- | --- | --- | --- | --- | --- | --- | --- | --- | --- | --- | --- |
|  |  | A | B* | C | A* | B* | C | A | B | C | A* | B | C |
| Rep 1 | FAC | 4.3 | 2.1 | 4.3 | 0.67 | 0.68 | 3.5 | 1.28 | 0.62 | 0.44 | 1.19 | 0.50 | 0.45 |
|  | Total Cl | 8.2 | 11.5 | 11.4 | 4.7 | 8.2 | 9.6 | 5.9 | 9.5 | 8.5 | 5.1 | 9.5 | 8.7 |
|  | pH | 5.13 | 5.35 | 5.24 | 4.96 | 5.15 | 5.12 | 5.08 | 5.18 | 5.01 | 5.04 | 5.20 | 5.20 |
|  | ORP | 796 | 716 | 703 | 914 | 763 | 890 | 908 | 888 | 828 | 558 | 484 | 376 |
|  |  | D | E | F | D | E | F | D | E | F | D | E | F |
|  | FAC | 4.3 | 2.9 | 2.2 | 0.39 | 0.2 | 3.3 | 3.8 | 0.76 | 3 | 4.2 | 0.6 | 3.4 |
|  | Total Cl | 10.7 | 14.2 | 7.6 | 7.8 | 13.5 | 9.8 | 8.7 | 13.7 | 9.3 | 9.7 | 11.0 | 11.0 |
|  | pH | 5.48 | 5.64 | 5.45 | 5.24 | 5.34 | 5.19 | 5.28 | 4.95 | 4.86 | 5.45 | 5.57 | 5.42 |
|  | ORP | 724 | 687 | 669 | 900 | 759 | 882 | 865 | 846 | 915 | 505 | 357 | 518 |
| Rep 2 |  | A | B | C | A* | B* | C | A | B | C | A | B* | C |
|  | FAC | 2.7 | 2.7 | 2.8 | 0.88 | 0.18 | 2.7 | 0.69 | 0.75 | 2.3 | 0.46 | 0.70 | 2.2 |
|  | Total Cl | 10.5 | 9.5 | 10.7 | 9.3 | 9.2 | 9.5 | 9.7 | 11.0 | 9.6 | 8.1 | 11.5 | 9.4 |
|  | pH | 5.53 | 5.59 | 5.41 | 5.27 | 5.24 | 4.95 | 5.34 | 5.23 | 4.98 | 5.48 | 5.54 | 5.42 |
|  | ORP | 705 | 710 | 667 | 779 | 856 | 904 | 803 | 845 | 902 | 556 | 491 | 518 |
|  |  | D | E | F | D | E | F | D | E | F | D | E | F |
|  | FAC | 2.2 | 3.4 | 4.1 | 0.15 | 0.29 | 3.5 | 1.16 | 2.5 | 3.3 | 2.2 | 1.13 | 1.94 |
|  | Total Cl | 9.8 | 13.0 | 9.6 | 7.5 | 7.7 | 8.5 | 9.2 | 13.0 | 10.0 | 7.4 | 13.5 | 8.8 |
|  | pH | 5.48 | 5.50 | 5.24 | 5.13 | 5.16 | 4.59 | 5.30 | 5.21 | 4.94 | 5.47 | 5.49 | 5.26 |
|  | ORP | 701 | 701 | 686 | 827 | 720 | 874 | 850 | 877 | 925 | 491 | 518 | 585 |
| Rep 3 |  | A | B | C | A* | B* | C | A* | B | C | A | B | C |
|  | FAC | 2.8 | 2.2 | 4.3 | 0.24 | 0.14 | 3.2 | 0.55 | 0.26 | 2.4 | 0.58 | 0.21 | 2.4 |
|  | Total Cl | 10.0 | 14.5 | 12.9 | 7.8 | 11.3 | 10.8 | 9.9 | 14.3 | 11.6 | 10.0 | 11.7 | 10.9 |
|  | pH | 5.39 | 5.51 | 5.40 | 4.94 | 5.02 | 4.56 | 5.29 | 5.34 | 5.00 | 5.38 | 5.49 | 5.40 |
|  | ORP | 694 | 670 | 681 | 801 | 785 | 817 | 831 | 791 | 912 | 388 | 319 | 566 |
|  |  | D | E | F | D | E | F | D | E | F | D | E | F |
|  | FAC | 5.3 | 3.4 | 3.5 | 0.22 | 0.1 | 3.3 | 4.4 | 0.56 | 2.5 | 3.3 | 0.52 | 2.2 |
|  | Total Cl | 13.5 | 17.8 | 12.4 | 9.7 | 9.7 | 11.9 | 11.5 | 13.0 | 12.3 | 12.2 | 12.8 | 10.9 |
|  | pH | 5.50 | 5.75 | 5.55 | 4.98 | 5.08 | 4.95 | 5.32 | 5.40 | 5.17 | 5.49 | 5.72 | 5.31 |
|  | ORP | 727 | 661 | 715 | 753 | 699 | 797 | 879 | 831 | 899 | 618 | 413 | 513 |

* Positive samples following Whatman filter enrichment; Samples A-C collected on Day 1 (inoculation days), D-F collected on Day 2 (24-hr pick-up days); A — Water collected after inoculated meat at beginning of production run, B — Water collected within 10 minutes of inoculated meat during middle of production run, C — Water collected after 4-hr sanitation, D — Water collected within 10 minutes of pick-up meat at beginning of production run, E — Water collected within 10 minutes of pick-up meat at end of production run, F — Water collected after 4-hr sanitation; Average pH 5.26±0.24; Average ORP 715±161 mV; Average FAC: Vortex 3.31±0.92 ppm, Manifold 1.31±1.39 ppm, Flotation Tank 1.74±1.26 ppm, Post-Particle Filter 1.62±1.23 ppm.

FIG. 27

REDUCED NEGATIVE ZETA POTENTIAL SANITIZATION METHOD AND SYSTEM

CROSS-REFERENCE TO RELATED APPLICATIONS

This application claims the benefit of U.S. Provisional Patent Application No. 62/550,163 filed Aug. 25, 2017, which is incorporated herein by reference in its entirety.

TECHNICAL FIELD

The presently disclosed subject matter relates generally to methods and systems for sanitization of liquid solutions and food products, and more particularly to the use of chlorinated nanobubble antimicrobial compositions and methods and systems for their use.

BACKGROUND

Chlorine is widely used as a sanitizer for fresh produce, meat products, and water supplies. In the case of produce, fresh fruits and vegetables can get contaminated with pathogenic bacteria in the fields through dirt, soil, manure, insects, animals and irrigation water; whereas contamination can occur in packaging facilities through improper washing, during handling and packaging, through cross contamination, and due to biofilm build-up on processing equipment. Washing with chlorinated water (50-200 ppm chlorine) is widely used to sanitize whole fruits and vegetables as well as fresh-cut produce on a commercial scale. The recommended pH range of the chlorine solution for the produce wash is 6.5 to 7.5 (McGlynn (2016) Guidelines for the use of chlorine bleach as a sanitizer in food processing operations (FAPC-116). Facts Sheets, Food and Agricultural Products Center (FAPC), Oklahoma State University, Stillwater, Okla.). However, its effectiveness is limited in reducing the population of microorganisms (less than 2 log colony forming unit, hereinafter CFU) on fruits and vegetables.

In meat processing, e.g., beef and poultry processing, microbiological control is of vital importance. By the nature of the processing, there are numerous opportunities for the meat to be exposed to various pathogens in the form of mobile bacteria such as, e.g., *Escherichia coli, Salmonella enteritidis, Salmonella typhimurim, Campylobacter* spp., and in the form of biofilms such as, e.g., *Listeria monocytogenes, Pseudomonas fluorescens* spp., *Enterococcus faecium*, and *Staphylococcus aureus*. Although chlorination has been used for over a century as a cheap and convenient treatment for control of microbial contamination, chlorine-based microbiocides for meat have serious shortcomings. According to a European Consumers' Organization study conducted in 2010, 82 percent of United States chickens that had been treated in chlorine baths still contained harmful pathogens. Furthermore, chlorination is malodorous and, in many cases, can exert an unpalatable bleaching effect upon meat.

Also of serious concern is the safety and potability of certain water supplies using source liquid from wells, springs, water pumps, septic tanks, reservoirs, water treatment devices, water lines, and the like. Such water supplies are susceptible to contamination by harmful microorganisms such as bacteria and viruses, particularly those that cause gastrointestinal disorders and illnesses. Unfortunately, similar problems exist with respect to chlorination of water supplies as for produce and meat processing in terms of efficacy and palatability. Alternatives to chlorination such as boiling, distillation, ultraviolet light, and ozonation are expensive, lengthy, and/or impractical for large volumes of water.

Accordingly, there is a need for improved methods methods and systems for sanitization of liquid solutions and food products.

SUMMARY OF THE INVENTION

To address the foregoing problems, in whole or in part, and/or other problems that may have been observed by persons skilled in the art, the present disclosure provides compositions and methods as described by way of example as set forth below.

In some embodiments, the presently disclosed subject matter provides a method of treating a food product to reduce microbial content, comprising contacting the food product with a chlorinated nanobubble solution, wherein the chlorinated nanobubble solution comprises electrolyzed water, and wherein the microbial content of the food product is reduced by at least about 0.3 log CFU/g. In some embodiments, the electrolyzed water has an enhanced concentration of low zeta potential crystal and is generated by passing source water through a low zeta potential crystal generator and changing the crystalline structure of minerals in the source water. In another embodiment, the zeta potential of mineral crystals in the electrolyzed water after passage through the low zeta potential crystal generator is at least 25% less than the zeta potential of mineral particles in the source water. In another embodiment, the zeta potential of mineral crystals in the electrolyzed water after passage through the low zeta potential crystal generator is at least 50% less than the zeta potential of mineral particles in the source water.

In other embodiments within the method of treating a food product to reduce microbial content, the chlorinated nanobubble solution comprises nanobubbles having a diameter of less than 200 nm. In other embodiments, the chlorinated nanobubble solution comprises nanobubbles having a diameter of between 50 nm and 100 nm. In other embodiments, the chlorinated nanobubble solution comprises nanobubbles having a diameter of between 10 nm and 50 nm. In other embodiments, the chlorinated nanobubble solution comprises free available chlorine in an amount of less than 2,000 ppm. In other embodiments, the chlorinated nanobubble solution comprises free available chlorine in an amount of less than or equal to 300 ppm. In other embodiments, the chlorinated nanobubble solution comprises free available chlorine in an amount of less than or equal to 50 ppm. In other embodiments, the chlorinated nanobubble solution comprises free available chlorine in an amount of between 100 ppm and 300 ppm. In other embodiments, the chlorinated nanobubble solution comprises free available chlorine in an amount of between 50 ppm and 300 ppm. In other embodiments, the chlorinated nanobubble solution comprises free available chlorine in an amount of between 0.5 ppm and 50 ppm. In other embodiments, the chlorinated nanobubble solution has a pH of less than 7. In other embodiments, the chlorinated nanobubble solution has a pH of between 5 and 7. In other embodiments, the chlorinated nanobubble solution has a pH of 5.

In other embodiments within the method of treating a food product to reduce microbial content, the food product is selected from the group consisting of meat, vegetables, fruit, and eggs in their shell. In other embodiments, the meat is selected from the group consisting of beef, poultry, and pork.

In some embodiments, the presently disclosed subject matter provides a method of treating a food product preparation or packaging surface to reduce microbial content, comprising contacting the food product preparation or packaging surface with a chlorinated nanobubble solution, wherein the chlorinated nanobubble solution comprises electrolyzed water, and wherein the microbial content of the food product is reduced by at least about 0.3 log CFU/g. In some embodiments, the electrolyzed water has an enhanced concentration of low zeta potential crystal and is generated by passing source water through a low zeta potential crystal generator and changing the crystalline structure of minerals in the source water. In another embodiment, the zeta potential of mineral crystals in the electrolyzed water after passage through the low zeta potential crystal generator is at least 25% less than the zeta potential of mineral particles in the source water. In another embodiment, the zeta potential of mineral crystals in the electrolyzed water after passage through the low zeta potential crystal generator is at least 50% less than the zeta potential of mineral particles in the source water.

In other embodiments within the method of treating a food product preparation or packaging surface to reduce microbial content, the chlorinated nanobubble solution comprises nanobubbles having a diameter of less than 200 nm. In other embodiments, the chlorinated nanobubble solution comprises nanobubbles having a diameter of between 50 nm and 100 nm. In other embodiments, the chlorinated nanobubble solution comprises nanobubbles having a diameter of between 10 nm and 50 nm. In other embodiments, the chlorinated nanobubble solution comprises free available chlorine in an amount of less than 2,000 ppm. In other embodiments, the chlorinated nanobubble solution comprises free available chlorine in an amount of less than or equal to 300 ppm. In other embodiments, the chlorinated nanobubble solution comprises free available chlorine in an amount of less than or equal to 50 ppm. In other embodiments, the chlorinated nanobubble solution comprises free available chlorine in an amount of between 100 ppm and 300 ppm. In other embodiments, the chlorinated nanobubble solution comprises free available chlorine in an amount of between 50 ppm and 300 ppm. In other embodiments, the chlorinated nanobubble solution comprises free available chlorine in an amount of between 0.5 ppm and 50 ppm. In other embodiments, the chlorinated nanobubble solution has a pH of less than 7. In other embodiments, the chlorinated nanobubble solution has a pH of between 5 and 7. In other embodiments, the chlorinated nanobubble solution has a pH of 5.

In other embodiments within the method of treating a food product preparation or packaging surface to reduce microbial content, the food product preparation or packaging surface is used to prepare or package a food product selected from the group consisting of meat, vegetables, fruit, and eggs in their shell. In other embodiments, the meat is selected from the group consisting of beef, poultry, and pork.

In some embodiments, the presently disclosed subject matter provides a method of reducing the growth of bacteria and reversing the growth of biofilm in a water system, comprising chlorinating source water and passing the chlorinated source water through a low zeta potential crystal generator and changing the crystalline structure of minerals in the source water to produce treated chlorinated water having an enhanced concentration of low zeta potential crystal, and wherein the microbial content of the treated chlorinated water is reduced by at least about 0.3 log CFU/mL compared to the source water.

In some embodiments of the method of reducing the growth of bacteria and reversing the growth of biofilm in a water system, the electrolyzed water has an enhanced concentration of low zeta potential crystal and is generated by passing source water through a low zeta potential crystal generator and changing the crystalline structure of minerals in the source water. In another embodiment, the zeta potential of mineral crystals in the electrolyzed water after passage through the low zeta potential crystal generator is at least 25% less than the zeta potential of mineral particles in the source water. In another embodiment, the zeta potential of mineral crystals in the electrolyzed water after passage through the low zeta potential crystal generator is at least 50% less than the zeta potential of mineral particles in the source water.

In other embodiments within the method of reducing the growth of bacteria and reversing the growth of biofilm in a water system, the chlorinated nanobubble solution comprises nanobubbles having a diameter of less than 200 nm. In other embodiments, the chlorinated nanobubble solution comprises nanobubbles having a diameter of between 50 nm and 100 nm. In other embodiments, the chlorinated nanobubble solution comprises nanobubbles having a diameter of between 10 nm and 50 nm. In other embodiments, the chlorinated nanobubble solution comprises free available chlorine in an amount of less than 2,000 ppm. In other embodiments, the chlorinated nanobubble solution comprises free available chlorine in an amount of less than or equal to 300 ppm. In other embodiments, the chlorinated nanobubble solution comprises free available chlorine in an amount of less than or equal to 50 ppm. In other embodiments, the chlorinated nanobubble solution comprises free available chlorine in an amount of between 100 ppm and 300 ppm. In other embodiments, the chlorinated nanobubble solution comprises free available chlorine in an amount of between 50 ppm and 300 ppm. In other embodiments, the chlorinated nanobubble solution comprises free available chlorine in an amount of between 0.5 ppm and 50 ppm. In other embodiments, the chlorinated nanobubble solution has a pH of less than 7. In other embodiments, the chlorinated nanobubble solution has a pH of between 5 and 7. In other embodiments, the chlorinated nanobubble solution has a pH of 5.

In some embodiments, the presently disclosed subject matter provides a method for purifying water, comprising chlorinating the water and passing the chlorinated water through a low zeta potential crystal generator and changing the crystalline structure of minerals in the chlorinated water to produce treated chlorinated water having an enhanced concentration of low zeta potential crystal, and wherein the treated chlorinated water has a particle concentration of less than 20,000,000 particles/mL. In some embodiments, the treated chlorinated water has a particle concentration of less than 15,000,000 particles/mL. In other embodiments, the treated chlorinated water has a particle concentration of less than 10,000,000 particles/mL.

In some embodiments of the method for purifying water, the electrolyzed water has an enhanced concentration of low zeta potential crystal and is generated by passing the water through a low zeta potential crystal generator and changing the crystalline structure of minerals in the water. In another embodiment, the zeta potential of mineral crystals in the electrolyzed water after passage through the low zeta potential crystal generator is at least 25% less than the zeta potential of mineral particles in the water. In another embodiment, the zeta potential of mineral crystals in the electrolyzed water after passage through the low zeta potential crystal generator is at least 50% less than the zeta potential of mineral particles in the water.

In other embodiments within the method for purifying water, the chlorinated nanobubble solution comprises nanobubbles having a diameter of less than 200 nm. In other embodiments, the chlorinated nanobubble solution comprises nanobubbles having a diameter of between 50 nm and 100 nm. In other embodiments, the chlorinated nanobubble solution comprises nanobubbles having a diameter of between 10 nm and 50 nm. In other embodiments, the chlorinated nanobubble solution comprises free available chlorine in an amount of less than 2,000 ppm. In other embodiments, the chlorinated nanobubble solution comprises free available chlorine in an amount of less than or equal to 300 ppm. In other embodiments, the chlorinated nanobubble solution comprises free available chlorine in an amount of less than or equal to 50 ppm. In other embodiments, the chlorinated nanobubble solution comprises free available chlorine in an amount of between 100 ppm and 300 ppm. In other embodiments, the chlorinated nanobubble solution comprises free available chlorine in an amount of between 50 ppm and 300 ppm. In other embodiments, the chlorinated nanobubble solution comprises free available chlorine in an amount of between 0.5 ppm and 50 ppm. In other embodiments, the chlorinated nanobubble solution has a pH of less than 7. In other embodiments, the chlorinated nanobubble solution has a pH of between 5 and 7. In other embodiments, the chlorinated nanobubble solution has a pH of 5.

Other compositions, methods, features, and advantages of the invention will be or will become apparent to one with skill in the art upon examination of the following figures and detailed description. It is intended that all such additional compositions, methods, features, and advantages be included within this description, be within the scope of the invention, and be protected by the accompanying claims.

BRIEF DESCRIPTION OF THE DRAWINGS

The features and advantages of the present invention will be more clearly understood from the following description taken in conjunction with the accompanying drawings, which are not necessarily drawn to scale, and wherein:

FIG. 26 shows a table with data on Free Available Chlorine (FAC), Total Chlorine, pH, ORP of Recirculating Water during the Preliminary Study.

FIG. 27 shows a table with data on Free Available Chlorine (FAC), Total Chlorine, pH, ORP of Recirculating Water during the Optimized Study.

DETAILED DESCRIPTION

Figure 1:
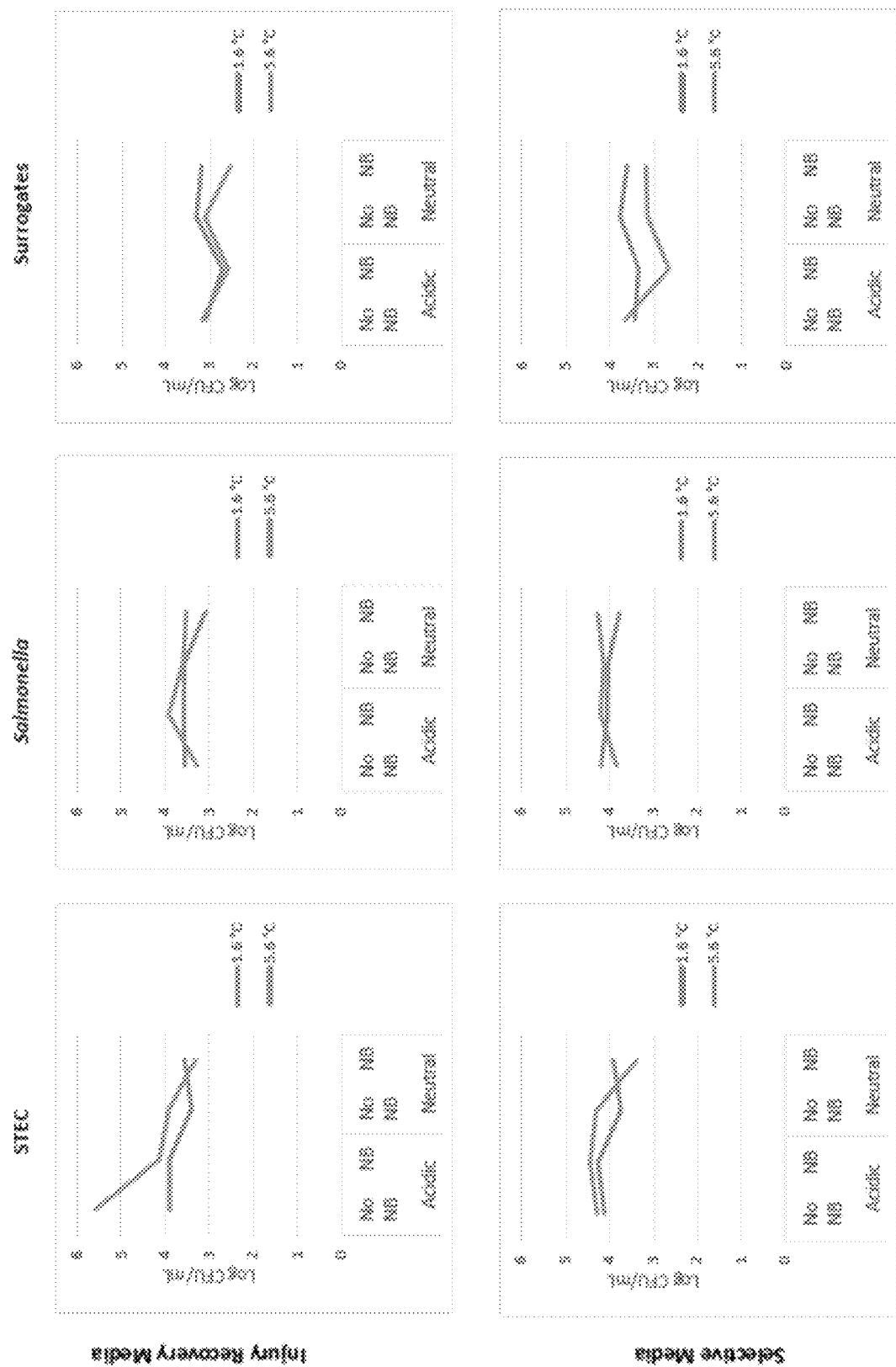
FIG. 1 shows a Profile Plot of 5-Way Interaction between Organism, Temperature, pH (Acidic or Neutral), Presence of Nanobubbles (NB), and Media Type. Least Square Means (Avg. Log CFU/mL) of Log CFU/mL reductions are reported for each combination.

The presently disclosed subject matter now will be described more fully hereinafter with reference to the accompanying Drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

General Definitions

In this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "coupled" and "linked" as used herein is defined as connected, although not necessarily directly and not necessarily mechanically. A device or structure that is "configured" in a certain way is configured in at least that way, but may also be configured in ways that are not listed. Also, the sequence of steps in a flow diagram or elements in the claims, even when preceded by a letter does not imply or require that sequence.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

As used herein, the phrase "food product" includes any food substance that might require irradiation and/or treatment with an antimicrobial agent or composition and that is edible with or without further preparation. Food products include meat (e.g. red meat and pork), seafood, poultry, fruits and vegetables, eggs, egg products, ready to eat food, wheat, seeds, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the phrase "plant product" includes any plant substance or plant-derived substance that might require irradiation and/or treatment with an antimicrobial agent or composition. Plant products include seeds, nuts, nut meats, cut flowers, plants or crops grown or stored in a greenhouse, house plants, and the like.

As used herein, a processed fruit or vegetable refers to a fruit or vegetable that has been cut, chopped, sliced, peeled, ground, milled, irradiated, frozen, cooked (e.g., blanched, pasteurized), or homogenized. As used herein a fruit or vegetable that has been washed, colored, waxed, hydrocooled, refrigerated, shelled, or had leaves, stems or husks removed is not processed.

As used herein, the phrase "meat product" refers to all forms of animal flesh, including muscle, fat, organs, skin, bones and body fluids and like components that form the animal. Animal flesh includes the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

For the purpose of this patent application, successful microbial reduction is achieved when the microbial populations are reduced by at least about 0.3-1 $\log_{10}$ Colony Forming Units per milliter for liquids (CFU/mL) or Colony Forming Units per gram for solids (CFU/g), for example, 0.3, 0.4, 0.5, 0.6, 0.7, 0.8, 0.9, or 1.0 CFU/mL for liquids CFU/g for solids. Any increased reduction in microbial population is an added benefit that provides higher levels of protection for processed food product.

Chlorination and Nanobubble Technology

Chlorine is applied as antimicrobial in a variety of forms for meat as directed by the USDA FSIS Safe and Suitable Ingredients list (USDA Food Safety and Inspection Service. (2016). *Safe and suitable ingredients used in the production of meat, poultry, and egg products*, No. FSIS Directive 7120.1 Rev. 37, Washington D.C.). Free chlorine, unbound available chlorine, is much more effective as an antimicrobial and therefore is the most important measurement of a sanitizer's antimicrobial activity. Factors contributing to stability of chlorine in solution include pH, low temperature, absence of catalysts, high alkalinity, and absence of organic material. In aqueous solution, free available chlorine (FAC) can be present as either hypochlorous acid (HOCl), at pH levels below 6.8, or hypochlorite (ClO$^-$): $Cl_2 + H_2O \rightarrow HOCl + H^+ + Cl^-$ (Block, S. S. (Ed.). (1991). *Disinfection, sterilization, and preservation* (4th ed). Philadelphia: Lea & Febiger). Although the exact mechanism by which FAC destroys microorganisms has not fully by elucidated, chlorine has been found to be effective against both Gram-positive and Gram-negative bacteria due its strong oxidative potential which disrupts bacterial cell walls resulting in cleavage of DNA (Centers for Disease Control (CDC). (2009). CDC—Disinfection & Sterilization Guideline:Disinfection—HICPAC. Retrieved Oct. 27, 2016, from www.cdc.gov/hicpac/Disinfection_Sterilization/6_0disinfection.html; Sohaib, M. et al. (2016) Postharvest intervention technologies for safety enhancement of meat and meat based products; a critical review. *Journal of Food Science and Technology*, 53(1), 19-30). Being uncharged, it is believed that hypochlorous acid effectively inactivates *E. coli* cells by acidifying the cytoplasm forcing the organism to dissociate from the inside and by disrupting metabolism by specifically inhibiting the transfer of needed fermentative and respiratory substrates, glucose and succinate, thus irreversibly abolishing ATP production even in the presence of nutrient sources (Block, S. S. (Ed.). (1991). *Disinfection, sterilization, and preservation* (4th ed). Philadelphia: Lea & Febiger; Barrette, W. C. et al. (1989). General mechanisms for the bacterial toxicity of hypochlorous acid: abolition of ATP production. *Biochemistry*, 28(23), 9172-9178; Najjar, M. B., & Meng, J. (2009). Risk Assessment of Disinfection Byproducts in Poultry Chilled in Chlorinated Water. Joint Institute for Food Safety and Nutrition and Department of Nutrition and Food Science). On the other hand, the bactericidal effect of the less germicidal hypochlorite is characterized by the penetration of germicidal ingredients into the cell and the subsequent formation of toxic complexes (N-chloro compounds) in the cell protoplasm (Block, S. S. (Ed.). (1991). *Disinfection, sterilization, and preservation* (4th ed). Philadelphia: Lea & Febiger).

pH has the greatest impact on the effectiveness of chlorine solutions (Block, S. S. (Ed.). (1991). *Disinfection, sterilization, and preservation* (4th ed). Philadelphia: Lea & Febiger). Hypochlorous acid is the primary disinfection agent, and at pH 5, HOCl constitutes 97% of total chlorine in solution (Park, H., et al. (2004). Effects of chlorine and pH on efficacy of electrolyzed water for inactivating *Escherichia coli* O157:H7 and *Listeria monocytogenes*. *International Journal of Food Microbiology*, 91(1), 13-18). The dissociation of hypochlorous acid (HOCl$\leftrightarrow$H$^+$+ClO$^-$) is highly dependent on pH; as pH increases, the disinfection capacity of chlorine decreases (Block, S. S. (Ed.). (1991). *Disinfection, sterilization, and preservation* (4th ed). Philadelphia: Lea & Febiger). The effectiveness of chlorine as a disinfectant is dependent on acidic pH (i.e., presence of hypochlorous acid), concentration of chlorine maintained in solution, and contact time (Najjar, M. B., & Meng, J. (2009). Risk Assessment of Disinfection Byproducts in Poultry Chilled in Chlorinated Water. Joint Institute for Food Safety and Nutrition and Department of Nutrition and Food Science; Zhou, B., et al. (2015). Inactivation dynamics of *Salmonella enterica*, *Listeria monocytogenes*, and *Escherichia coli* O157:H7 in wash water during simulated chlorine depletion and replenishment processes. *Food Microbiology*, 50, 88-96). Inactivation dynamics of *Salmonella enterica*, *Listeria monocytogenes*, and *Escherichia coli* O157:H7 in wash water during simulated chlorine depletion and replenishment processes. *Food Microbiology*, 50, 88-96). Lethality of chlorine based solutions increases as temperature increases, although, temperature does not affect the coefficient of pH. It has been observed that at 25 ppm concentration hypochlorite solution at pH 5, 7, and 10, the necessary exposure time to kill bacteria was increased by up to 2.3 times with each 10° C. drop in temperature (Block, S. S. (Ed.). (1991). *Disinfection, sterilization, and preservation* (4th ed). Philadelphia: Lea & Febiger).

In poultry and produce processing, chlorinated water, often sprayed or added to chill tank water, is the most common and widely used antimicrobial in the United States due to its low cost and efficacy against pathogens (Sohaib, M. et al. (2016) Postharvest intervention technologies for safety enhancement of meat and meat based products; a critical review. *Journal of Food Science and Technology*, 53(1), 19-30, 2016; Yang, Y., et al. (2012). Enhanced Chlorine Efficacy against Bacterial Pathogens in Wash Solution with High Organic Loads: Enhanced Chlorine Efficacy against Pathogens. *Journal of Food Processing and Preservation*, 36(6), 560-566). However, bacterial reductions on poultry show variable results. The incorporation of 18-25 ppm chlorine into chill water has been found to significantly reduce *Salmonella* (Sohaib, M. et al. (2016) Postharvest intervention technologies for safety enhancement of meat and meat based products; a critical review. *Journal of Food Science and Technology*, 53(1), 19-30). In poultry chiller tanks, chlorination of water has been found to be most effective if an initial level of 50 ppm FAC is used and maintained at 5 ppm residual chlorine (Najjar, M. B., & Meng, J. (2009). Risk Assessment of Disinfection Byproducts in Poultry Chilled in Chlorinated Water. Joint Institute for Food Safety and Nutrition and Department of Nutrition and Food Science). The produce industry uses high levels of chlorine, 25-250 ppm FAC, to inactivate pathogens due to a short contact time (Najjar, M. B., & Meng, J. (2009). Risk Assessment of Disinfection Byproducts in Poultry Chilled in Chlorinated Water. Joint Institute for Food Safety and Nutrition and Department of Nutrition and Food Science; Stopforth, J. D., et al. (2008). Effect of Acidified Sodium Chlorite, Chlorine, and Acidic Electrolyzed water on *Escherichia coli* O157:H7, *Salmonella*, and *Listeria monocytogenes* Inoculated on Leafy Greens. *Journal of Food Protection*, 71(3), 625-628). Most commercially available chlorine based sanitizers reduce pathogens on the surface of produce by 1-2 log cycles (Stopforth, J. D., et al. (2008). Effect of Acidified Sodium Chlorite, Chlorine, and Acidic Electrolyzed water on *Escherichia coli* O157:H7, *Salmonella*, and *Listeria monocytogenes* Inoculated on Leafy Greens. *Journal of Food Protection*, 71(3), 625-628; Yang, Y. et al. (2012). Enhanced Chlorine Efficacy against Bacterial Pathogens in Wash Solution with High Organic Loads: Enhanced Chlorine Efficacy against Pathogens. *Journal of Food Processing and Preservation*, 36(6), 560-566). While chlorine has been found to be an effective pathogen control, its capacity to inactivate pathogens on the surface of products, especially produce, is limited. Chlorine, however, is extremely effective at controlling pathogen levels in wash water (Zhou, B., Luo, Y., Nou, X., Lyu, S., & Wang, Q. (2015). Inactivation dynamics of *Salmonella enterica, Listeria monocytogenes*, and *Escherichia coli* O157:H7 in wash water during simulated chlorine depletion and replenishment processes. *Food Microbiology*, 50, 88-96).

Chlorinated water can also limit the growth of biofilms on food processing equipment (Najjar, M. B., & Meng, J. (2009). Risk Assessment of Disinfection Byproducts in Poultry Chilled in Chlorinated Water. Joint Institute for Food Safety and Nutrition and Department of Nutrition and Food Science). Chlorine based sanitizers are utilized to clean in-plant utensils, large equipment, and food contact surfaces with hypochlorite based 50-200 ppm FAC for a minimum of 10 seconds or longer (Block, S. S. (Ed.). (1991). *Disinfection, sterilization, and preservation* (4th ed). Philadelphia: Lea & Febiger). Block also reported the capacity of hypochlorite solutions to inhibit immediate biofilm growth when exposed to 0.5 and 5 ppm solutions or create extended antimicrobial effects after exposure to 50 ppm FAC solutions. As the FAC level in solution increases, logically, the antimicrobial capacity of the solution also increases as long as all other factors including pH, temperature, and organic content remain constant (Block, S. S. (Ed.). (1991). *Disinfection, sterilization, and preservation* (4th ed). Philadelphia: Lea & Febiger).

A major limitation of chlorine in the meat and poultry industry is that it is easily bound and deactivated by organic matter (Najjar, M. B., & Meng, J. (2009). Risk Assessment of Disinfection Byproducts in Poultry Chilled in Chlorinated Water. Joint Institute for Food Safety and Nutrition and Department of Nutrition and Food Science; Block, S. S. (Ed.). (1991). *Disinfection, sterilization, and preservation* (4th ed). Philadelphia: Lea & Febiger; Sohaib, M. et al. (2016) Postharvest intervention technologies for safety enhancement of meat and meat based products; a critical review. *Journal of Food Science and Technology*, 53(1), 19-30). The difference between the chlorine that is bound by organic matter and the residual chlorine that remains is referred to as chlorine demand (Block, S. S. (Ed.). (1991). *Disinfection, sterilization, and preservation* (4th ed). Philadelphia: Lea & Febiger). 'Breakpoint' chlorination is often used to account for chlorine demand by adding levels of chlorine in solution that satisfy initial demand and provide residual chlorine at levels necessary for antimicrobial action (Block, S. S. (Ed.). (1991). *Disinfection, sterilization, and preservation* (4th ed). Philadelphia: Lea & Febiger). In drinking water, where very low levels of organic materials are present, low levels of residual chlorine are effective. Higher levels of chlorine are required in the meat industry where high organic loads are encountered (Najjar, M. B., & Meng, J. (2009). Risk Assessment of Disinfection Byproducts in Poultry Chilled in Chlorinated Water. Joint Institute for Food Safety and Nutrition and Department of Nutrition and Food Science). However, in the presence of proteins (specifically amine, amide, imine, or imide N-groups) HOCl will form chloramines and retain some level of antimicrobial effect even when free available chlorine is reduced. Block reported 100% reductions of *Salmonella pullorum* in a 130 ppm hypochlorite solution with 5% organic matter, although there was no measurable level of FAC, thus showing the sanitizing capacity of chloramines (Block, S. S. (Ed.). (1991). *Disinfection, sterilization, and preservation* (4th ed). Philadelphia: Lea & Febiger). Aside from the presence and level of organic material in a solution, the initial chlorine levels, presence and level of catalysts (copper, nickel, cobalt), pH, temperature, and ultraviolet radiation are also factors that can decrease stability and effectiveness of chlorine in aqueous solution (Block, S. S. (Ed.). (1991). *Disinfection, sterilization, and preservation* (4th ed). Philadelphia: Lea & Febiger).

Nanobubble technology is a relatively new concept in the food industry, showing promise to aid in the development of improved food safety interventions. Currently, there are two types of nanobubbles available: 1) oxygen-nanobubbles, produced from air, and 2) ozonated nanobubbles. However, nanobubbles may be created using a range of gases, including oxygen, carbon dioxide, and the like (McTaggart, *Philosophical Magazine Series* 6:44 (1922) 386; Collins et al., *J. Colloid Interface Sci.* 63 (1978) 69). Nanobubbles are generally formed from the collapsing of microbubbles through a process known as cavitation, and are difficult to quantify and measure due to their size.

Micro- and nanobubbles are generally formed by cavitation; cavitation can be caused by acoustic, hydrodynamic, optic and/or particle based methods (Agarwal, A. et al. (2011). Principle and applications of microbubble and nanobubble technology for water treatment. *Chemosphere*, 84(9), 1175-1180). Acoustic nanobubbles are formed by passage of ultrasonic waves through a liquid solution, while hydrodynamic cavitation is directed by varying pressure and flow. Within these modes of formation, gas-water circulation and pressurized decompression methods are implemented for gas dissolution (Agarwal, A. et al. (2011). Principle and applications of microbubble and nanobubble technology for water treatment. *Chemosphere*, 84(9), 1175-1180). As described herein, nanobubbles may be generated, for example, by a generator that utilizes a hydrodynamic method involving cavitation chambers and shear planes to initiate an endothermic reaction (U.S. Pat. No. 8,454,837). This process produces a high concentration of paramagnetic oxygen nanobubbles with a mean particle size between 50 and 100 nm. The presence of unpaired electrons and the subsequent realignment of electron paths caused by a magnetic field causes paramagnetic properties. It was previously believed that nanobubbles disappeared in solution, but it is now understood that the bubbles are stable up to months after the dispersion of microbubbles due to their electrical charge (Agarwal, A. et al. (2011). Principle and applications of microbubble and nanobubble technology for water treatment. *Chemosphere*, 84(9), 1175-1180); Tsuge, H. (Ed.). (2014). Micro- and nanobubbles: fundamentals and applications. Singapore: Pan Stanford Publishing). Less than 1 µm in size, as often determined by dynamic light scattering, nanobubbles are most useful when measured by zeta potential. Zeta potential is surface charge of a molecule when suspended in a fluid system or the degree of repulsion between similarly charged particles in colloidal dispersions (Particle Sciences. (2012). *Zeta Potential (ZP): An Overview—Particle Sciences, Drug Development* (Technical Brief No. Volume 2). Bethlehem, Pa., retrieved from www.particlesciences.com/news/technical-briefs/2012/overview-of-zeta-potential.html; Tsuge, H. (Ed.). (2014). Micro- and nanobubbles: fundamentals and applications. Singapore: Pan Stanford Publishing). A high zeta potential will confer stability within a solution.

The interest in nanobubble technology has increased due to their proposed surfactant abilities or cleaning effect. Small particles in water can be effectively removed by introducing micro- or nanobubbles of opposing charge and zeta potential, which is controlled by the pH of the solution (Tsuge, H.

(Ed.). (2014). Micro- and nanobubbles: fundamentals and applications. Singapore: Pan Stanford Publishing). Agarwal et al. reported inhibition and removal of protein build-up on solid surfaces and stainless steel, thus preventing fouling, after application of nanobubbles (Agarwal, A. et al. (2011). Principle and applications of microbubble and nanobubble technology for water treatment. *Chemosphere,* 84(9), 1175-1180). Nanobubbles also provide increased surface area-to-volume ratio per mass as compared to standard water or other aqueous solutions. Without being bound by theory, this may enhance the efficiency of any dissolved or suspended antimicrobial components in solution. Currently, nanobubble technology is used most commonly to aid in wastewater disinfection. Micro- and nanobubbles generate free radicals, thus catalyzing chemical reactions and enhancing detoxification efficiency (Agarwal, A. et al. (2011). Principle and applications of microbubble and nanobubble technology for water treatment. *Chemosphere,* 84(9), 1175-1180). Agarwal et al. reported that implementation of nanobubble pretreatment to wastewater sources reduced overall biological, chemical, and physical loads and reduced the overall running costs of treating wastewater (Agarwal, A. et al. (2011). Principle and applications of microbubble and nanobubble technology for water treatment. *Chemosphere,* 84(9), 1175-1180).

Currently, there are few reported applications of nanobubbles in the food industry due to limited knowledge and available data. However, inclusion of nanobubble technology has been found to beneficially impact Japanese sake fermentation and shorten the number of growing days in hydroponic vegetable growing systems due to increased aeration in the soil (Tsuge, H. (Ed.). (2014). Micro- and nanobubbles: fundamentals and applications. Singapore: Pan Stanford Publishing). Nanobubble treatment, as a sanitation method, has been evaluated against norovirus surrogates in oyster bodies and was found to inactivate more than 99% of active virus after 12 hours (Tsuge, H. (Ed.). (2014). Micro- and nanobubbles: fundamentals and applications. Singapore: Pan Stanford Publishing). Ozonated nanobubbles have been observed to reduce *E. coli* by an additional 2 log cycles as compared to conventional ozone disinfection (Agarwal, A. et al. (2011). Principle and applications of microbubble and nanobubble technology for water treatment. *Chemosphere,* 84(9), 1175-1180). Soli et al. determined that 30 ppm FAC with a sucrose fatty acid ester (SFAE) solution compared to 30 ppm FAC with SFAE solution with the pretreatment application of a microbubble exposure aided in decreasing natural flora ~1 log CFU on lettuce as opposed to pretreatments without microbubbles, thus showing a surfactant capability (Soli, K. W. et al. (2010). Decontamination of fresh produce by the use of slightly acidic hypochlorous water following pretreatment with sucrose fatty acid ester under microbubble generation. *Food Control,* 21(9), 1240-1244). Moreover, nanobubbles produced through hydrodynamic cavitation have been observed to have a high inactivation capacity against *E. coli* (Agarwal, A. et al. (2011). Principle and applications of microbubble and nanobubble technology for water treatment. *Chemosphere,* 84(9), 1175-1180).

No data has been reported from evaluation of nanobubble water in combination with other antimicrobial constituents.
Chlorinated Nanobubble Antimicrobial Compositions and Methods and Systems of Use In some embodiments, the presently disclosed subject matter provides a method of treating a food product to reduce microbial content, comprising contacting the food product with a chlorinated nanobubble solution, wherein the chlorinated nanobubble solution comprises electrolyzed water, and wherein the microbial content of the food product is reduced by at least about 0.3 log CFU/g. In some embodiments, the electrolyzed water has an enhanced concentration of low zeta potential crystal and is generated by passing source water through a low zeta potential crystal generator and changing the crystalline structure of minerals in the source water. In another embodiment, the zeta potential of mineral crystals in the electrolyzed water after passage through the low zeta potential crystal generator is at least 25% less than the zeta potential of mineral particles in the source water. In another embodiment, the zeta potential of mineral crystals in the electrolyzed water after passage through the low zeta potential crystal generator is at least 50% less than the zeta potential of mineral particles in the source water.

In other embodiments within the method of treating a food product to reduce microbial content, the chlorinated nanobubble solution comprises nanobubbles having a diameter of less than 200 nm. In other embodiments, the chlorinated nanobubble solution comprises nanobubbles having a diameter of between 50 nm and 100 nm. In other embodiments, the chlorinated nanobubble solution comprises nanobubbles having a diameter of between 10 nm and 50 nm. In other embodiments, the chlorinated nanobubble solution comprises free available chlorine in an amount of less than 2,000 ppm. In other embodiments, the chlorinated nanobubble solution comprises free available chlorine in an amount of less than or equal to 300 ppm. In other embodiments, the chlorinated nanobubble solution comprises free available chlorine in an amount of less than or equal to 50 ppm. In other embodiments, the chlorinated nanobubble solution comprises free available chlorine in an amount of between 100 ppm and 300 ppm. In other embodiments, the chlorinated nanobubble solution comprises free available chlorine in an amount of between 50 ppm and 300 ppm. In other embodiments, the chlorinated nanobubble solution comprises free available chlorine in an amount of between 0.5 ppm and 50 ppm. In other embodiments, the chlorinated nanobubble solution has a pH of less than 7. In other embodiments, the chlorinated nanobubble solution has a pH of between 5 and 7. In other embodiments, the chlorinated nanobubble solution has a pH of 5.

In other embodiments within the method of treating a food product to reduce microbial content, the food product is selected from the group consisting of meat, vegetables, fruit, and eggs in their shell. In other embodiments, the meat is selected from the group consisting of beef, poultry, and pork.

In some embodiments, the presently disclosed subject matter provides a method of treating a food product preparation or packaging surface to reduce microbial content, comprising contacting the food product preparation or packaging surface with a chlorinated nanobubble solution, wherein the chlorinated nanobubble solution comprises electrolyzed water, and wherein the microbial content of the food product is reduced by at least about 0.3 log CFU/g. In some embodiments, the electrolyzed water has an enhanced concentration of low zeta potential crystal and is generated by passing source water through a low zeta potential crystal generator and changing the crystalline structure of minerals in the source water. In another embodiment, the zeta potential of mineral crystals in the electrolyzed water after passage through the low zeta potential crystal generator is at least 25% less than the zeta potential of mineral particles in the source water. In another embodiment, the zeta potential of mineral crystals in the electrolyzed water after passage through the low zeta potential crystal generator is at least 50% less than the zeta potential of mineral particles in the source water.

In other embodiments within the method of treating a food product preparation or packaging surface to reduce microbial content, the chlorinated nanobubble solution comprises nanobubbles having a diameter of less than 200 nm. In other embodiments, the chlorinated nanobubble solution comprises nanobubbles having a diameter of between 50 nm and 100 nm. In other embodiments, the chlorinated nanobubble solution comprises nanobubbles having a diameter of between 10 nm and 50 nm. In other embodiments, the chlorinated nanobubble solution comprises free available chlorine in an amount of less than 2,000 ppm. In other embodiments, the chlorinated nanobubble solution comprises free available chlorine in an amount of less than or equal to 300 ppm. In other embodiments, the chlorinated nanobubble solution comprises free available chlorine in an amount of less than or equal to 50 ppm. In other embodiments, the chlorinated nanobubble solution comprises free available chlorine in an amount of between 100 ppm and 300 ppm. In other embodiments, the chlorinated nanobubble solution comprises free available chlorine in an amount of between 50 ppm and 300 ppm. In other embodiments, the chlorinated nanobubble solution comprises free available chlorine in an amount of between 0.5 ppm and 50 ppm. In other embodiments, the chlorinated nanobubble solution has a pH of less than 7. In other embodiments, the chlorinated nanobubble solution has a pH of between 5 and 7. In other embodiments, the chlorinated nanobubble solution has a pH of 5.

In other embodiments within the method of treating a food product preparation or packaging surface to reduce microbial content, the food product preparation or packaging surface is used to prepare or package a food product selected from the group consisting of meat, vegetables, fruit, and eggs in their shell. In other embodiments, the meat is selected from the group consisting of beef, poultry, and pork.

In some embodiments, the presently disclosed subject matter provides a method of reducing the growth of bacteria and reversing the growth of biofilm in a water system, comprising chlorinating source water and passing the chlorinated source water through a low zeta potential crystal generator and changing the crystalline structure of minerals in the source water to produce treated chlorinated water having an enhanced concentration of low zeta potential crystal, and wherein the microbial content of the treated chlorinated water is reduced by at least about 0.3 log CFU/mL compared to the source water.

In some embodiments of the method of reducing the growth of bacteria and reversing the growth of biofilm in a water system, the electrolyzed water has an enhanced concentration of low zeta potential crystal and is generated by passing source water through a low zeta potential crystal generator and changing the crystalline structure of minerals in the source water. In another embodiment, the zeta potential of mineral crystals in the electrolyzed water after passage through the low zeta potential crystal generator is at least 25% less than the zeta potential of mineral particles in the source water. In another embodiment, the zeta potential of mineral crystals in the electrolyzed water after passage through the low zeta potential crystal generator is at least 50% less than the zeta potential of mineral particles in the source water.

In other embodiments within the method of reducing the growth of bacteria and reversing the growth of biofilm in a water system, the chlorinated nanobubble solution comprises nanobubbles having a diameter of less than 200 nm. In other embodiments, the chlorinated nanobubble solution comprises nanobubbles having a diameter of between 50 nm and 100 nm. In other embodiments, the chlorinated nanobubble solution comprises nanobubbles having a diameter of between 10 nm and 50 nm. In other embodiments, the chlorinated nanobubble solution comprises free available chlorine in an amount of less than 2,000 ppm. In other embodiments, the chlorinated nanobubble solution comprises free available chlorine in an amount of less than or equal to 300 ppm. In other embodiments, the chlorinated nanobubble solution comprises free available chlorine in an amount of less than or equal to 50 ppm. In other embodiments, the chlorinated nanobubble solution comprises free available chlorine in an amount of between 100 ppm and 300 ppm. In other embodiments, the chlorinated nanobubble solution comprises free available chlorine in an amount of between 50 ppm and 300 ppm. In other embodiments, the chlorinated nanobubble solution comprises free available chlorine in an amount of between 0.5 ppm and 50 ppm. In other embodiments, the chlorinated nanobubble solution has a pH of less than 7. In other embodiments, the chlorinated nanobubble solution has a pH of between 5 and 7. In other embodiments, the chlorinated nanobubble solution has a pH of 5.

In some embodiments, the presently disclosed subject matter provides a method for purifying water, comprising chlorinating the water and passing the chlorinated water through a low zeta potential crystal generator and changing the crystalline structure of minerals in the chlorinated water to produce treated chlorinated water having an enhanced concentration of low zeta potential crystal, and wherein the treated chlorinated water has a particle concentration of less than 20,000,000 particles/mL. In some embodiments, the treated chlorinated water has a particle concentration of less than 15,000,000 particles/mL. In other embodiments, the treated chlorinated water has a particle concentration of less than 10,000,000 particles/mL.

In some embodiments of the method for purifying water, the electrolyzed water has an enhanced concentration of low zeta potential crystal and is generated by passing the water through a low zeta potential crystal generator and changing the crystalline structure of minerals in the water. In another embodiment, the zeta potential of mineral crystals in the electrolyzed water after passage through the low zeta potential crystal generator is at least 25% less than the zeta potential of mineral particles in the water. In another embodiment, the zeta potential of mineral crystals in the electrolyzed water after passage through the low zeta potential crystal generator is at least 50% less than the zeta potential of mineral particles in the water.

In other embodiments within the method for purifying water, the chlorinated nanobubble solution comprises nanobubbles having a diameter of less than 200 nm. In other embodiments, the chlorinated nanobubble solution comprises nanobubbles having a diameter of between 50 nm and 100 nm. In other embodiments, the chlorinated nanobubble solution comprises nanobubbles having a diameter of between 10 nm and 50 nm. In other embodiments, the chlorinated nanobubble solution comprises free available chlorine in an amount of less than 2,000 ppm. In other embodiments, the chlorinated nanobubble solution comprises free available chlorine in an amount of less than or equal to 300 ppm. In other embodiments, the chlorinated nanobubble solution comprises free available chlorine in an amount of less than or equal to 50 ppm. In other embodiments, the chlorinated nanobubble solution comprises free available chlorine in an amount of between 100 ppm and 300 ppm. In other embodiments, the chlorinated nanobubble solution comprises free available chlorine in an amount of between 50 ppm and 300 ppm. In other embodiments, the chlorinated nanobubble solution comprises free available chlorine in an amount of between 0.5 ppm and 50 ppm. In other embodiments, the chlorinated nanobubble solution has a pH of less than 7. In other embodiments, the chlorinated nanobubble solution has a pH of between 5 and 7. In other embodiments, the chlorinated nanobubble solution has a pH of 5.

Concluding Remarks

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

EXAMPLES

Example 1

Efficacy of Chlorinated Nanobubble Solutions to Control Shiga Toxin-Producing *E. coli*, *Salmonella* spp., and Non-Pathogenic Surrogate *E. coli* in a Model Beef Processing 1.1. Determining Minimum Bactericidal Concentrations of Chlorinated Waters in Pure Cultures Numerous antimicrobials, including lactic and peroxyacetic acids, are widely used in raw beef processing to reduce the presence of foodborne pathogens such as Shiga toxin-producing *E. coli* (STEC) and *Salmonella*; however, there is interest in exploring combinations of various technologies to enhance antimicrobial effects on pathogens and to support proprietary developments in beef processing. Chemical residues from traditional antimicrobials can lead to deterioration of quality attributes, including appearance, texture, and taste, and potential human health hazards (Tsuge, H. (Ed.). (2014). *Micro- and nanobubbles: fundamentals and applications*. Singapore: Pan Stanford Publishing). Therefore, interventions requiring very low levels of active chemicals are of interest.

Chlorinated water is the most commonly used antimicrobial in the U.S. produce and poultry industries due to its low cost and efficacy against pathogens (Sohaib, M., et al. (2016). Postharvest intervention technologies for safety enhancement of meat and meat based products; a critical review. *Journal of Food Science and Technology*, 53(1), 19-30; Yang, Y., et al. (2012). Enhanced Chlorine Efficacy against Bacterial Pathogens in Wash Solution with High Organic Loads: Enhanced Chlorine Efficacy against Pathogens. *Journal of Food Processing and Preservation*, 36(6), 560-566). Chlorine can be applied as an antimicrobial in a variety of forms as directed by the USDA FSIS Safe and Suitable Ingredients list (USDA Food Safety and Inspection Service. (2016). *Safe and suitable ingredients used in the production of meat, poultry, and egg products* (No. FSIS Directive 7120.1 Rev. 37). Washington D.C.) for meat and poultry. One method of generating chlorine in water solutions using low levels of chemicals is with electrolyzed (EO) water. The application of EO water at 5-7 pH minimizes detrimental health effects from Cl2 gassing off (Guentzel, J. L., et al. (2008). Reduction of bacteria on spinach, lettuce, and surfaces in food service areas using neutral electrolyzed oxidizing water. *Food Microbiology*, 25(1), 36-41) while maintaining the antimicrobial effects of hypochlorous acid (HOCl) present in solution. HOCl is the most effective form of chlorine for disinfection; at pH 5 HOCl constitutes 97% of total chlorine in solution (Park et al., 2004).

A relatively new concept in the food industry, nanobubble technology shows promise to aid in the development of improved food safety interventions. There is interest in nanobubbles due their proposed surfactant abilities and cleaning effect. Small particles in water can be effectively removed by introducing nanobubbles of opposing charge and zeta potential, which is controlled by the pH of the solution (Tsuge, H. (Ed.). (2014). *Micro- and nanobubbles: fundamentals and applications*. Singapore: Pan Stanford Publishing). Nanobubbles also provide increased surface area-to-volume ratio per mass as compared to standard water or other aqueous solutions (Bauer (2016) Nanobubbles from www.nanobubbles.com, Retrieved Oct. 3, 2016), which theoretically enhances the efficiency of any dissolved or suspended antimicrobial components in solution. Nanobubble treatment, as a sanitation method, has been evaluated against norovirus surrogates in oyster bodies and was found to inactivate more than 99% of active virus after 12 hours (Tsuge, H. (Ed.). (2014). *Micro- and nanobubbles: fundamentals and applications*. Singapore: Pan Stanford Publishing).

EO water has been evaluated for use as a disinfectant and antimicrobial in food processing environments; however, research has not yet been conducted to determine if nanobubble technology aids in the antimicrobial effectiveness of chlorine based solutions. The primary goal of this experiment was to characterize lethality contributions of combinations of acidity (pH 5 or 7), level of free chlorine (zero, low, medium, or high), presence of nanobubble technology, and variation in processing temperature (1.6 or 5.5° C.) in Cesco-NAN-02 technology water [i.e. municipal water that is chlorinated by infusion of concentrated chorine produced through an electrolyzed (EO) water process, acidified by introduction of $CO_2$ gas, and then passed through a patented nanobubble generator] against STEC, *Salmonella* spp., and non-pathogenic surrogate organisms in pure solution.

Materials and Methods

Bacterial Cultures and Inoculum Preparation

Five strains of rifampicin-resistant non-pathogenic surrogate *Escherichia coli* (ATCC BAA-1427 P1, BAA-1428 P3, BAA-1429 P8, BAA-1430 P14, and BAA-1431 P68) obtained from Dr. Gary Acuff (Texas A&M University, College Station, Tex.), five strains of *Salmonella* [four beef lymph node isolates (serotypes Lubbock, Mbandaka, and Montevideo) and one fecal (Mbandaka) isolate obtained from Dr. Guy Loneragan (Texas Tech University, Lubbock, Tex.) and *S. Typhimurium* ATCC 14028], and seven STEC strains [STEC-7; O26 (H30), O45 (CDC 96-3285), O103 (90-3128), O111 (JBI-95), O121 (CDC 97-3068), O145 (83-75) and O157:H7 (ATCC 35150), referred to as STEC- 7], trained to be resistant to rifampicin (Laster, B. A., et al. (2012). Efficacy of trimming chilled beef during fabrication to control *Escherichia coli* O157:H7 surrogates on subsequent subprimals. *Meat Science,* 90(2), 420-425) at 0.1 g/L, obtained from Dr. John Luchansky (USDA Eastern Regional Research Center, Wyndmoor, Pa.) were used in this study. All cultures were received from their sources, transferred into fresh tryptic soy broth (TSB or TSB+rifampicin; Bacto, Becton Dickinson, Sparks, N.J., USA), incubated for 24 h at 37° C., and streaked onto tryptic soy agar (TSA or TSA+rifampicin) for confirmation using API 20E assays (BioMerieux Vitek, Hazelwood, Mo., USA) and BioControl Assurance GDS PCR assays. Broth cultures were then stored on cryoprotect beads in glycerol at −80° C. until needed.

Each bacterial strain was activated individually by transferring a single cryogenically frozen bead into either TSB containing 0.1 g/L rifampicin (rif; Sigma-Aldrich, St. Louis, Mo., USA) stock solution (TSB+rif for the rifampicin-resistant STEC-7 and surrogates) or TSB (for *Salmonella serovars*) and incubated at 37° C. for 24 hours. Rifampicin stock solution (rif) was prepared by dissolving 0.1 g rifampicin in 5 mL methanol (Fisher Chemical, Fair Lawn, N.J., USA) followed by filtering through a 0.22 µm sterile filter. Activated *Salmonella* strains were individually transferred into 45 mL TSB, surrogates into 45 mL TSB+rif, and STEC-7 strains into 32 mL TSB+rif and incubated at 37° C. for 24 hours. After incubation, each culture strain was individually plated onto either TSA plates containing 0.1 g/L rif (TSA+rif) for rif-resistant STEC-7 and surrogates or xylose lysine deoxycholate (XLD; Difco, Becton Dickinson, Sparks, N.J., USA) agar for *Salmonella* spp. to determine concentration. Culture strains within the three target bacterial strain groups were combined into 220 mL mixed cocktails to be centrifuged at 5,520×g for 15 minutes at −4° C. Centrifuged pellets were refrigerated overnight at 4° C. and re-hydrated in 60 mL phosphate buffered saline (PBS) prior to use.

Antimicrobial Water Solutions

All test solutions were generated by Cesco-NAN-02 technology (Bellingham, Wash.) and ground shipped to Kansas State University in sealed 5 L plastic containers for inoculated laboratory benchtop trials. Cesco-NAN-02 technology water [i.e. municipal water that is continuously chlorinated by infusion of concentrated chorine produced through an electrolyzed (EO) water process, acidified by introduction of $CO_2$ gas, and then passed through a patented nanobubble generator (U.S. Pat. No. 8,454,837)] solutions containing 4 levels of free available chlorine [FAC; zero, low (2.91±0.45 ppm), medium (7.27±0.36 ppm), and high (11.94±0.97 ppm)], infused by addition of EO water, were evaluated either with or without nanobubbles and at both acidic (5) and neutral (7) pH levels. Control treatments containing no FAC and no nanobubbles at pH 5 and 7 were evaluated for comparison. Nanobubbles are generated utilizing cavitation chambers and shear planes to initiate an endothermic reaction, thus, producing a high concentration of paramagnetic oxygen nanobubbles with a mean particle size between 50 and 100 nm (Bauer (2016) Nanobubbles from www.nanobubbles.com, Retrieved Oct. 3, 2016). Each shipment of solutions was evaluated within 5 days of arrival at the Kansas State University Food Safety & Defense Laboratory and within 12 days of generation. FAC, pH, and ORP were measured for each sample collected using a portable photometer (HI96711 Portable Photometer, Hanna Instruments, Woonsocket, R.I., USA; PT3 and PT4 pens, Myron L Company, Carlsbad, Calif., USA). It should be noted that Cesco-NAN-02 technology nanobubble solutions were provided for this research, and were generated at the commercial site according to proprietary methodology. Through company experience, specific ORP readings at the plant was used as an indicator of presence and concentration of suspended nanobubbles; however, other than reading the ORP upon receipt and at the time of experimental trial, the K-State laboratory had no method of confirming the actual presence of nanobubbles. However, elevated ORP readings in nanobubble water were similar in the laboratory compared to the commercial plant.

Application of Chlorinated Water Treatments to Pure Cultures

Each of the 32 total treatment combinations of chlorine level, acidity, and presence/absence of nanobubbles were evaluated for their bactericidal effect on separate multi-strain cocktails of the three target bacterial populations (Table 1). Aliquots (24.75 mL) of each Cesco-NAN-02 technology solution were equilibrated to either 1.7° C. or 5.6° C. in 100-mL glass beakers and were agitated with a small sterile stir-bar at 600 rpm (Isotemp, Fischer Scientific, Dubuque, Iowa, USA). Solutions were inoculated with 0.25 mL (~9.7 log CFU/mL) of the three rehydrated culture cocktails individually—with consideration of the dilution factor due to addition to test solutions, the level of total organisms in solution was ~7.7 log CFU/mL—and each exposed for 1 minute before neutralizing directly with 25 mL double-strength DE Neutralizing Broth (Difco, Becton, Dickinson and Co., Sparks, Md., USA).

TABLE 1

Parameters Evaluated in Cesco-NAN-02 Technology Water During Determination of Minimum Bactericidal Concentrations of Chlorinated Waters in Pure Cultures.

| Temperature (° C.) | pH | Chlorine (ppm) | Nanobubbles |
|---|---|---|---|
| 1.6 | 5 | Zero (0) | Presence |
| 5.6 | 7 | Low (2.91 ± 0.45) | Absence |
|  |  | Medium (7.27 ± 0.36) |  |
|  |  | High (11.94 ± 0.97) |  |

Microbial Analysis

Surviving populations of inoculum cocktails were determined by immediately plating serial dilutions of each neutralized sample onto injury recovery and selective media agar plates. Serial dilutions were prepared in Phosphate Buffered Saline (PBS; AMRESCO, LLC., Solon, Ohio, USA) blanks. STEC-7 and surrogates were enumerated by spread plating on TSA+rif and *Salmonella* spp. was enumerated on XLD agar, each incubated for 24 hours at 37° C. To quantify sublethally injured cells, samples were also spread plated onto non-selective TSA, incubated for 6 hours at 37° C., overlayed with 10 mL TSA+rif or XLD to select for STEC-7 and/or surrogates and *Salmonella* spp., respectively, and incubated for 12-18 additional hours at 37° C.

Statistical Analysis

Statistical analysis was performed using the MIXED procedure in SAS 9.4 (SAS Institute Inc., Cary, N.C., USA). A split-split-split-plot treatment structure was assumed with chlorine level as the whole-plot treatment factor arranged in an incomplete block design with day as the blocking factor, temperature as the subplot factor with all other treatment factors (combinations of acidity, presence of nanobubbles, and target organism tested) in the sub-subplot structure, and media type (selective or injury recovery) as the sub-sub-sub plot factor. Type 3 tests of fixed effects were evaluated to determine significance of interactions and/or main effects based on a significance level of α=0.05.

Results and Discussion

The efficacy of chlorine to inactivate pathogens is dependent on concentration, pH level, contact time, temperature, and bacterial strains—all factors which were evaluated in this study along with the presence/absence of suspended nanobubbles in solution. Although post-treatment recovery of the 3 bacterial populations was variable across replications, notable reductions ranging from 3.3-7.0 log CFU/mL were observed across all three (low, medium, and high) FAC levels. Analysis of the Type 3 Fixed Effects (Table 2) indicate there was a significant 5-way interaction between type of organism, temperature, pH, presence of nanobubbles, and media (selective or injury recovery; $P \leq 0.05$).

TABLE 2

Type 3 Fixed Effects of Split-Split-Split Plot Analysis.

| Effect | Num. DF | Denom. DF | F Value | P Value |
|---|---|---|---|---|
| Chlorine | 3 | 12.659 | 251.984 | 1.53842E−11 |
| Organism | 2 | 272.543 | 14.890 | 7.29284E−07 |
| Chlorine*Organism | 6 | 272.513 | 8.853 | 7.8893E−09 |
| Temperature | 1 | 16.021 | 0.023 | 0.882 |
| Chlorine*Temperature | 3 | 16.407 | 0.123 | 0.945 |
| Organism*Temperature | 2 | 272.425 | 1.338 | 0.264 |
| Chlorine*Organism*Temperature | 6 | 272.408 | 0.425 | 0.862 |
| pH | 1 | 272.365 | 1.173 | 0.280 |
| Chlorine*pH | 3 | 272.352 | 3.622 | 0.014 |
| Organism*pH | 2 | 272.543 | 2.107 | 0.124 |
| Chlorine*Organism*pH | 6 | 272.514 | 0.543 | 0.775 |
| Temperature*pH | 1 | 272.605 | 0.054 | 0.816 |
| Chlorine*Temperature*pH | 3 | 272.572 | 0.048 | 0.986 |
| Organism*Temperature*pH | 2 | 272.425 | 0.632 | 0.533 |
| Chlorine*Organism*Temperature*pH | 6 | 272.407 | 3.048 | 0.007 |
| Nanobubbles | 1 | 283.021 | 1.345 | 0.247 |
| Chlorine*Nanobubbles | 3 | 278.431 | 0.229 | 0.876 |
| Organism*Nanobubbles | 2 | 272.425 | 0.900 | 0.408 |
| Chlorine*Organism*Nanobubbles | 6 | 272.407 | 0.648 | 0.691 |
| Temperature*Nanobubbles | 1 | 283.257 | 0.209 | 0.648 |
| Chlorine*Temperature*Nanobubbles | 3 | 262.998 | 0.643 | 0.588 |
| Organism*Temperature*Nanobubbles | 2 | 272.543 | 1.511 | 0.223 |
| Chlorine*Organism*Temperature*Nanobubbles | 6 | 272.514 | 2.274 | 0.037 |
| pH*Nanobubbles | 1 | 272.605 | 0.428 | 0.514 |
| Chlorine*pH*Nanobubbles | 3 | 272.572 | 0.650 | 0.583 |
| Organism*pH*Nanobubbles | 2 | 272.425 | 0.938 | 0.393 |
| Chlorine*Organism*pH*Nanobubbles | 6 | 272.408 | 1.554 | 0.161 |
| Temperature*pH*Nanobubbles | 1 | 272.365 | 0.205 | 0.651 |
| Chlorine*Temperature*pH*Nanobubbles | 3 | 272.352 | 0.667 | 0.573 |
| Organism*Temperature*pH*Nanobubbles | 2 | 272.543 | 0.637 | 0.530 |
| Chlorine*Organism*Temperature*pH*Nanobubbles | 6 | 272.513 | 0.301 | 0.936 |
| Media | 1 | 297.113 | 187.070 | 2.30E−33 |
| Chlorine*Media | 3 | 297.115 | 7.152 | <0.0001 |
| Organism*Media | 2 | 297.113 | 7.353 | 0.001 |
| Chlorine*Organism*Media | 6 | 297.115 | 3.445 | 0.003 |
| Temperature*Media | 1 | 297.113 | 2.227 | 0.137 |
| Chlorine*Temperature*Media | 3 | 297.115 | 0.625 | 0.600 |
| Organism*Temperature*Media | 2 | 297.113 | 0.319 | 0.727 |
| Chlorine*Organism*Temperature*Media | 6 | 297.115 | 1.564 | 0.157 |
| pH*Media | 1 | 297.113 | 0.970 | 0.325 |
| Chlorine*pH*Media | 3 | 297.115 | 0.937 | 0.423 |
| Organism*pH*Media | 2 | 297.113 | 0.299 | 0.741 |
| Chlorine*Organism*pH*Media | 6 | 297.115 | 1.359 | 0.231 |
| Temperature*pH*Media | 1 | 297.113 | 0.324 | 0.570 |
| Chlorine*Temperature*pH*Media | 3 | 297.115 | 0.759 | 0.518 |
| Organism*Temperature*pH*Media | 2 | 297.113 | 0.443 | 0.642 |
| Chlorine*Organism*Temperature*pH*Media | 6 | 297.115 | 0.790 | 0.578 |
| Nanobubbles*Media | 1 | 297.113 | 0.275 | 0.600 |
| Chlorine*Nanobubbles*Media | 3 | 297.115 | 0.085 | 0.968 |
| Organism*Nanobubbles*Media | 2 | 297.113 | 0.473 | 0.624 |
| Chlorine*Organism*Nanobubbles*Media | 6 | 297.115 | 2.282 | 0.036 |
| Temperature*Nanobubbles*Media | 1 | 297.113 | 0.424 | 0.515 |
| Chlorine*Temperature*Nanobubbles*Media | 3 | 297.115 | 0.872 | 0.456 |
| Organism*Temperature*Nanobubbles*Media | 2 | 297.113 | 0.083 | 0.920 |
| Chlorine*Organism*Temperature*Nanobubbles*Media | 6 | 297.115 | 0.336 | 0.918 |
| pH*Nanobubbles*Media | 1 | 297.113 | 1.742 | 0.188 |
| Chlorine*pH*Nanobubbles*Media | 3 | 297.115 | 4.894 | 0.002 |
| Organism*pH*Nanobubbles*Media | 2 | 297.113 | 3.499 | 0.031 |
| Chlorine*Organism*pH*Nanobubbles*Media | 6 | 297.115 | 1.183 | 0.315 |
| Temperature*pH*Nanobubbles*Media | 1 | 297.113 | 2.294 | 0.131 |
| Chlorine*Temperature*pH*Nanobubbles*Media | 3 | 297.115 | 2.501 | 0.060 |

TABLE 2-continued

Type 3 Fixed Effects of Split-Split-Split Plot Analysis.

| Effect | Num. DF | Denom. DF | F Value | P Value |
|---|---|---|---|---|
| Organism*Temperature*pH*Nanobubbles*Media | 2 | 297.113 | 4.784 | 0.009 |
| Chlorine*Organism*Temperature*pH*Nanobubbles*Media | 6 | 297.115 | 1.123 | 0.348 |

*Shaded highlights indicate significant interactions and effects (P < 0.05).

Figure 3:
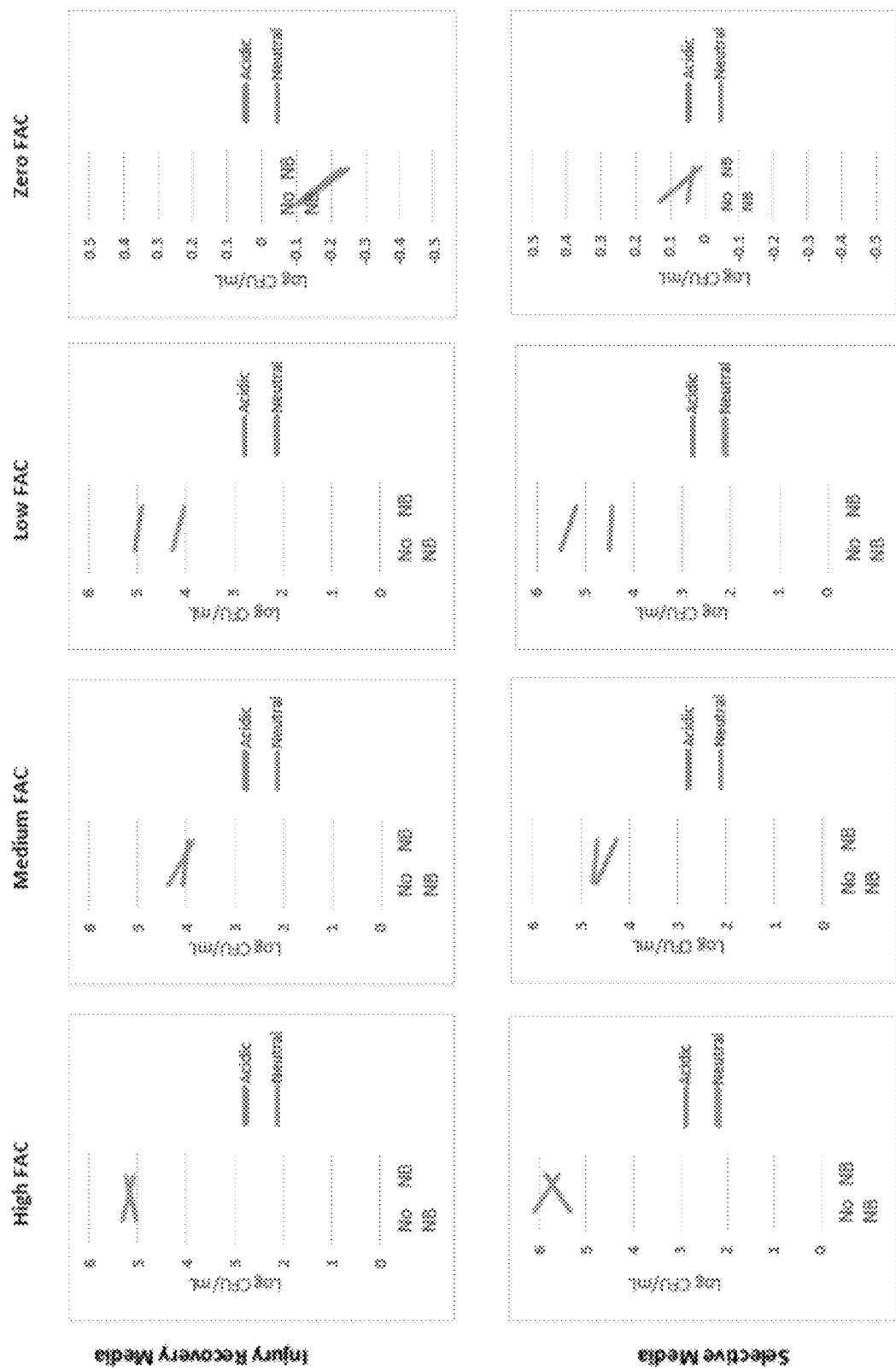
FIG. 3 shows a Profile Plot of 4-Way Interaction between Level of Chlorine (high, medium, low, zero FAC), pH (Acidic or Neutral), Presence of Nanobubbles (NB), and Media Type. Least Square Means (Avg. Log CFU/mL) of Log CFU/mL reductions are reported for each combination.
Figure 4:
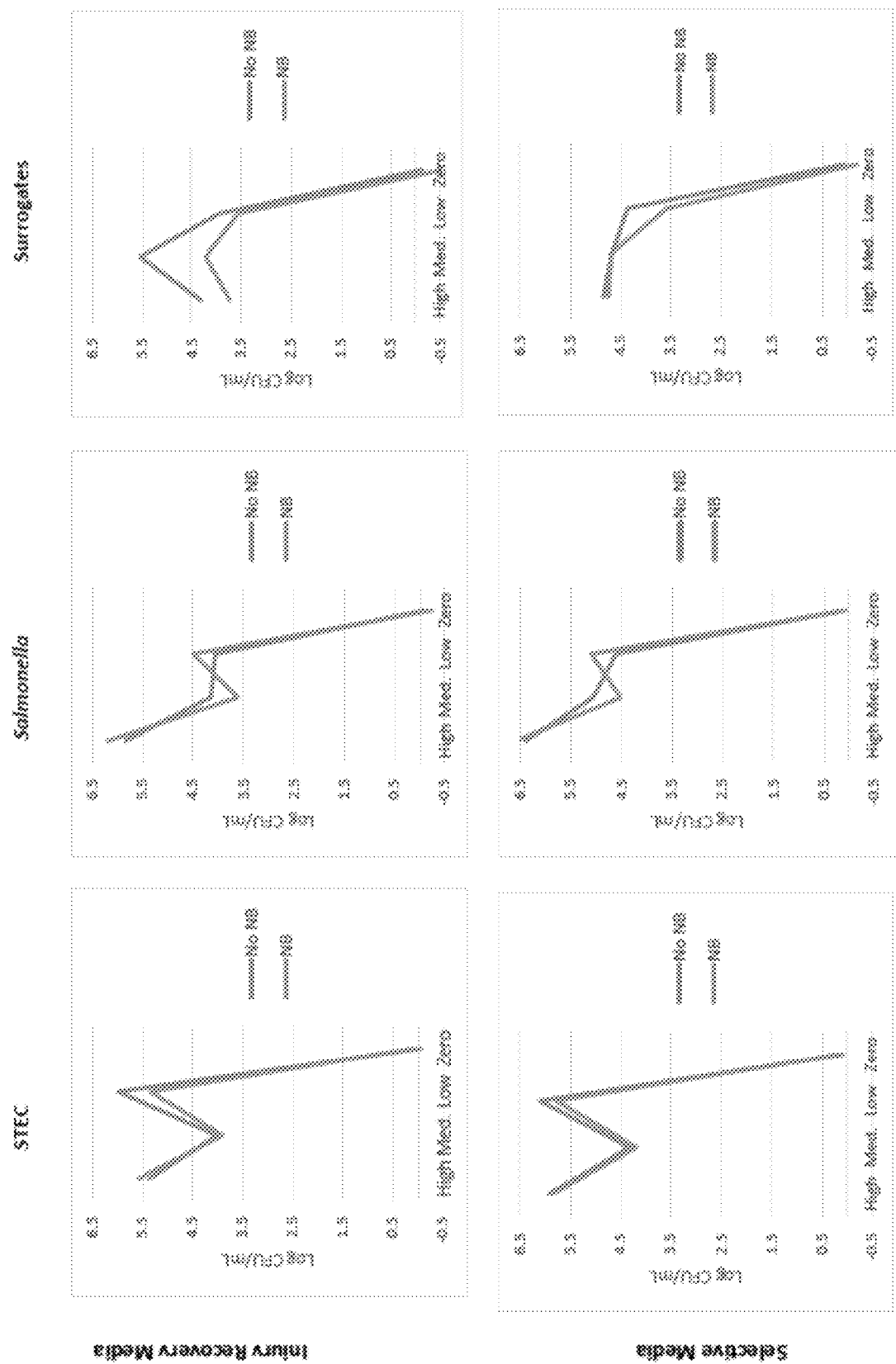
FIG. 4 shows a Profile Plot of 4-Way Interaction between Level of Chlorine (high, med., low, zero), Type of Organism, Presence of Nanobubbles (NB), and Media Type. Least Square Means (Avg. Log CFU/mL) of Log CFU/mL reductions are reported for each combination.

In FIGS. 1, 3, and 4, parallel lines indicate no interaction between factors or levels of factors whereas non-parallel or crossed lines indicate an interaction.

Figure 2:
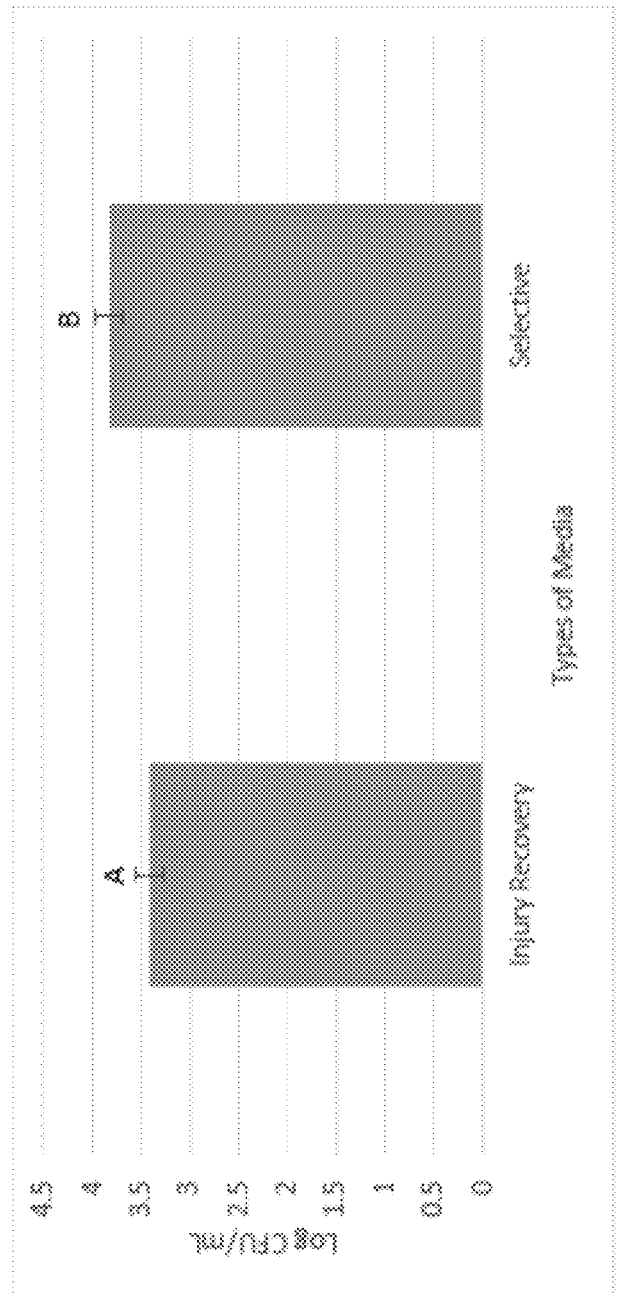
FIG. 2 shows Average Log CFU/mL Reductions Based on Type of Media; A-B different letters indicate significant differences ($P \le 0.05$).

The effect of media type (selective or injury recovery) was dependent on the interactions between type of organism, temperature, pH, and presence of nanobubbles regardless of chlorine level. Level of chlorine was found to be a significant contributor (P≤0.05), as indicated in Table 2, in four 4-way interactions; however, two of these interactions are more important to analyze as they show the effect of chlorine on media type, which is a factor in our highest order interaction. The first interaction, Chlorine*pH*Nanobubbles*Media, indicates that the effect of media type was dependent on the interactions between pH, presence of nanobubbles, and level of chlorine (FIG. 3). The second interaction, Chlorine*Organism*Nanobubbles*Media, indicates the effect of media type was also dependent on the interactions between level of chlorine, type of organism, and presence of nanobubbles (FIG. 4). As the highest order, these significant (P≤0.05) 4- and 5-way interactions must be considered. First order main effects show that the individual components of greatest importance, i.e. type of media (FIG. 2), level of chlorine (FIG. 6), and type of organism (FIG. 5), are significantly different within their levels (P≤0.05) averaged across levels of all other factors, whereas there are no significant (P>0.05) differences between the two exposure temperatures or the presence of nanobubbles averaged across levels of all other factors (Table 2).

FIG. 4 reports differences in log CFU/mL reductions between the injury recovery and selective media types; injury recovery reductions were 0.42 log CFU/mL lower (P≤0.05). This corresponds to higher recovery counts on injury recovery media. When conducting further experiments, researchers can use this information to save time, supplies, financial and human resources, to justify spread plating and/or reporting results obtained using injury recovery media only. If reviewing injury recovery media data only, having lower overall reductions will lead researchers to make more conservative decisions when evaluating the success of chlorinated nanobubble antimicrobials in future studies.

Figure 5:
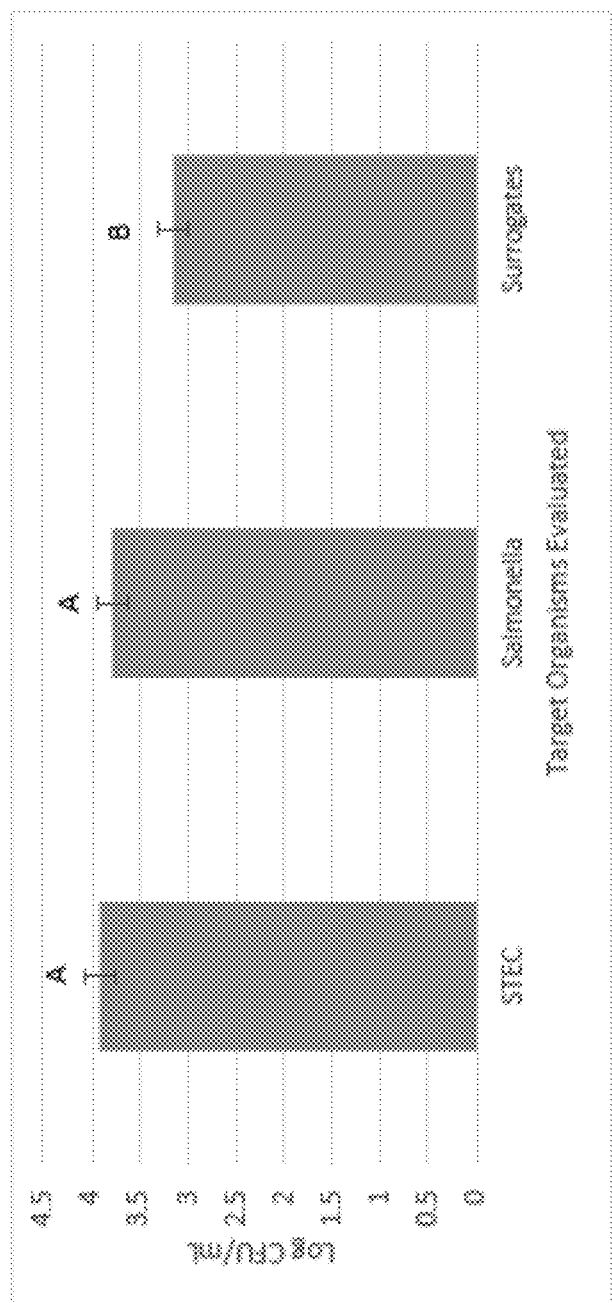
FIG. 5 shows Average Log CFU/mL Reductions Based on Type of Organism; A-B different letters indicate significant differences ($P \le 0.05$).

Similarly, when observing differences between target organism cocktail populations, the same logic applies. Surrogate *E. coli* demonstrated significantly greater resistance to the chlorinated solutions; population reductions ranged from 3.4-5.5 log CFU/mL with only slightly increased reductions at the higher FAC level. FIG. 5 depicts significant differences between STEC-7 and surrogates, and likewise between *Salmonella* and surrogates, with surrogate reductions being ~0.70 log CFU/mL lower (P≤0.05). The lower average population reduction (i.e., higher viable cell recovery) indicates that the 5-strain surrogate cocktail is a good predictor for both STEC-7 and *Salmonella* behavior when evaluating chilled chlorinated nanobubble antimicrobial solutions, particularly for commercial in-plant validation studies. In this benchtop study, STEC-7 reductions were the most variable ranging from 3.3-7.0 log CFU/mL; whereas, *Salmonella* populations were notably reduced (4.9-7.1 log CFU/mL) by the high FAC concentrations. No definitive impacts of nanobubble inclusion or acidic pH were observed for any of the three target bacterial cocktails in pure solution testing.

Differences between the levels of FAC in solution were observed (FIG. 6), with high FAC being more effective (P≤0.05) in reducing organism populations (by an average of 5.4 log CFU/mL) than the low, medium, or zero FAC levels. No differences (P>0.05) in microbial reductions were detected between low and medium FAC levels, both reducing populations by ~4.5 log CFU/mL. All levels of chlorinated test solutions (low, medium and high) reduced target organism populations more effectively (P≤0.05) than the zero FAC control solutions.

Figure 6:
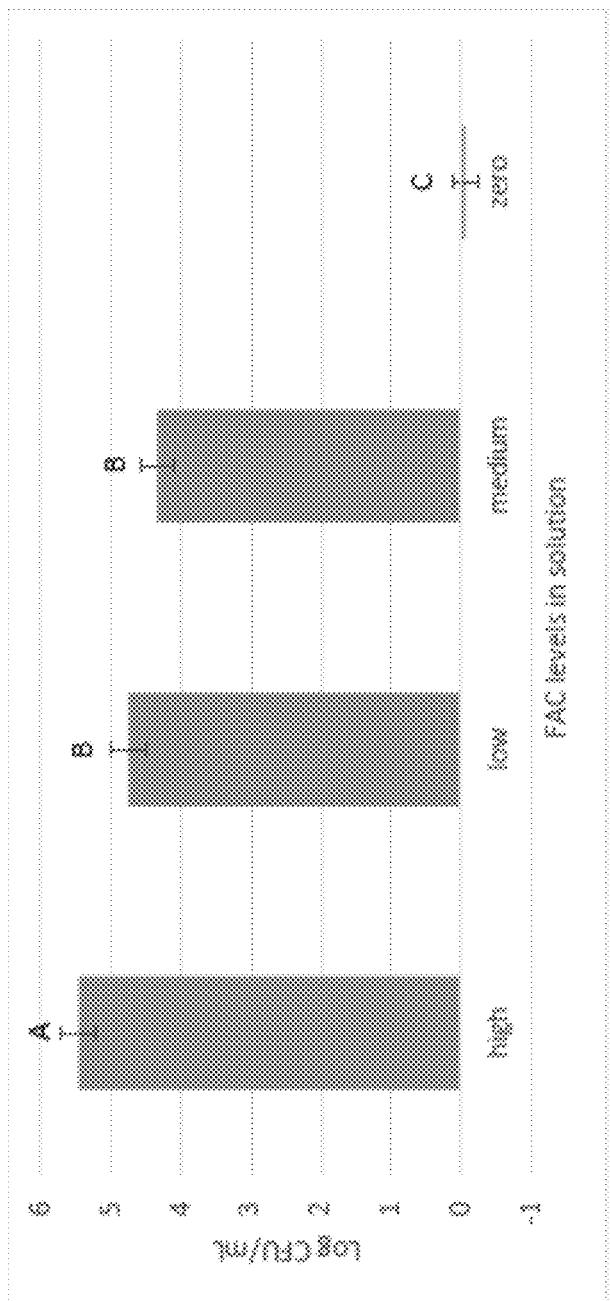
FIG. 6 shows Average Log CFU/mL Reductions Based on Level of FAC; A-C different letters indicate significant differences ($P \le 0.05$).

No lethality of STEC-7, surrogates, or *Salmonella* cocktail populations was observed in acidic or neutral pH solutions with or without nanobubble technology at 0 ppm FAC at either 1.7° C. or 5.6° C. This indicated that nanobubbles and/or pH alone were not the main contributor to microbial lethality (FIG. 6). Park, Hung, & Chung (2004) stated that the pH may not be important to the antimicrobial efficacy of EO water, an observation which was upheld in this preliminary study. Other studies have shown >7 log cycle reductions in *E. coli* O157:H7 and *Listeria monocytogenes* in EO water at 1 ppm FAC and pH 5 (Park et al., 2004). While EO water was the antimicrobial chlorine source in the nanobubble solutions tested in the current study, it was only present in small amounts, thus likely accounting for differences in effectiveness reported from previous research.

Conclusion

As the first part of a 3-part benchtop study, the goal of this experiment was to determine the minimum concentration of chlorine in combination with pH and nanobubbles as an effective antimicrobial against pure culture biological targets. This work demonstrated that chilled water containing FAC levels of approximately 12 ppm are highly effective as antimicrobials in the absence of organic loading, and that surrogates can be used as appropriate indicator organisms for STEC and *Salmonella* in chlorinated nanobubble solution applications. Low levels (approximately 3 ppm, the lowest level evaluated) of FAC in solution was still effective in reducing target organism populations in pure culture. Even lower levels of FAC could have been evaluated but were not due to the proposed applications of this antimicrobial technology in beef processing environments with high levels of organics present.

Although slightly acidifying the water to pH 5 and including nanobubbles did not definitively impact microbial reductions in pure culture, there is a possibility that these factors in conjunction with FAC will contribute to a less variable microbial kill in recirculating wash solutions and/or in the presence of organics (i.e., red water; evaluated in part 2) and beef lean and fat tissue (evaluated in part 3). Additionally, higher levels of FAC may be evaluated in nanobubble solutions depending on results from these subsequent studies.

1.2. Determining Lethality of Pathogens and Surrogates in the Presence of Red Water.

Chlorine is a long-standing and effective antimicrobial and sanitizing agent in the food industry; however, free available chlorine (FAC) level in solution, the indicator of sanitizing power, is dramatically affected by organic matter. This presents an interesting dilemma when considering applications of chlorine-based applications in a meat processing environment. Studies regarding the effect of chlorine on pathogen inactivation in the presence of organic materials (e.g., red water) is limited (Zhou, B., et al. (2015). Inactivation dynamics of *Salmonella enterica*, *Listeria monocytogenes*, and *Escherichia coli* O157:H7 in wash water during simulated chlorine depletion and replenishment processes. *Food Microbiology*, 50, 88-96). Understanding the lethality of antimicrobial components, especially chlorine, in organically-loaded water systems provides realistic insight into common food processing scenarios such as poultry chillers, produce wash solutions, and in this case, recirculating process waters used in a proprietary ground beef manufacturing process.

The two goals of this experiment were to 1) determine maximum beef purge level in Cesco-NAN-02 technology solutions whereby all free available chlorine in the nanobubble solutions is depleted, and 2) determine the effectiveness of chlorinated nanobubble solutions with added beef purge (i.e., red water) to reduce Shiga toxin-producing *E. coli* (STEC), *Salmonella* spp., and non-pathogenic surrogates over time.

Materials and Methods

Generation of Red Water Solutions

Cesco-NAN-02 technology water solutions were manufactured in Bellingham, Wash. and ground shipped to Kansas State University. All combinations of solutions components (FAC level, pH 5 or 7, and presence/absence of nanobubbles) were generated to serve as test treatments, as defined elsewhere herein). Chlorinated solutions formulated to contain nanobubbles were generated using municipal water infused with Aquaox 5000™ (Aquaox LL, Dillsburg, Pa., USA) to attain the target FAC levels between 0 and 40 ppm. If test solutions were to be acidified to pH 5, $CO_2$ gas was bubbled into the water prior to nanobubble generation. Cesco-NAN-02 technology water technology generates nanobubbles by passing water through a patented generator that uses cavitation chambers and shear planes to initiate an endothermic reaction thus producing high concentration of paramagnetic oxygen nanobubbles with a mean particle size between 50 and 100 nm (Bauer (2016) Nanobubbles from www.nanobubbles.com, Retrieved Oct. 3, 2016). Each shipment of solutions was evaluated in inoculated benchtop studies within 5 days of arrival at KSU and within 12 days of generation. Beef purge collected from stored vacuum packaged beef subprimals (obtained from the Kansas State University Meat Lab, Manhattan, Kans.) was added by percent volume (at varying purge levels as defined elsewhere herein) to simulate realistic red water levels likely to represent the proprietary commercial ground beef processing system evaluated in Example 2.

Preliminary Chlorine Loss Determination Resulting from Varying Levels of Purge Addition To quantify the impact of beef purge loading on FAC in 16 treatment combinations, Cesco-NAN-02 technology water manufactured to contain a wide range of FAC in solutions [zero ppm control, low (~3.5 ppm FAC), medium (~4.5 ppm FAC), medium-high (7-11 ppm FAC), high (20-26 ppm FAC)] and characterized as pH 5 or 7, and presence/absence of nanobubbles was evaluated.

Beef purge was initially added at a 5% target by volume to simulate an estimated maximum organic load in red water in a beef processing dip system. Aliquots (50 mL) of each solution combination of FAC level, acidity, and presence/absence of nanobubbles were contained in 125-mL glass Erlenmeyer flasks at 4° C. and continuously agitated at 140 rpm (Multi-Platform Shaker; Fisher Scientific, Pittsburgh, Pa., USA). FAC was measured using a portable photometer (Model HI96711, Hanna Instruments, Woonsocket, R.I.) before introduction of purge and at several time points (5, 28, 35, 58, and 65 min) after the introduction of purge. These agitated red water solutions were re-infused with fresh Cesco-NAN-02 technology water of the same composition as the original treatment solution (i.e. acidic nanobubble re-infused with acidic nanobubble, acidic no nanobubble re-infused with acidic no nanobubble), after 30 and 60 minutes of exposure.

This re-infusion process entailed removal of 10% 'used' solution immediately followed by addition of 10% fresh solution to help mimic the recirculating water in the proprietary commercial recirculating nanobubble water system.

This first organic loading experiment was conducted, only to find that the 5% purge addition completely eliminated any FAC in the Cesco-NAN-02 technology solutions. After discussion of the actual commercial system with the meat processor, it was determined that commercial circulating process water could be maintained at lower purge levels. In a follow-up experiment, stronger FAC solutions (20-26 ppm and ~30 ppm FAC) were obtained from Cesco-NAN-02 technology; solutions with lower FAC levels were not evaluated further due to the inability to maintain any level of residual FAC in the presence of beef purge. In this follow-up study, lower levels of beef purge (0 to 0.25% by volume, with increases at 0.05% intervals) were mixed with the two high FAC solution levels of Cesco-NAN-02 technology water and evaluated. Aliquots (50 mL) of each solution combination of chlorine level, acidity, and presence/absence of nanobubbles were contained in 125-mL glass Erlenmeyer flasks at 4° C. and continuously agitated at 140 rpm. FAC was measured using a portable photometer before introduction of purge and at several time points (1, 5, 25, 35, 45, or 65 minutes) after the introduction of purge. No re-infusions were done in order to determine how long residual FAC levels persisted in Cesco-NAN-02 technology red water solutions.

Bacterial Cultures and Inoculum Preparation

After gaining an understanding of the impact of varying levels of purge loading in the Cesco-NAN-02 technology solutions, an inoculated study was conducted to evaluate the antimicrobial effectiveness of organically loaded Cesco-NAN-02 technology waters. Rifampicin-resistant *E. coli* surrogates, rifampicin-resistant Shiga toxin-producing *E. coli*, and *Salmonella* serovars used in this study were propagated and prepared as described elsewhere herein.

Application of Chlorinated Water Treatments to Reduce Target Bacterial Populations in the Presence of 0.1% Red Water Aliquots (49.5 mL) of 33-40 ppm FAC, pH 5 Cesco-NAN-02 technology solutions representing each combination of presence/absence of nanobubbles were contained in 125-mL glass Erlenmeyer flasks at 4±3° C. and agitated at 140 rpm (Multi-Platform Shaker; Fisher Scientific, Pittsburgh, Pa.). Cesco-NAN-02 technology solutions were spiked with beef purge at a 0.1% by volume level to create red water. After approximately 1 min, red water solutions were inoculated with 0.5 mL (~9.7 log CFU/mL) of the 24-h culture cocktails individually—adjusting for the dilution effect of the initial test solution, the level of total organisms in solution was ~7.7 log CFU/mL. Cultures were exposed in the various solutions for 60 minutes with continuous shaking. Samples (5 mL) were taken after 1, 25, and 60 minutes (25 mL) of exposure to the red water/Cesco-NAN-02 technology solution and neutralized immediately with double-strength DE Neutralizing Broth. Red water solutions were re-infused with fresh Cesco-NAN-02 technology water, of the same composition as the original treatment solution, after 30 minutes of exposure by removing 10% of the 'used' solution and adding 10% of fresh solution to Two replications of the experiment were completed.

Microbial Analysis

Surviving populations of each target inoculum group were determined by plating serial dilutions in phosphate buffered saline (PBS) of each neutralized sample onto injury recovery and selective media agar plates as described in section 4.1.2.4. In cases where no viable cells were recovered, 5-7 mL of the original neutralized sample were transferred to either 100 mL TSB+rif or Rappaport-Vassiliadis Broth (RV; Difco, Becton, Dickinson and Company, Sparks, Md., USA) to enrich for STEC-7 or surrogates and *Salmonella* spp., respectively. All enrichments were incubated at 37° C. for 24 h and subsequently streaked onto either TSA+rif or XLD for qualitative detection of surviving organisms below the direct plating detection limit (0.3 log CFU/mL).

Results and Discussion

It is important to note that this section consists of data that has not been statistically analyzed and therefore should be considered preliminary. The purpose of this evaluation and the findings therein was to provide insight into the impact of organic materials (beef purge) on FAC levels in the Cesco-NAN-02 technology water treatments in order to plan for the subsequent in-plant validation studies (Example 2).

Preliminary Evaluation of Chlorine Loss

In the presence of any organic material, free chlorine in solution is lost rapidly. Yang and colleagues showed that an initial level of 35 ppm FAC is reduced to zero after only four lettuce dip washes; replenishing the solution with the same amount of NaClO as originally used only resulted in FAC restoration to levels between 7.2 and 17 ppm indicating that higher levels of NaClO is needed over time to maintain FAC in solution (Yang, Y., et al. (2012). Enhanced Chlorine Efficacy against Bacterial Pathogens in Wash Solution with High Organic Loads: Enhanced Chlorine Efficacy against Pathogens. *Journal of Food Processing and Preservation*, 36(6), 560-566). Measuring level of organic matter in recirculating water solutions is difficult based on inconsistency of initial organic loading on product and constant changes in water properties.

Figure 7:
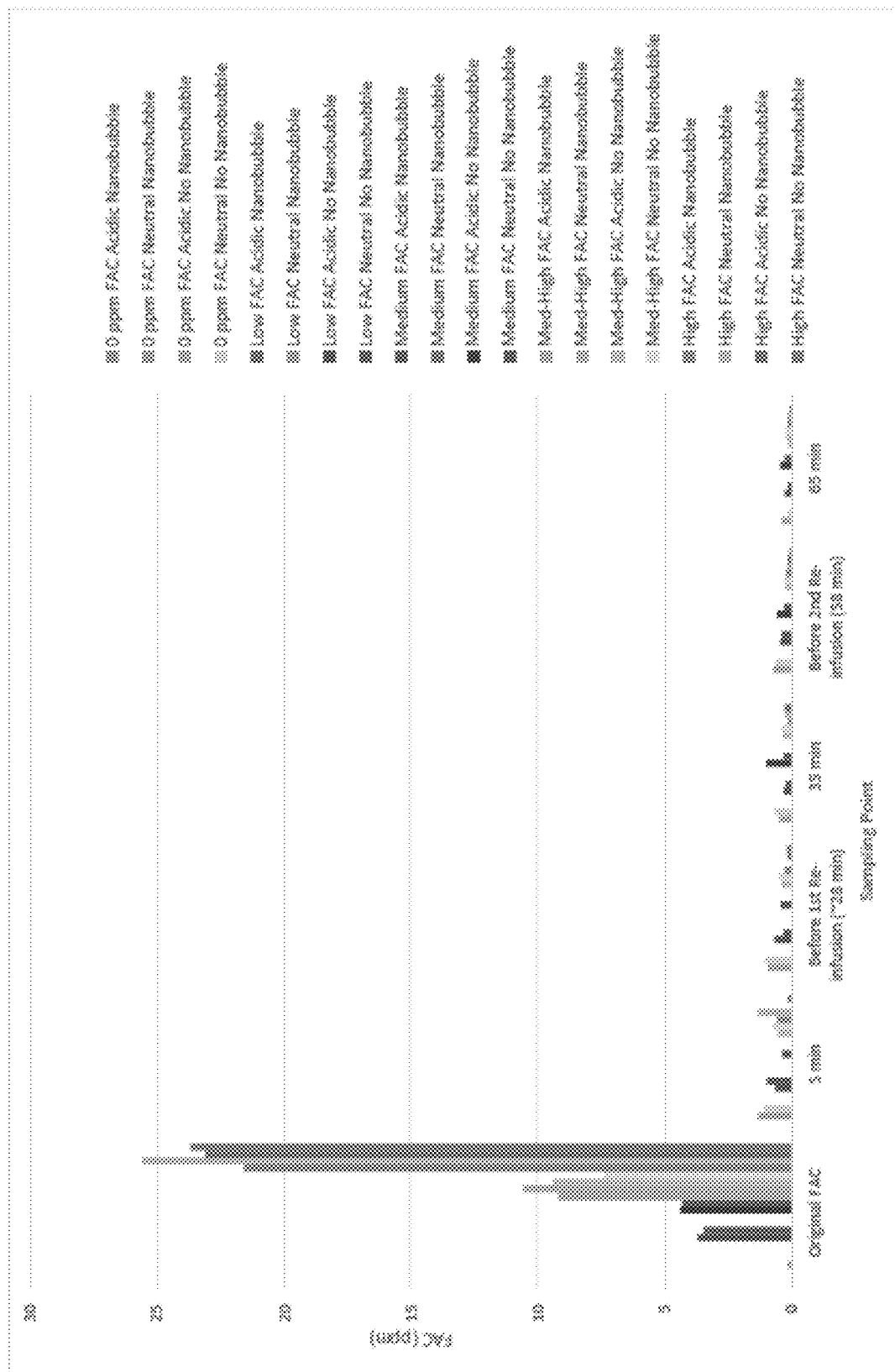
FIG. 7 shows Residual Free Available Chlorine after Addition of 5% Purge to Cesco-NAN-02 technology Water Solutions.

During the preliminary trial, purge was initially added at 5% by volume to Cesco-NAN-02 technology solutions as the estimated maximum level of anticipated purge-to-water in a novel beef processing dip/immersion system to be evaluated in subsequent commercial in-plant studies. It was determined quickly that 5% purge completely inactivated all FAC present in a wide range of solutions [zero, low (~3.5 ppm FAC), medium (~4.5 ppm FAC), medium-high (7-11 ppm FAC), high (20-26 ppm FAC)] even with reinfusion of new Cesco-NAN-02 technology water (FIG. 7). Once it became apparent that the research team could not maintain levels of FAC even at the high initial levels, stronger solutions (i.e. 30 ppm FAC) were obtained for subsequent studies. The first experiment (depicted in FIG. 7) demonstrated that chlorine solutions with initially low levels of FAC could not be maintained; only high FAC solutions were used in subsequent chlorine demand experiments.

Figure 8:
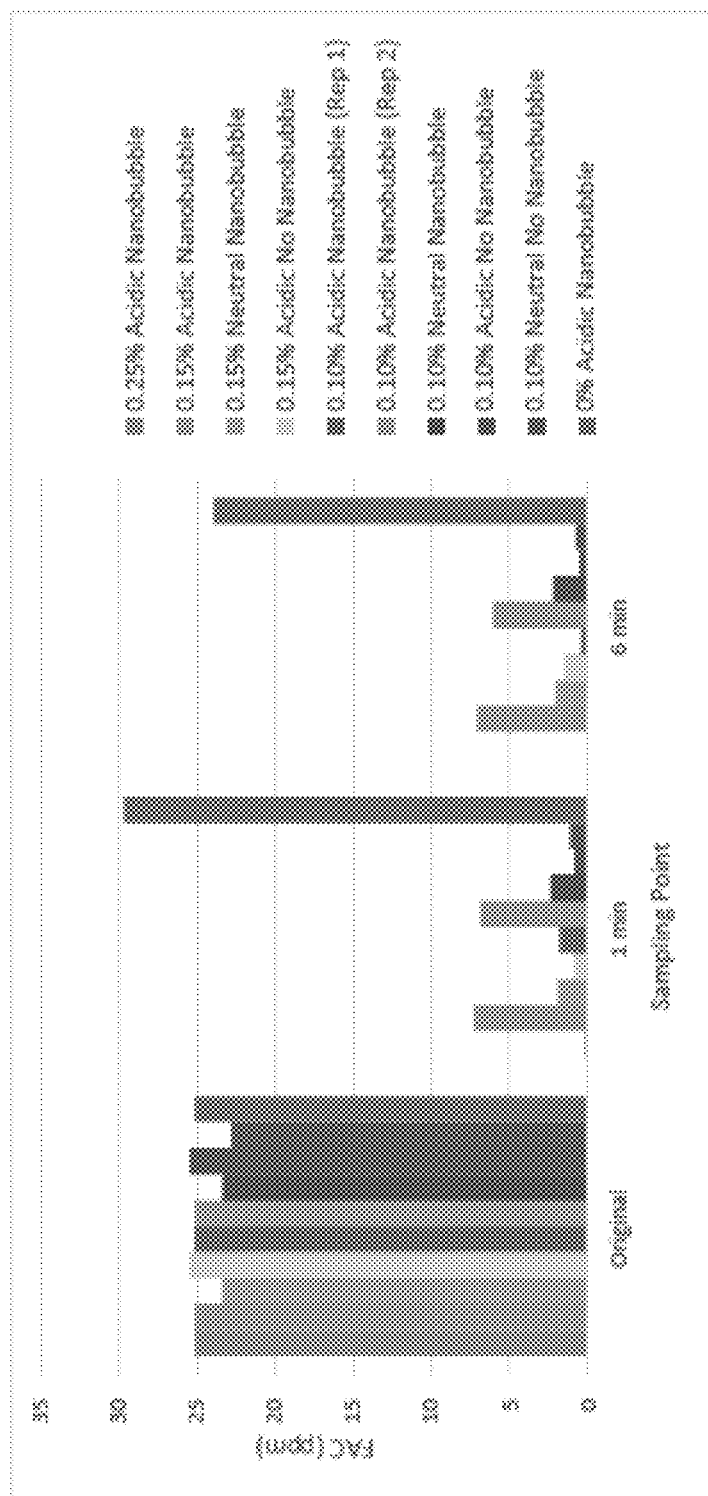
FIG. 8 shows Residual Free Available Chlorine after Purge Addition (0-0.25%) to 25 ppm FAC Cesco-NAN-02 technology Water Solutions.
Figure 9:
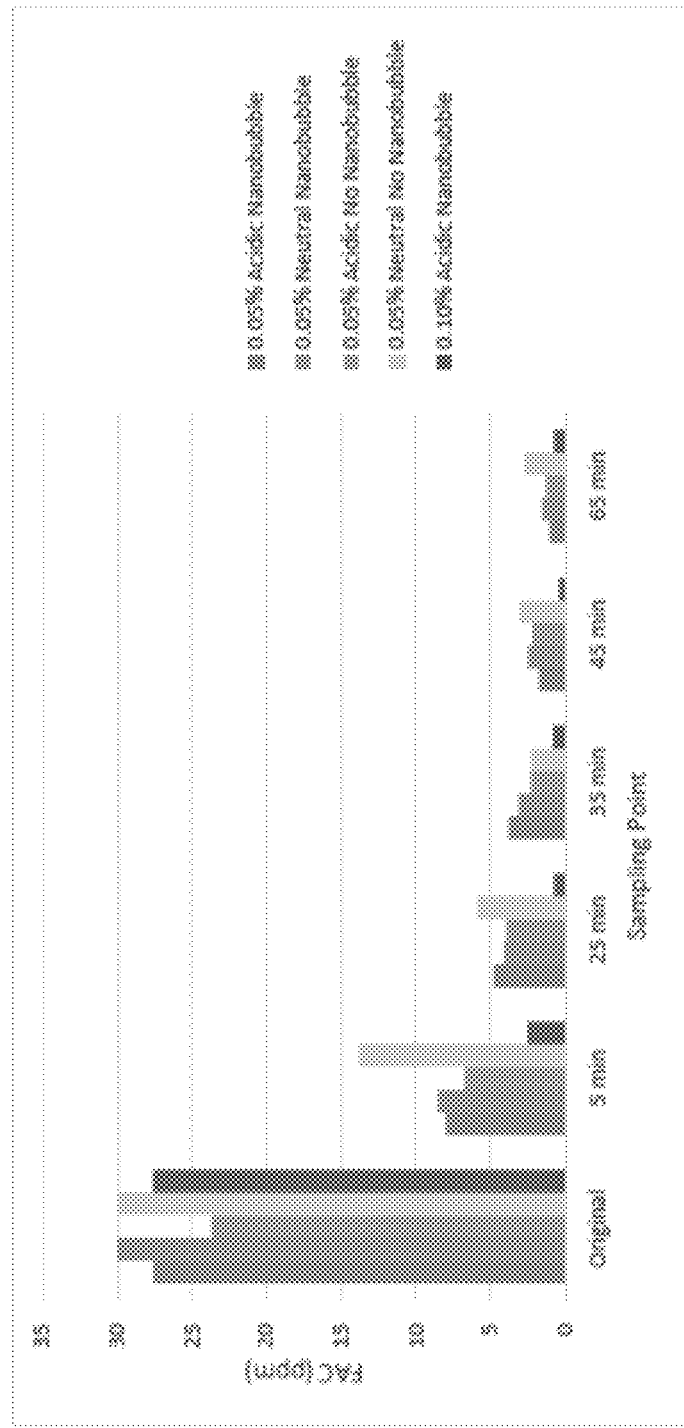
FIG. 9 shows Residual Free Available Chlorine after Purge Addition (0.05-0.10%) to 23-30 ppm FAC Cesco-NAN-02 Water Solutions with No Re-infusion of Fresh Solution.
Figure 10:
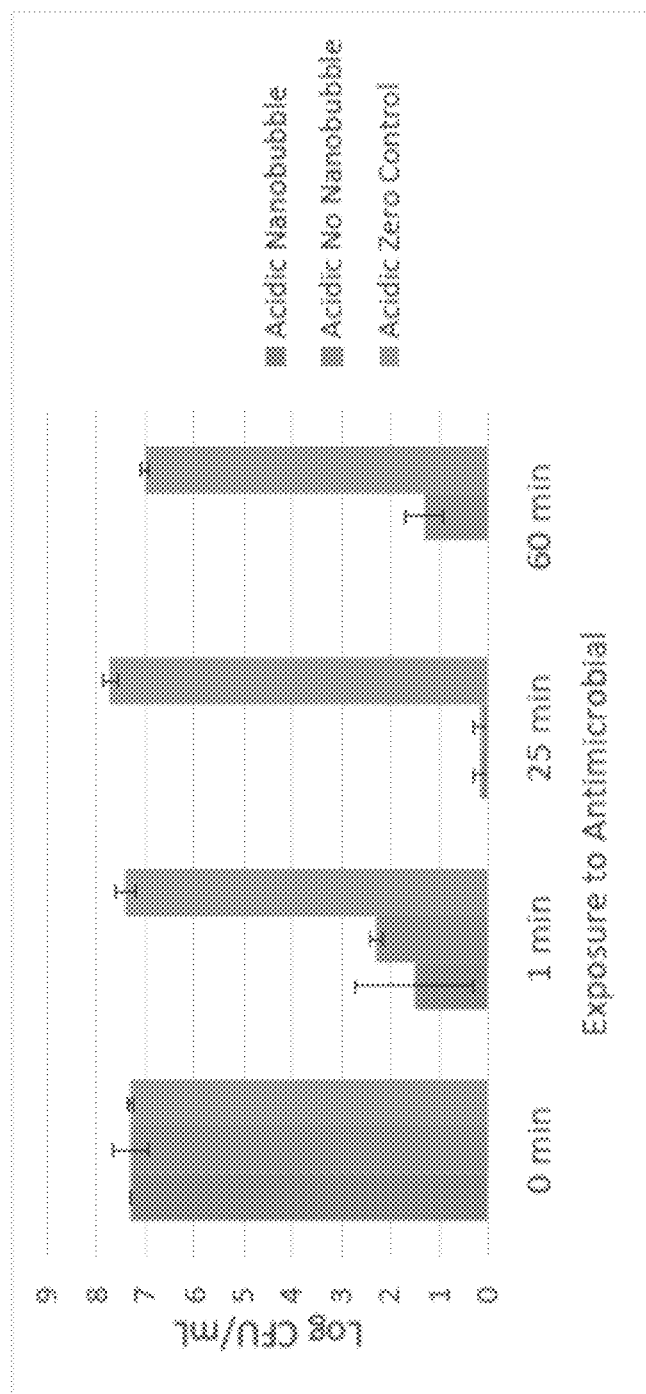
FIG. 10 shows Average Recovery of Surrogates After Exposure to Red Water for 60 min in the Presence of 0.1% Purge on Injury Recovery Media.
Figure 11:
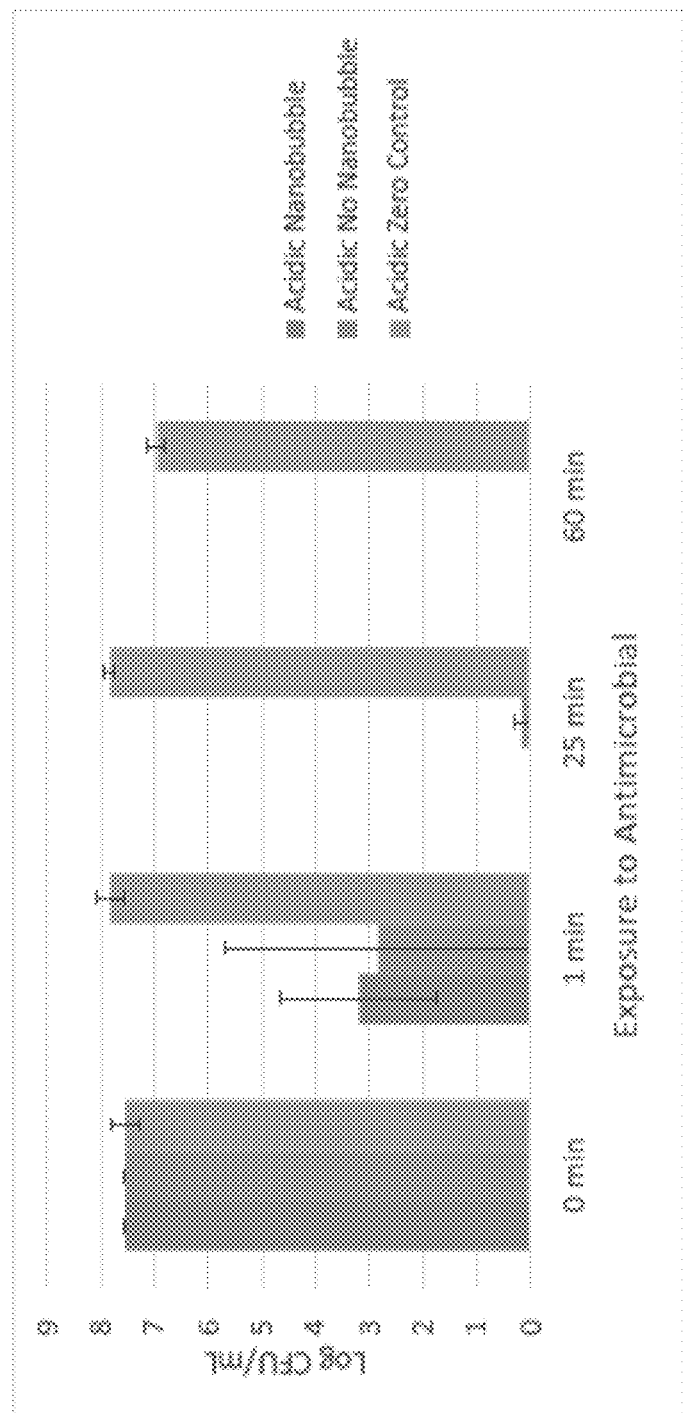
FIG. 11 shows Average Recovery of STEC-7 After Exposure to Red Water for 60 min in the Presence of 0.1% Purge on Injury Recovery Media.
Figure 12:
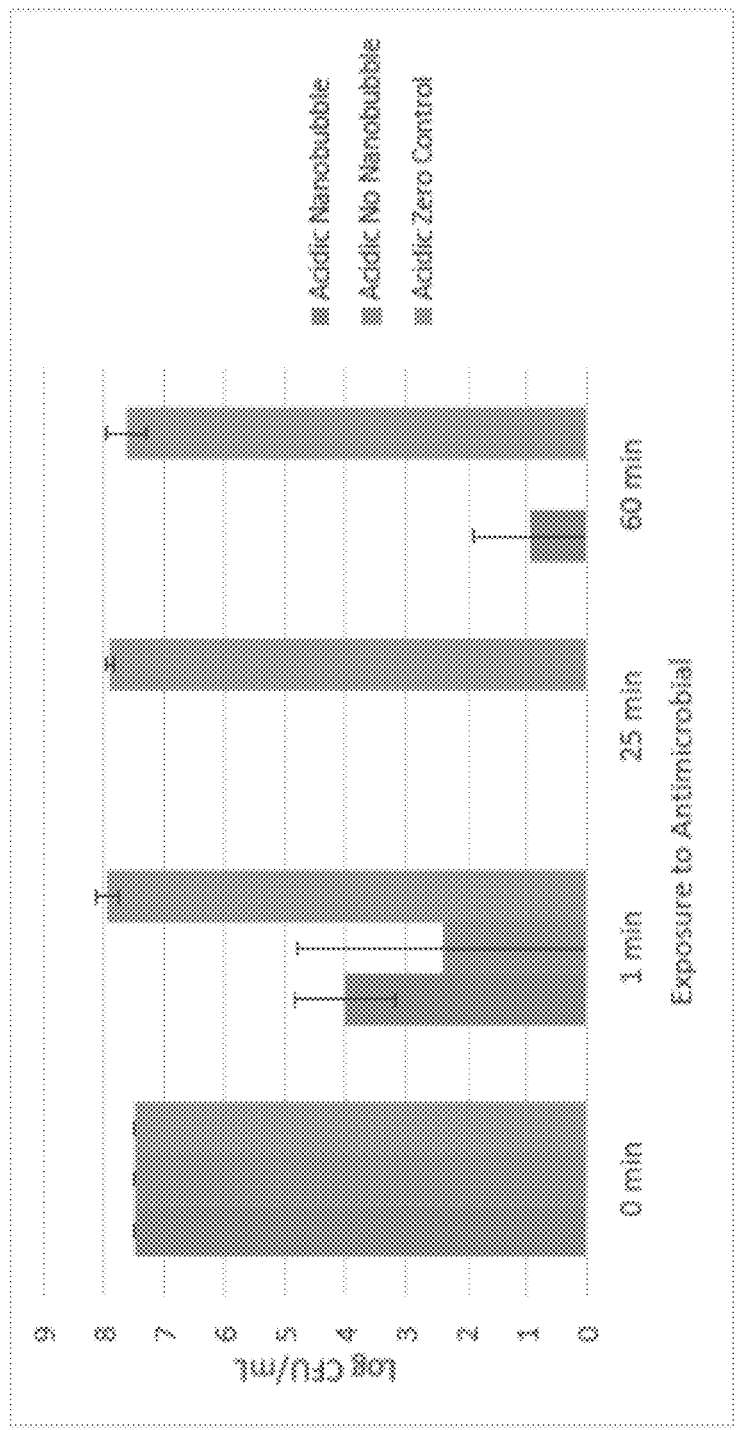
FIG. 12 shows Average Recovery of *Salmonella* After Exposure to Red Water for 60 min in the Presence of 0.1% Purge on Injury Recovery Media.

To determine the maximum level of purge that could be added before completely inactivating free chlorine in the Cesco-NAN-02 technology solutions, lower concentrations of purge were added to high FAC Cesco-NAN-02 technology water solutions (24.66±0.97 ppm) and monitored for a total of six minutes without re-infusion (FIG. 8). From these results, it was determined that 0.1% beef purge red water solutions or lower should be evaluated in the microbial inactivation study, as FAC was bound at all purge levels higher. This test also indicated that FAC is bound very quickly thus prompting a second test of evaluating FAC levels over 1 hour to determine the extent of residual chlorine levels in solution with no re-infusions (FIG. 9). A control (0% purge) was also included.

Eventually, ~30 ppm FAC Cesco-NAN-02 technology water solutions were generated in Bellingham, Wash., shipped, and received by the Kansas State University Food Safety and Defense Laboratory. To determine how long residual FAC lingered in solution, 0.05 and 0.1% beef purge was added to ~30 ppm FAC and monitored for 60 minutes. It was determined that a maximum level of 0.05% purge with an initial level of 27.78±2.31 ppm free chlorine creates a red water solution that maintains residual levels of chlorine (~1 ppm) after 1 hour of exposure without re-infusion (FIG. 9).

Understanding the loading and effect of organic matter on chlorine loss in solution allows processors to determine recirculating water requirements and levels of chlorine-based antimicrobial needed to consistently maintain bactericidal levels in process water.

Pathogen Survival

Based on the results from the chlorine demand experiments, higher levels FAC in initial solutions were obtained (~35 ppm FAC) and utilized in this experiment. Only acidic (pH 5) solutions were evaluated. Due to the use of a slightly stronger FAC Cesco-NAN-02 technology water, 0.1% purge was evaluated instead of 0.05% purge to mimic a 'worst-case-scenario' organically loaded red water. Zhou and colleagues determined that a minimum FAC level of 3.66 ppm at 5.12 pH in a recirculating produce wash water system, similar to red water, was sufficient to reduce *Salmonella, E. coli*, and *L. monocytogenes* by 6 log cycles after a 30 second contact time (Zhou, B., et al. (2015). Inactivation dynamics of *Salmonella enterica*, *Listeria monocytogenes*, and *Escherichia coli* O157:H7 in wash water during simulated chlorine depletion and replenishment processes. *Food Microbiology*, 50, 88-96). Lethal levels of FAC were present in both the nanobubble and no nanobubble red water solutions during the initial exposure (1 min); however, levels of FAC were slightly higher in the no nanobubble solutions (Table 3), although there was no apparent difference in lethality of target organisms in nanobubble versus no nanobubble solutions. In the presence of 0.1% purge red water solutions, the surrogates, STEC-7, and *Salmonella* spp. were reduced by ~5 log CFU/mL, ~4.8 log CFU/mL, and ~4 log CFU/mL, respectively after 1 minute. After 60 minutes exposure to Cesco-NAN-02 technology solutions, and one re-infusion at 35 minutes, STEC-7 populations were completely eliminated as determined by enrichment, whereas surrogates and *Salmonella* exhibited slightly higher resistance and were still recovered at 1.3 log CFU/mL or less. It has been argued that time exposure does not necessarily enhance the reduction of target organisms (Stopforth, J. D., et al. (2008). Effect of Acidified Sodium Chlorite, Chlorine, and Acidic Electrolyzed water on *Escherichia coli* O157:H7, *Salmonella*, and *Listeria monocytogenes* Inoculated on Leafy Greens. *Journal of Food Protection*, 71(3), 625-628). However, this study indicates that the populations of target organisms decreased over time. As predicted, no lethality was observed in control solutions containing no nanobubbles and 0 ppm FAC over 60 minutes, with a solution re-infusion at 35 minutes.

TABLE 3

Level of Free Available Chlorine (ppm) in Each Solution During 0.1% Purge Experiment at Each Sampling Point.

|  |  | Nanobubble | No Nanobubble | Control |
|---|---|---|---|---|
| STEC | Initial Level | 33.75 ± 1.25 | 40.25 ± 0.75 | 0 |
|  | 1 min | 5.64 ± 1.56 | 10.19 ± 6.01 | 0 |
|  | 25 min | 0.535 ± 0.225 | 0.94 ± 0.40 | 0 |
|  | 35 min (after re-infusion) | 1.4 ± 0.77 | 2.7 ± 1.50 | 0 |
|  | 60 min | 0.84 ± 0.52 | 1.655 ± 0.98 | 0 |
| Surrogates | Initial Level | 33.75 ± 1.25 | 40.25 ± 0.75 | 0 |
|  | 1 min | 4.91 ± 1.21 | 11.03 ± 5.17 | 0 |
|  | 25 min | 0.34 ± 0.05 | 0.855 ± 0.45 | 0 |
|  | 35 min (after re-infusion) | 1.335 ± 0.35 | 2.205 ± 0.35 | 0 |
|  | 60 min | 0.57 ± 0.29 | 1.435 ± 0.71 | 0 |
| *Salmonella* | Initial Level | 33.75 ± 1.25 | 40.25 ± 0.75 | 0 |
|  | 1 min | 3.09 ± 0.45 | 9.26 ± 2.34 | 0 |
|  | 25 min | 0.19 ± 0.09 | 0.565 ± 0.15 | 0 |
|  | 35 min (after re-infusion) | 0.635 ± 0.21 | 2.555 ± 0.48 | 0 |
|  | 60 min | 0.385 ± 0.12 | 0.85 ± 0.12 | 0 |

Conclusion

When the target organisms were exposed to 3.09-11.03 ppm FAC solutions for 60 seconds, populations were notably reduced by 4-5 log CFU/mL in 0.1% red water. Although statistical analysis was not completed for this preliminary research, we can determine that the surrogate organisms act similarly to STEC-7 and *Salmonella* spp. in the presence red water, thus confirming the 5-strain surrogate cocktail to be an appropriate indicator for both target pathogens.

1.3 Efficacy of Chlorinated Nanobubble Solutions on Beef Lean and Fat in the Presence of Red Water.

Chlorine has proven to be an effective antimicrobial and sanitizing agent in the food industry; however, the level of free available chlorine (FAC), the indicator of sanitizing power, is dramatically affected by the presence of organic matter. This presents an interesting dilemma in a beef processing environment. Little research has been reported with chlorine on beef tissues, especially in a processing water dip scenario. Previous benchtop research reported above determined the effectiveness of low levels of FAC in chlorinated nanobubble red waters against target organisms, but has not evaluate the effectiveness of these solutions for reducing microbial population levels on the surface of lean and fat tissues.

The primary goal of this experiment was to characterize the lethality of chlorinated nanobubble (i.e. Cesco-NAN-02 technology solution) red water against Shiga toxin-producing *E. coli* (STEC), select *Salmonella serovars*, and non-pathogenic surrogates on the surface of "shattered" lean and fat beef tissue (the preparation of "shattered" lean and fat is described in Chapter 5). The secondary goals of this experiment were to 1) determine the level of water contamination and length of time pathogens persist in recirculating ground beef processing water (mimicking the proprietary commercial processing system), and 2) determine the level of contamination picked up by non-inoculated meat entering the system following inoculated meat exposure. The experiment consisted of one red water container per organism cocktail held and treated for 6 continuous days to simulate the operational parameters of a novel proprietary ground beef manufacturing process (profiled in Example 2).

Materials and Methods

Meat Source

Fifty pounds each of 'shattered' lean and fat pieces were obtained from the commercial beef processor (Clackamas, Oreg., USA) and frozen at 0° C. until use. Approximately 500 g of lean or fat was thawed daily at 4° C. 18 to 24 hours prior to use. The 'shattered' lean and fat pieces are created by crust-freezing course ground (through a ¾" inch plate) 50/50 lean/fat in a liquid-nitrogen tunnel, and passing the crust frozen meat through two smooth metal rollers that "shatter" the meat into smaller pieces (see detailed process description in Example 2).

Bacterial Cultures and Inoculum Preparation

The rifampicin-resistant *E. coli* surrogates, rifampicin-resistant STEC strains, and *Salmonella serovars* used in this study were propagated and prepared as described in section 4.1.2.1; except the centrifuged culture cocktails were rehydrated in 90 mL of phosphate buffered saline (PBS).

Samples (100 g) of lean and fat tissues were mist-inoculated with 5-7 mL of rehydrated target culture cocktails (~7.5 log CFU/mL) individually and allowed to attach at 4° C. overnight (approximately 24 hours) before use. The same culture cocktails were used to inoculate lean and fat pieces throughout the experiment. Rehydrated cocktails were stored at 4° C. throughout the duration of the experiment.

Antimicrobial Water Solutions

Cesco-NAN-02 technology water adjusted to pH 5 and 38.5 ppm FAC was generated in Bellingham, Wash. and was ground shipped to the Kansas State University Food Safety and Defense Laboratory. This shipment was used within 18 days of production, and utilized throughout the 6-day experiment as the initial water solution to prepare red water, and for solution re-infusions throughout the experiment. pH was manually adjusted at the K-State laboratory by bubbling small amounts of $CO_2$ gas into the stored Cesco-NAN-02 technology solutions at the beginning and middle of the experiment (Day 1 and Day 4) to maintain pH 5 in the original Cesco-NAN-02 technology water.

Experimental Procedure

One liter of 38.5 ppm FAC, pH 5 Cesco-NAN-02 technology water was added to three sterilized, sealable plastic containers (Rubbermaid, Atlanta, Ga.) individually—one container for each organism cocktail—and stored in a 4° C. walk-in cooler for the duration of the 6-day experiment. 0.1% by volume beef purge was added to each container to create red water. Every 6 hours, red water solutions were re-infused with fresh 38.5 ppm, pH 5 Cesco-NAN-02 technology water; 10% 'used' solution was removed and 10% fresh solution was added to mimic recirculating water in the commercial processing system. The red water solutions were also re-infused following each introduction of non-inoculated meat twice daily.

Refrigerated lean (25 g) and fat (25 g) portions that had been inoculated 24 h previously were combined and dropped into each container at the beginning of the day, every other day—Days 1, 3, and 5. Each container was manually agitated to stimulate a laminar flow scenario.

Lean and fat tissues were exposed to the red water antimicrobial solutions for ~60 seconds and then removed with a sterilized metal strainer. The lean and fat tissues were separated from each other using sterilized metal spoons, with components weighed into separate filtered stomacher bags (Seward, United Kingdom) containing 100 mL DE broth. Refrigerated non-inoculated lean (25 g) and fat (25 g) was similarly introduced into the container, exposed for ~60 seconds, and removed (as described above) twice daily, 15 and 45 minutes after the inoculated meat removal, to determine pick-up of surviving organisms. Non-inoculated meat was added again to the containers to determine pick-up of surviving organisms 24 hours later—Days 2, 4, and 6.

Red water samples (5 mL) were collected each time meat was introduced into the container, both inoculated and non-inoculated, and every 6 hours prior to re-infusion of new solution to determine surviving levels of target organisms in solution. FAC, pH, and ORP was measured for each water sample collected (HI96711 Portable Photometer, Hanna Instruments, Woonsocket, R.I., USA; PT3 and PT4 pens, Myron L Company, Carlsbad, Calif., USA). Due to the nature of a continuously re-infused solution, replications are differentiated by inoculation day with reps defined as Day 1 and 2, Day 3 and 4, and Day 5 and 6 for a total of three replications.

Microbial Analysis

Meat Samples—Portions (25 g) of lean or fat were added to filtered stomacher bags containing 100 mL DE broth, stomached (Smasher™, bioMerieux, Hazelwood, Mo., USA) for 60 seconds, and serially diluted with PBS. To enumerate surviving *Salmonella* populations, dilutions were spread plated on XLD agar incubated for 24 hours at 37° C., or on TSA that was incubated for 6 hours at 37° C. and followed by overlaying with XLD with additional incubation for 12-18 h at 37° C. To enumerate rifampicin-resistant surrogates and STEC-7 on selective media, 10 mL of the original homogenized sample (25 g meat+100 mL DE broth) was removed from the original bag and added to 0.1 g/L rif and serially diluted using PBS blanks containing 0.1 g/L rif (PBS+rif). Dilutions were plated on *E. coli*/coliform Petrifilm (ECC; 3M Corporation, Saint Paul, Minn., USA), and incubated at 37° C. for 24 hours. To determine injury recovery of rif-resistant surrogates and STEC-7, samples were diluted with PBS blanks, spread plated on TSA and incubated for 6 hours at 37° C., overlayed with TSA+rif, and incubated for 12-18 additional hours at 37° C.

Water Samples—Red water aliquots (5 mL) were pipetted directly into a test tube containing 5 mL DE broth, manually mixed for 60 seconds, serially diluted with PBS, and spread plated on XLD agar that was incubated for 24 hours at 37° C. to detect *Salmonella* spp. Additionally, to detect injured *Salmonella* cells, the dilutions were spread plated onto TSA incubated for 6 hours at 37° C., subsequently overlayed with XLD, and incubated for 12-18 additional hours at 37° C. To enumerate rifampicin-resistant surrogate population and STEC-7 on selective media, 2 mL of the original homogenized water sample (5 mL water+5 mL DE broth) was removed from the tube and added to 0.1 g/L rif, serially diluted with PBS blanks containing 0.1 g/L rif (PBS+rif), plated on *E. coli*/coliform Petrifilm (ECC; 3M Corporation, Saint Paul, Minn., USA), and incubated at 37° C. for 24 hours. To enumerate injured populations of rif-resistant surrogates and STEC-7, samples were diluted using PBS blanks, spread plated on TSA, incubated for 6 hours at 37° C., overlayed with TSA+rif, and incubated for 12-18 additional hours at 37° C.

Due to time and labor constraints, enrichments were not completed on any samples that tested negative by direct plating protocol (detection limit for water samples 0.3 log CFU/mL, meat samples 0.7 log CFU/g).

Results and Discussion

It is important to note that this section consists of data that has not been statistically analyzed and therefore should be considered preliminary. The purpose of this evaluation and the findings therein was to provide insight into the effectiveness of Cesco-NAN-02 technology solutions loaded with 0.1% beef purge (i.e., red water) treatments to help plan for the subsequent in-plant commercial validation studies described in Example 2.

Free Available Chlorine, pH, and ORP of Red Water Solutions

Figure 13:
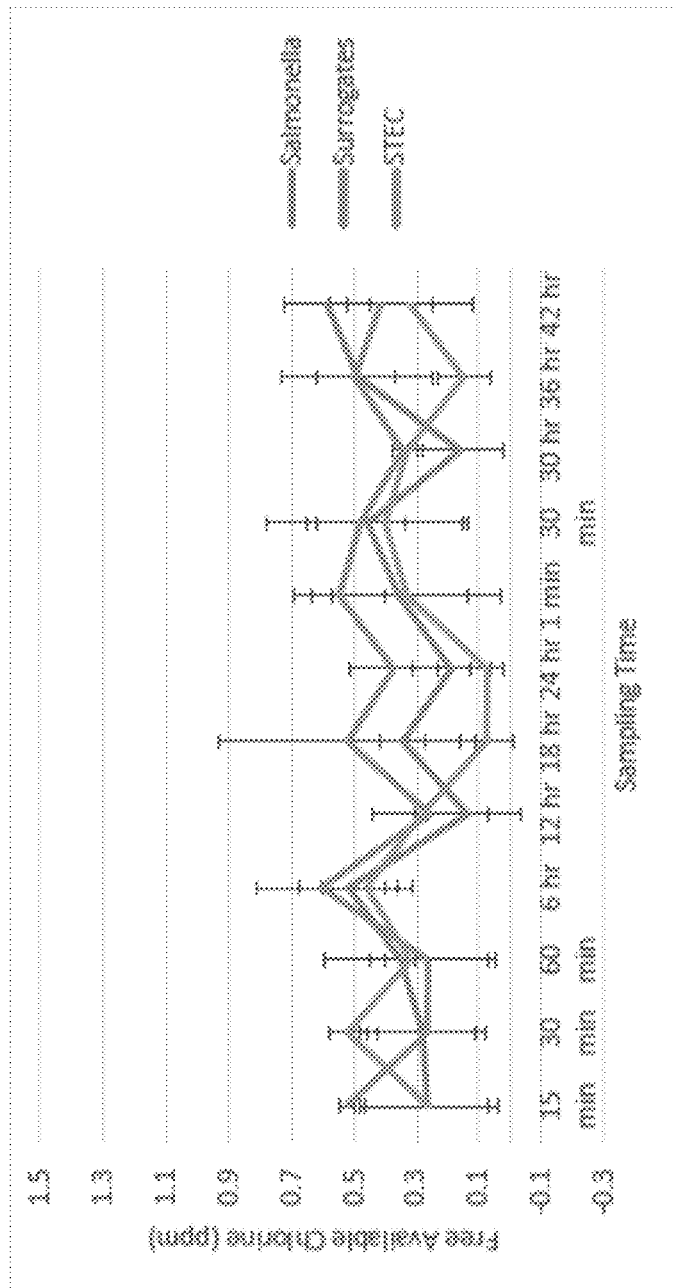
FIG. 13 shows Average Free Available Chlorine in Red Water over 42 hours.
Figure 14:
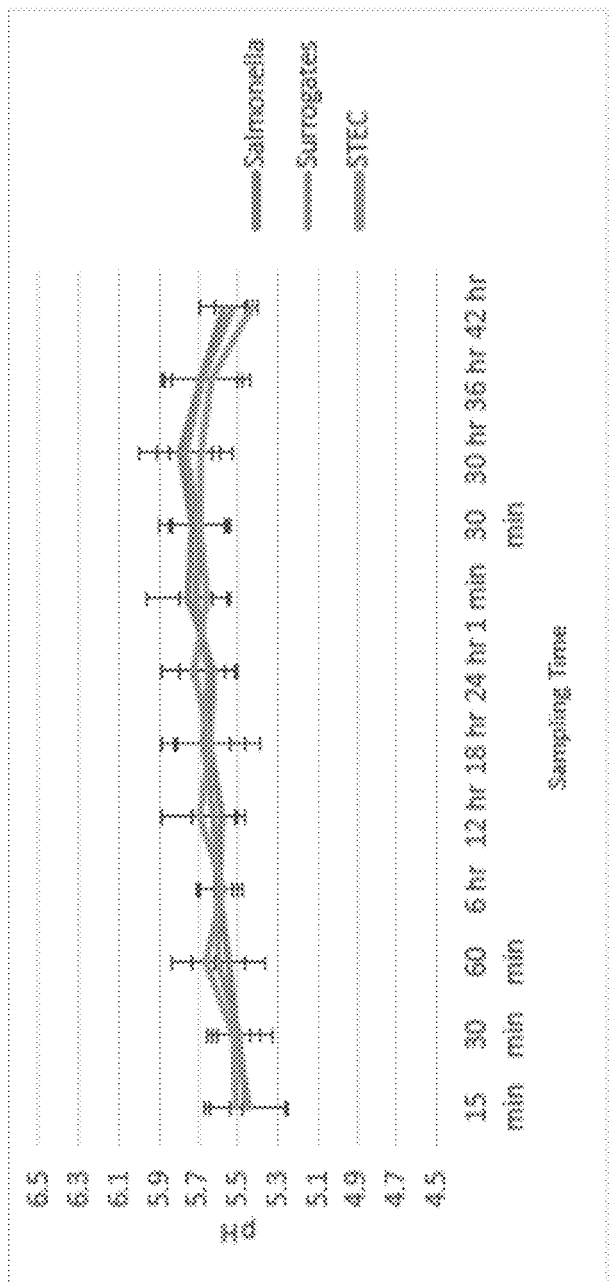
FIG. 14 shows Average pH of Red Water over 42 hours.
Figure 15:
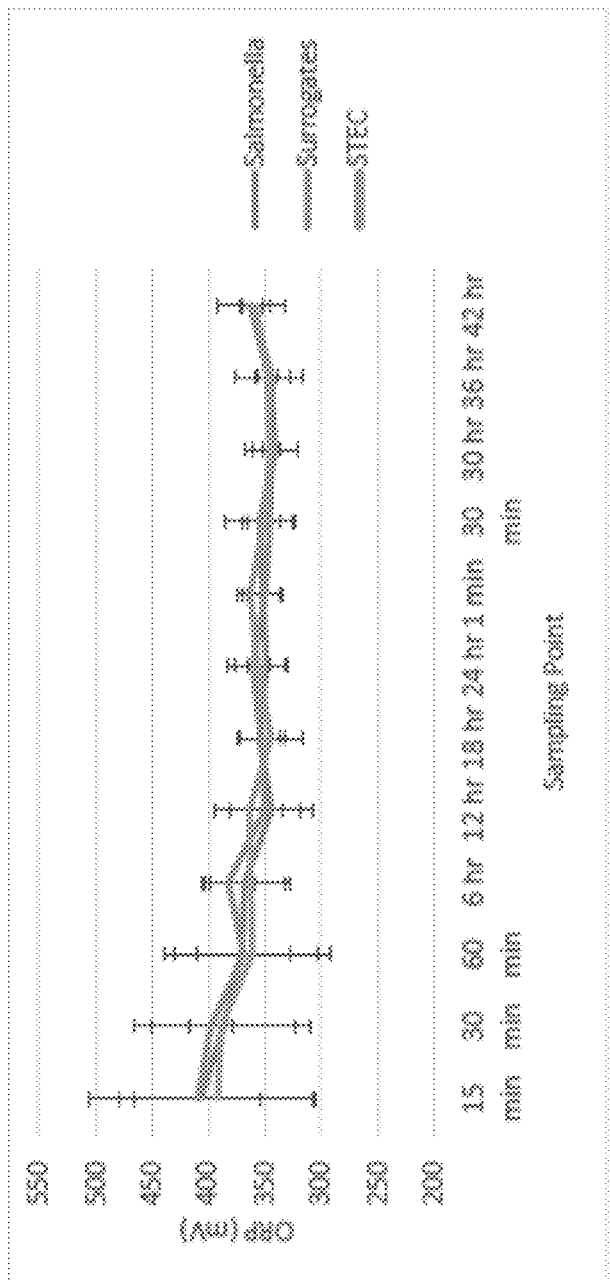
FIG. 15 shows Average ORP of Red Water over 42 Hours.

The original Cesco-NAN-02 technology water consisted of 38.5 ppm FAC, 5.03 pH, and 833 mV ORP. The FAC in the solutions dropped considerably to 13.87±1.09 ppm after the introduction of 0.1% by volume beef purge; pH and ORP did not change. However, once meat entered the system 15 minutes after purge addition, the properties of the water changed dramatically; FAC levels dropped below 1 ppm (FIG. 13), pH increased to 5.7 (FIG. 14), and ORP decreased to 350 mV (FIG. 15) and stayed at these levels throughout the duration of the experiment despite re-infusion of fresh Cesco-NAN-02 technology water solution every 6 hours.

Pathogen Recovery in Water Samples

Figure 16:
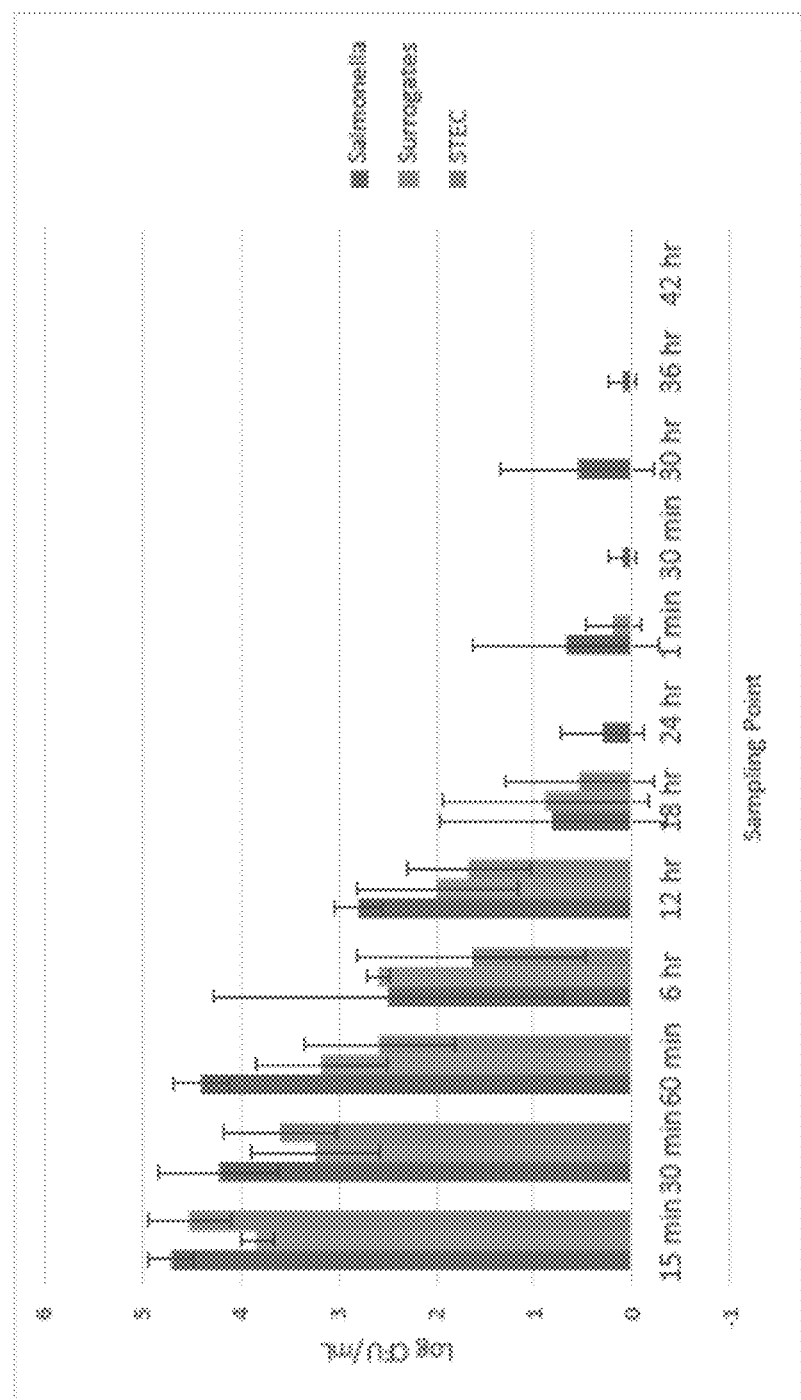
FIG. 16 shows Average Recovery of Organisms in Red Water over 42 Hours on Injury Recovery Media.
Figure 17:
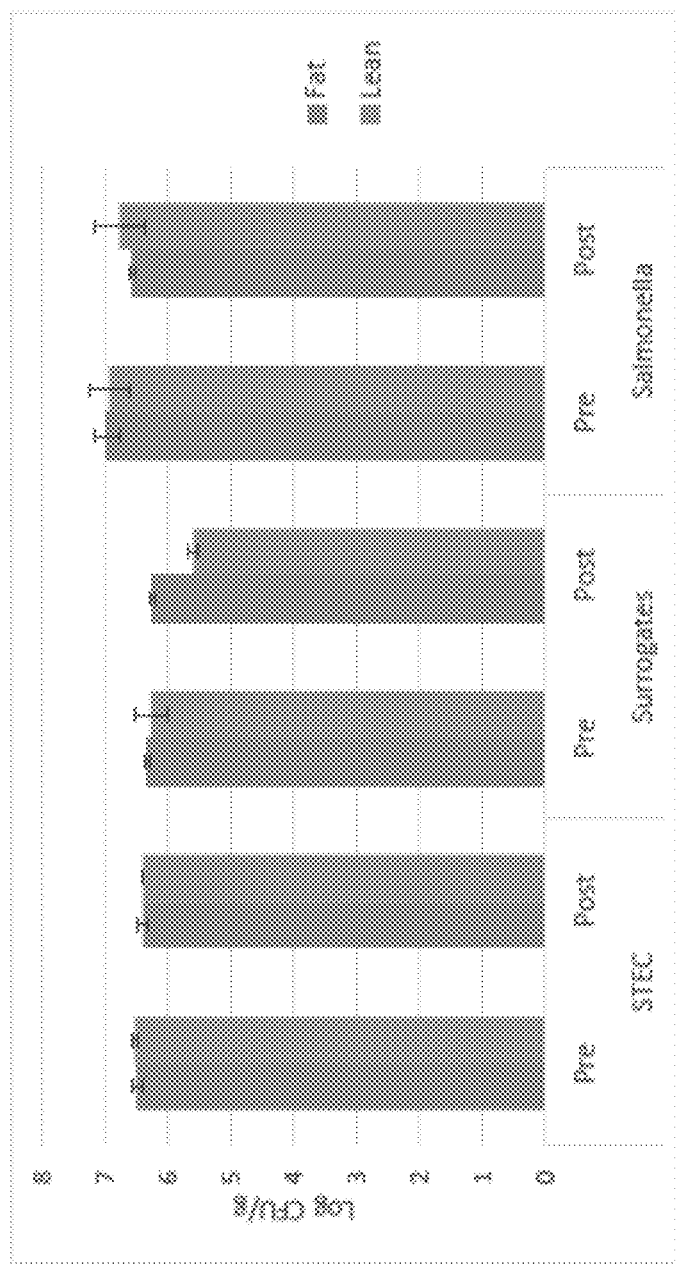
FIG. 17 shows Average Recovery of Organisms on Inoculated Meat Before and After ~60 second Exposure to the Antimicrobial Red Water on Injury Recovery Media.
Figure 18:
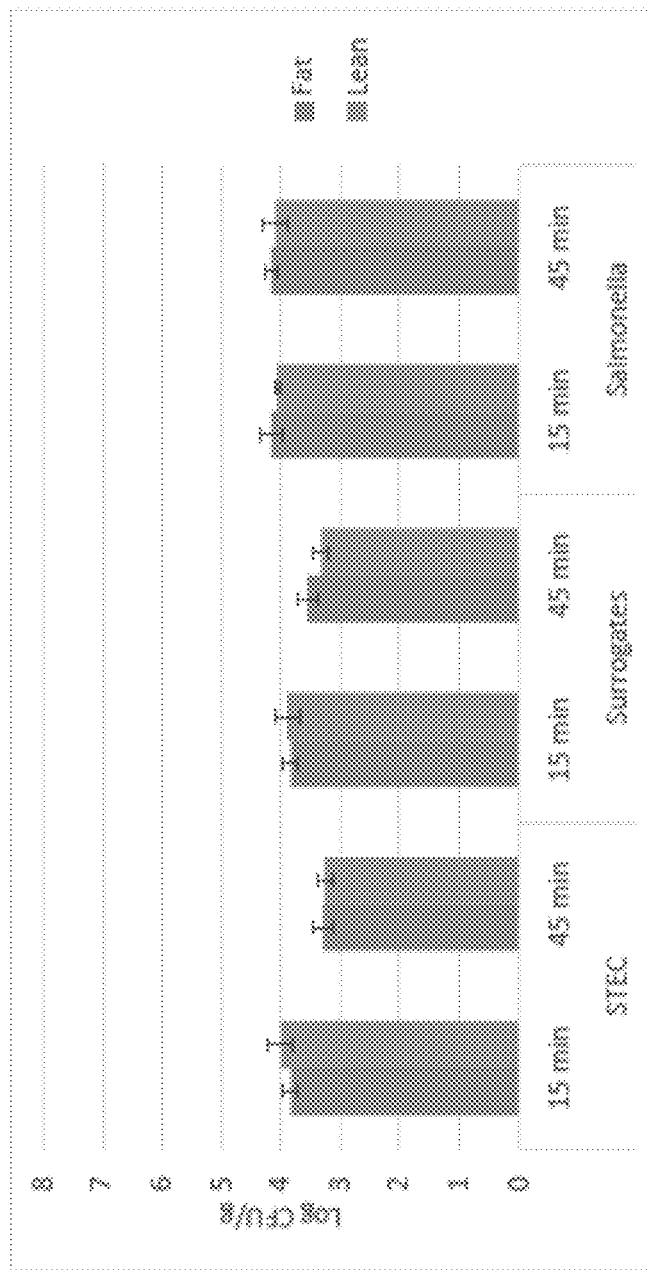
FIG. 18 shows Average Recovery on Non-Inoculated Pick-Up Meat Introduced into the System 15 and 45 minutes after Inoculated Meat on Injury Recovery Media.
Figure 19:
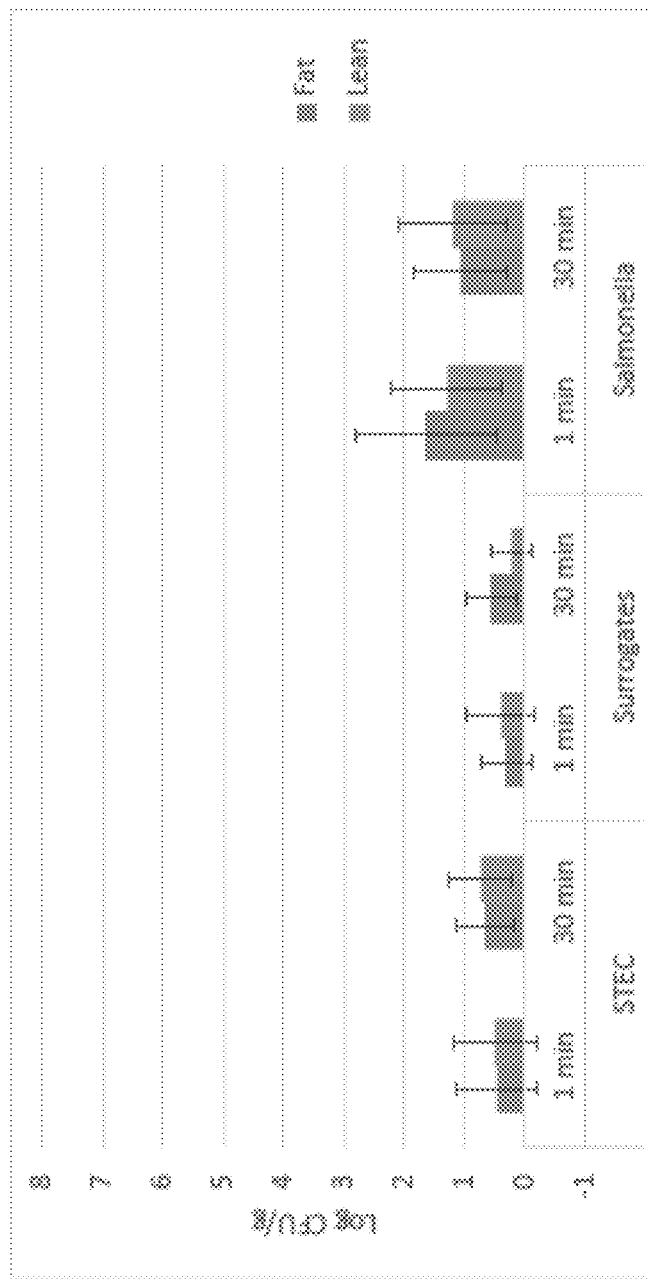
FIG. 19 shows Average Recovery of Target Organisms on Non-Inoculated Meat Introduced to Red Water 24 hours after Inoculated Meat on Injury Recovery Media.

Zhou and colleagues determined that a minimum FAC level of 3.66 ppm at pH 5.12 to 6.97 in a recirculating produce wash water system was sufficient to reduce *Salmonella*, *E. coli*, and *Listeria monocytogenes* by 6 log cycles after a 30 second contact time (Zhou, B., et al. (2015). Inactivation dynamics of *Salmonella enterica*, *Listeria monocytogenes*, and *Escherichia coli* O157:H7 in wash water during simulated chlorine depletion and replenishment processes. *Food Microbiology*, 50, 88-96). As reported in section 4.3.3.1, the levels of FAC and ORP were not effectively maintained to have an antimicrobialeffect on STEC-7, *Salmonella*, or surrogates within the 60 seconds of initial exposure. However, in the presence of proteins, chlorine will form chloramines and retain some level of antimicrobial effect even when FAC is reduced to unmeasurable concentrations. Block (1991) reported 100% reductions of *Salmonella pullorum* in a 130 ppm hypochlorite solution with 5% organic matter, although there was no measurable level of FAC. This demonstrated the sanitizing capacity of chloramines. It is likely that the initial (38.5 ppm) level of chlorine did not form chloramines at a bactericidal level in this experiment. pH was maintained at an appropriate level to faciliate formation of almost exclusively hypochlorous acid. The re-infusion of fresh solution contributed to the reduction and eventual elimination of surrogates and STEC-7 after 24 hours and *Salmonella* after 42 hours. Gradual reductions during the first hour of sampling may be attributed to a washing effect of organisms attached to non-inoculated meat, which was subsequently removed from the red water for lab testing. Of the target organims evaulated, the *Salmonella serovars* examined appear to have higher resistance to the Cesco-NAN-02 chlorinated nanobubble solutions, surviving longer than the rif-resistant surrogates and STEC-7 strains in red water (FIG. 16).

Pathogen Recovery on Lean and Fat

Little to no reduction of target organisms occurred on the surface of either inoculated lean or fat tissues (FIG. 4.17). This can be attributed to non-lethal levels of FAC present in the red water solution at the time the meat was introduced (4.13). All target organisms were recovered at 3-4 log CFU/g on non-inoculated lean and fat added to the containers 15 and 45 minutes after inoculated meat was dropped into the red water and subsequently removed (FIG. 4.18). This corresponds to the level of organisms recovered in water at the same time points (30 and 60 minutes as depicted in FIG. 4.16). Target organisms were still recovered on non-inoculated meat dropped into the system 24 hours after inoculated meat was introduced to the system (FIG. 4.19); these levels do not necessarily correlate to the levels of organisms present in the red water. STEC-7 and surrogates were recovered at lower levels (≤0.73 log CFU/g) than *Salmonella* spp. (1.0-1.6 log CFU/g).

Conclusion

Ultimately, FAC levels were extremely low and did not contribute much to lethality of STEC-7, surrogates, or *Salmonella* on the surface of inoculated lean and fat. *Salmonella* spp. persisted in the red water for 18 hours longer than STEC-7 and the surrogates and was recovered at higher levels than STEC-7 and surrogates on non-inoculated meat 24 hours after the introduction of inoculated meat. This could be due to the slightly higher inoculation load (~0.5 log CFU/g) on the lean and fat entering the system for *Salmonella*, or could be a result of higher resistance of *Salmonella* to the Cesco-NAN-02 technology water. Statistical analysis was not completed for this particular experiment therefore making judgements on differences difficult.

This experiment provided insight into the estimated number of organisms introduced into the Cesco-NAN-02 technology water system from inoculated meat and how long organisms persist in red water. Further research should be conducted to determine reduction of target organisms on inoculated lean and fat when dipped into a 5 ppm FAC red water solution, matching the USDA regulatory limit and target in-plant commercial validation study FAC parameters. Additional experiments should evaluate the effect of re-infusing solutions at different levels and/or different lengths of time compared to no re-infusions. The primary goal of this benchtop experiment was to approximate the parameters of a proprietary ground beef system in preparation to conduct an in-plant study validating a recirculating 5 ppm FAC, pH 5 Cesco-NAN-02 technology water enhanced using nanobubble technology as an antimicrobial step. Several parameters were hard to duplicate closely and could be re-evaluated in potential future benchtop experiments. These parameters include 1) a nitrogen crust freeze of meat to better represent beef tissues being treated in the commercial system, 2) continuous recirculation and reinfusion of Cesco-NAN-02 technology of water, 3) filtering of red water through a 50 µm particle filter during recirculation to remove some organics, and 4) maintaining lethal levels of FAC (approximately 5 ppm) in red water constantly.

Example 2

Evaluation of a Chlorinated Nanobubble Water System to Control Shiga Toxin-Producing *E. coli* Surrogates in a Novel Commercial Ground Beef Manufacturing Process Beef products, specifically ground beef, have been associated with human illness, disease outbreaks, and product recalls due to contamination from Shiga toxin-producing *E. coli* (STEC) and *Salmonella enterica*, both cattle harbored foodborne pathogens. Although not declared adulterants in beef, *Salmonella* has been associated with 35% of ground beef outbreaks from 2002-2011 (Laufer, A. S., et al. (2015). Outbreaks of *Salmonella* infections attributed to beef—United States, 1973-2011. *Epidemiology and Infection*, 143 (9), 2003-2013). The United States Department of Agriculture Food Safety and Inspection Service (USDA FSIS) has declared seven serotypes of enterohemmorhagic STEC to be adulterants in raw, non-intact beef—O26, O45, O103, O111, O121, O145, and O157: H7—due to the severity of illness caused after human consumption (Centers for Disease Control (CDC). (2012). National Shiga toxin producing *Escherichia coli* (*STEC*) *Surveillance Overview*. Atlanta, Ga.: US Department of Health and Human Services, CDC). STEC infection traditionally induces hemorrhagic colitis and, in severe cases, hemolytic uremic syndrome (HUS) in high-risk populations such as children. Similar to *E. coli*, *Salmonella* infections are characterized by gastrointestinal illness; however, *Salmonella* illness usually is self-limiting within 72 hours, except in severe cases death can occur from complications related to the illness, usually dehydration (Food and Drug and Administration (FDA). (2012). *Bad Bug Book, Foodborne Pathogenic Microorganisms and Natural Toxins* (2nd ed.)). *Salmonella* infections cause an estimated one million illnesses and 19,000 hospitalizations in the US annually (Centers for Disease Control (CDC). (2016). *Salmonella*, retrieved Oct. 30, 2016, from www.cdc.gov/Salmonella/), and are a major risk factor in a wide variety of raw and processed food products.

Meat processing establishments are required to implement Hazard Analysis and Critical Control Point (HACCP) plans which specifically mandate identification of biological, chemical, and/or physical hazards and critical operating parameters to control identified hazards, such as STEC and *Salmonella* in beef (FSIS, 1996). These critical operating parameters must be based on scientific evidence. If sufficient data is not available in the scientific literature, an in-plant validation study should be conducted (USDA Food Safety and Inspection Service. (2015). *Sampling verification activities for shiga toxin-producing Escherichia coli (STEC) in raw beef products* (No. FSIS Directive 10,010.1 Rev. 4). Washington D.C.). Validation of in-plant antimicrobial processes against select pathogens is critical; however, actual pathogens cannot be reasonably brought into food processing environments and laboratory research, while valuable as a reference, is not a substitute for actual in-plant validation (Niebuhr, S. E., et al. (2008). Evaluation of nonpathogenic surrogate bacteria as process validation indicators for *Salmonella enterica* for selected antimicrobial treatments, cold storage, and fermentation in meat. *Journal of Food Protection*, 71(4), 714-718). Therefore, the use of appropriate non-pathogenic indicator organisms, otherwise known as surrogates, can be valuable when evaluating effectiveness of individual plant processes against pathogens such as STEC and *Salmonella*.

Chlorinated water is often used as a critical control point (CCP) for controlling pathogens in poultry and produce washing processes; however, processes are not often scientifically validated during commercial process operations (Zhou, B., et al. (2015). Inactivation dynamics of *Salmonella enterica, Listeria monocytogenes*, and *Escherichia coli* O157:H7 in wash water during simulated chlorine depletion and replenishment processes. *Food Microbiology*, 50, 88-96). Electrolytically generated hypochlorous acid, one form of a chlorine antimicrobial, is allowed for use in meat and poultry processing operations as processing water and recirculated red water at levels not exceeding 5 ppm free available chlorine (FAC), and in poultry chiller water at a maximum of 50 ppm FAC (USDA Food Safety and Inspection Service. (2016). *Safe and suitable ingredients used in* the production of meat, poultry, and egg products (No. FSIS Directive 7120.1 Rev. 37). Washington D.C.). These treatments have been found to effectively reduce pathogens in wash water (Zhou, B., et al. (2015). Inactivation dynamics of *Salmonella enterica, Listeria monocytogenes*, and *Escherichia coli* O157:H7 in wash water during simulated chlorine depletion and replenishment processes. *Food Microbiology*, 50, 88-96) and on the surface of poultry carcasses and produce (Najjar, M. B., & Meng, J. (2009). *Risk Assessment of Disinfection Byproducts in Poultry Chilled in Chlorinated Water*. Joint Institute for Food Safety and Nutrition and Department of Nutrition and Food Science; Sohaib, M., et al. (2016). Postharvest intervention technologies for safety enhancement of meat and meat based products; a critical review. *Journal of Food Science and Technology*, 53(1), 19-30; Stopforth, J. D., et al. (2008). Effect of Acidified Sodium Chlorite, Chlorine, and Acidic Electrolyzed water on *Escherichia coli* O157:H7, *Salmonella*, and *Listeria monocytogenes* Inoculated on Leafy Greens. *Journal of Food Protection*, 71(3), 625-628; Yang, Y., et al. (2012). Enhanced Chlorine Efficacy against Bacterial Pathogens in Wash Solution with High Organic Loads: Enhanced Chlorine Efficacy against Pathogens. *Journal of Food Processing and Preservation*, 36(6), 560-566). Little research has been conducted with chlorinated water solutions as an antimicrobial on beef tissues, especially in a recirculating processing water dip scenario.

A relatively new concept in the food industry, nanobubble technology shows promise to aid in the development of improved food safety interventions. There is interest in nanobubbles due their proposed surfactant abilities or cleaning effect. Small particles in water can be effectively removed by introducing micro- or nanobubbles of opposing charge and zeta potential, which is controlled by the pH of the solution (Tsuge, H. (Ed.). (2014). *Micro- and nanobubbles: fundamentals and applications*. Singapore: Pan Stanford Publishing). Nanobubbles also provide increased surface area-to-volume ratio per mass as compared to standard water or other aqueous solutions (Bauer (2016) Nanobubbles from www.nanobubbles.com, Retrieved Oct. 3, 2016), which theoretically, enhances the efficiency of any dissolved or suspended antimicrobial components in solution. Nanobubble treatment, as a sanitation method, has been evaluated against norovirus surrogates in oyster bodies and was found to inactivate more than 99% of active virus after 12 hours (Tsuge, H. (Ed.). (2014). *Micro- and nanobubbles: fundamentals and applications*. Singapore: Pan Stanford Publishing).

The antimicrobial intervention for a novel ground beef manufacturing process (U.S. Pat. No. 9,167,843) was evaluated at a non-inspected commercial-scale pilot plant facility, with all manufactured beef products during the period of the inoculated studies being sent to inedible rendering operations. Briefly, this patented system utilizes higher-fat commercial beef trimmings to separate predominantly lean tissues from predominantly fatty tissues while the trimmings are being transported through a recirculating chilled antimicrobial fluid conduit system. Through proprietary operating conditions, lean tissues are recovered for further processing into raw ground beef demonstrating typical quality characteristics of traditionally manufactured product. An added benefit of this trim processing approach is the submersion of all beef tissue surfaces (fat and lean) in the recirculating fluid, which if adequately antimicrobial, provides a unique pathogen control opportunity in the raw ground beef manufacturing process. The portion of the trim treatment process utilizing the recirculating fluid is envisioned as operating over a multi-day period with continuous re-infusion of fresh make-up antimicrobial solution at defined points and intervals. Thus, such a system must be capable of inherent disinfection to prevent microbial build-up over the extended processing period.

Two inoculated in-plant studies were conducted using USDA-approved non-pathogenic surrogate cultures to evaluate the effectiveness of the recirculating antimicrobial fluid—an acidic (pH 5) Cesco-NAN-02 technology water [i.e. municipal water that is continuously chlorinated by infusion of concentrated chorine produced through an electrolyzed (EO) water process, acidified by introduction of $CO_2$ gas, and then passed through a patented nanobubble generator (U.S. Pat. No. 8,454,837)]. The first study was conducted to determine preliminary inefficiencies in operational variability/stability of the novel commercial scale ground beef system over a determined 6-day continuous production run and to optimize inoculation, sampling and testing protocols. The second study incorporated necessary processing system modifications to enable characterization of lethality of the antimicrobial process water on inoculated beef trimmings and equipment components included in the recirculating conduit system that support multi-day continuous processing. The optimized study will be used by the ground beef manufacturing company as scientific validation of this novel system for controlling enteric pathogens such as STEC and *Salmonella* spp. in their future commercial ground beef operations.

Unit Components of the Novel Ground Beef Processing System

The performance of a recirculating nanobubble water solution (i.e. Cesco-NAN-02 technology water) at pH 5 and that was continuously infused with concentrated chlorine [maximum free available chlorine (FAC) level of 5 ppm] was evaluated in a commercial-scale ground beef processing environment using a 6-day continuous run schedule. The processing flow is described below.

Receiving Beef Trim—Beef trim is received at the facility in approximately 2,000-lb commercial combo totes and stored between 3 and 5° C. until processing.

Grinding—The refrigerated combos are dumped into a commercial grinder and the beef trim is course ground through a ¾" plate onto a conveyor belt.

Freezing Tunnel—Meat is delivered to a liquid-nitrogen tunnel by the conveyor belt. The meat is exposed to a rapid 8-minute freeze on a separate stainless-steel switchback belt.

Bond Breaker—Crust-frozen meat drops from the freeze tunnel belt through two smooth metal rollers that "shatter" the meat into smaller pieces, beginning the fat and lean separation process of the proprietary system.

Vortex—From the bond breaker, the crust frozen 'shattered' meat falls directly into the antimicrobial chlorinated nanobubble process water at a vortex. This is the beginning point of a recirculating process water system comprised of multiple machinery components subsequently listed. The recirculating process water is described below. The vortex connects directly to the manifold.

Bulk Tank Chlorinated Cesco-NAN-02 technology Nanobubble Water—Bulk chlorinated (5 ppm FAC), acidified (pH 5) nanobubble water is generated onsite using a Cesco-NAN-02 technology process (in the current studies, a mobile generation plant on a trailer was utilized), which is then stored in a ~19,000 L bulk tank. This water is chilled to approximately 4° C. and used to initially fill the entire recirculating water system prior to beginning meat processing. Additionally, Cesco-NAN-02 technology water from this tank is infused at an approximate rate of 10% percent per hour immediately at the "Y" in the manifold, as described below, during meat processing operations to maintain proper processing water quality and replace water losses.

Manifold—The antimicrobial process water carries meat through a series of stainless steel pipes for 30 to 90 seconds. From a separate holding tank, fresh 5 ppm FAC, pH 5 Cesco-NAN-02 technology water is also introduced at 30-52 L/min at the "Y" section in the manifold. A majority of the predominantly lean meat tissue sinks to the bottom of the manifold pipes and subsequently drops down through a series of drop-ports into a collection tank that directly feeds to a dewatering centrifuge. Predominantly fat tissue floats through the manifold and into the agitated flotation tank.

Agitated Flotation Tank—Meat enters the ~18,000 L flotation tank at the front end (A) of the ~6 m long tank. A series of slow-moving rotating stainless steel paddles at the top of the tank facilitate agitation of the water and movement of the meat to either the bottom of the tank (mostly lean-type tissue) or the top of the tank (mostly high-fat tissue). Meat at the bottom of the tank is extracted through a series of ports and is pumped back to the collection tank mentioned above that feeds the dewatering centrifuge. Any meat floating in the tank or adhered to the walls of the tank is removed by the rotating paddles at the front end of the tank. To maintain the target level of 5 ppm FAC in the flotation tank, 50 ppm chlorine solution derived by diluting 5000 ppm Aquaox 5000™ (Aquaox LLC, Dillsburg, Pa., USA) is added into the back end of the tank at 80-685 mL/minute. The movement of the rotating paddles helps uniformly distribute the chlorine throughout the flotation tank.

Note: The addition of 50 ppm chlorine into the flotation tank to raise FAC in the presence of organic material in the tank water was only conducted during the optimized study.

Dewatering Centrifuge—The meat from four drop-ports along the ~6.7 m length of the manifold conduit is combined with lean meat that settles to the bottom of the flotation tank in the collection tank that supplies the dewatering centrifuge. This meat is centrifuged (P-3000 Sharples, Alfa-Laval, Warminster, Pa.) at 795.2×g to remove excess process water from the final lean meat product.

Final Product—Final beef products are gathered in two places: 1) Lean meat dropped from the dewatering centrifuge into a sanitized plastic bin or onto a collection belt; and 2) Fat scraped from the top of the agitated floatation tank and collected into a large plastic bin for further usage applications (not evaluated in the current study).

Particle Filter—The recirculating process water accumulates organic build-up over time from beef tissues introduced into the system. The antimicrobial process water is continuously pumped at a rate of ~20 L/min from the back end of the flotation tank through a 20 or 50-micron filter (Tequatic Plus SS-17 and SS-22 filters; Dow Chemical Company, Midland, Mich., USA) to remove particles from the recirculating system.

Chlorine Infusion—After the particle filtration, concentrated chlorine is continuously re-infused back into the recirculating system using full strength Aquaox 5000™ (5,000 ppm FAC; Aquaox LLC, Dillsburg, Pa.), which is commercially generated via electrolyzed water technology, to a target of 5 ppm FAC in the processing "red water" as it returns to the beginning vortex point of the process. Infusion is accomplished using a pump that delivers 40-162 mL/min into the conduit of the recirculating water stream.

Carbon Dioxide Infusion—Carbon dioxide gas is bubbled into the conduit containing the recirculating water immediately after particulate filtration to maintain the target pH 5.0-5.5.

Nanobubble Generation—In-line equipment generated new nanobubbles into the reinfused water system. The re-introduction of nanobubbles assists in stabilizing chlorine and pH levels in an aqueous solution with high organic levels, while also maintaining a higher ORP reading (an indirect measurement of nanobubble concentration).

2.1 Preliminary Validation Study
Materials and Methods
Antimicrobial Treatment Water Source The total volume of the recirculating process water system was ~23,000 L. On the day prior to initiating meat processing studies, the system was filled with Cesco-NAN-02 technology nanobubble water (pH 5, 5 ppm FAC), generated onsite by technical staff from Cesco Solutions, Inc. (Bellingham, Wash.) using a mobile generation system, and chilled to 4.5° C. Additional Cesco-NAN-02 water was generated and stored in a separate ~19,000 L bulk tank which entered the system at the 'Y' in the manifold as described above. Nanobubbles are generated by passing water through a patented (U.S. Pat. No. 8,454,837) generator utilizing cavitation chambers and shear planes to initiate an endothermic reaction thus producing a high concentration of paramagnetic oxygen nanobubbles with a mean particle size between 50 and 100 nm ("Bauer Nanobubbles," 2016).

The recirculating filtered Cesco-NAN-02 technology water solution ('red water') was continuously re-infused with a small volume (40-162 mL/min) of concentrated Aquaox 5000™ to boost processing water FAC levels back to 5 ppm, $CO_2$ gas was metered into the conduit (1-2 times daily at 1 min/ft$^3$ for approximately 15 min) to maintain 5±0.5 pH to increase the proportion of hypochlorous acid in the water while restricting chlorine off-gassing, and nanobubbles were generated by passing through a patented in-line generator as described above. This filtered, re-infused Cesco-NAN-02 technology water at 5 ppm FAC and pH 5 then reentered the opening of the vortex to treat in-coming crust frozen beef trim.

Meat Source

Six 2,000-lb combo totes of 25/75 (% lean to fat) commercial beef trim were obtained from a large beef processor approximately 7 days following production. These plastic covered totes were held in the processing room of the pilot facility at 8-17° C. for the 6-day study, with one combo tote used on each processing day. On the day of use of each combo of beef trim, the microbiological baseline quality of the product prior to inoculation was determined by collecting 15 mL of purge and conducting an analysis to estimate the total aerobic bacterial population and to determine the presence of any naturally present rifampicin-resistant bacterial populations.

Bacterial Cultures and Inoculum Preparation

Five strains of rifampicin-resistant non-pathogenic surrogate *Escherichia coli* (ATCC BAA-1427 P1, BAA-1428 P3, BAA-1429 P8, BAA-1430 P14, and BAA-1431 P68), trained to be rifampicin resistant (0.1 g/L) were obtained from Dr. Gary Acuff (Texas A&M University, College Station, Tex.) for use in this study (Laster, B. A., et al. (2012). Efficacy of trimming chilled beef during fabrication to control *Escherichia coli* O157:H7 surrogates on subsequent subprimals. Meat Science, 90(2), 420-425). These strains are rifampicin-resistant progeny of USDA FSIS-approved cultures deposited at the American Type Culture Collection (Manassas, Va.) for use as STEC surrogates for in-plant validation studies. Each strain was activated individually by transferring cryogenically frozen beads into Tryptic Soy Broth (TSB; Bacto, Becton, Dickinson and Co., Sparks, Md., USA) containing 0.1 g/L rifampicin (TSB+rif; Sigma-Aldrich, St. Louis, Mo., USA) stock solution and incubated at 37° C. for 24 hours.

Rifampicin stock solution (Rif) was prepared by dissolving 0.1 g rifampicin in 5 mL methanol (Fisher Chemical, Fair Lawn, N.J., USA) followed by filtering through a 0.22 µm sterile filter. Each culture was verified to not contain any virulence characteristics by latex agglutination (*E. coli* non-O157 identification kit, Prolex, Round Rock, Tex., USA) and by Assurance GDS PCR assay (BioControl, United Kingdom).

Meat—To prepare inoculum, 0.1 mL of each activated surrogate culture was transferred individually into 50 mL of TSB+rif and incubated at 37° C. for 24 hours. After incubation of the six flasks, 1 mL of each surrogate strain was combined into a 10-mL tube, mixed, serially diluted in phosphate buffered saline containing rifampicin, and plated on *E. coli*/coliform Petrifilm (ECC; 3M Corporation, Saint Paul, Minn.) that was incubated at 35° C. for 24 hours to confirm overall surrogate cocktail concentration. The remaining 49 mL of each culture were combined into a large sterile bottle (total of 245 mL) to use as a 5-strain surrogate cocktail inoculum. Two sets of surrogate cocktails were grown up to inoculate two separate batches of beef trim. Two 25±5 lb batches of course-ground (¾" grinder plate) beef trim obtained from a single combo to be used in the following day's studies were inoculated with 245 mL of the surrogate cocktail. In a disinfected plastic bin, the inoculum was evenly pipetted across the beef contained in each bin and mixed manually with latex-gloved hands to achieve uniform distribution. The inoculated beef in each batch was covered with plastic and held at ~4° C. for 24 hours before use.

Water—A preliminary process-water only (no meat added to the recirculating system) study, defined below, was conducted. To prepare surrogate inoculum for this study, 0.5 mL of each culture was added individually to 0.8 L of TSB+rif and incubated at 35° C. for 24 hours. Aliquots (1 mL each) from each 24-h culture bottle were mixed in a single 10 mL tube and enumerated as previously described to confirm overall surrogate cocktail concentration. The remaining portions of the individual cultures were combined into a surrogate cocktail inoculum (4 L total volume, referred to as the inoculum "slug").

Preliminary Water-Only Study Inoculation Study Parameters

Due to the large volume of water in the recirculating processing system, a preliminary study was conducted to evaluate a worst-case scenario of contaminated water. The ~23,000 L system was filled with pH 5, 5 ppm FAC Cesco-NAN-02 technology water 24 hours prior to the study, chilled to 4.5° C., and recirculated continuously at approximately 151 L/minute. Water temperature was maintained between 4 and 10° C. Processing room temperature varied between 8 and 17° C. during the time period of the testing, thus, influencing processing water temperature.

The addition of the concentrated surrogate inoculum "slug" into the Cesco-NAN-02 technology process water system was performed to achieve three primary objectives; 1) To determine the sensitivity of an Iso-Grid filtration method to enumerate surrogate populations diluted within the large make-up volume of the recirculating loop of the process, and 2) To determine the ability of a daily 4-h disinfection step (i.e., 5 ppm FAC chlorinated nanobubble water) in the continuous-run process to inactivate a high level of microbial contamination at the end of a day's processing run.

The 4 L slug of surrogate cocktail in TSB (at ~9 log CFU/mL) was introduced into the system at the vortex. The second goal of this preliminary study was to determine if recirculating the Cesco-NAN-02 technology water for 4 hours in an empty system (i.e., no meat) would reduce any remaining surrogate organisms to undetectable levels. Water samples were collected from four locations: the manifold at the drop-port, the flotation tank, and after the particle filter (before re-infusion of Aquaox 5000™ concentrated chlorine solution and $CO_2$), and the vortex (after re-infusion, where meat would enter the recirculating system). After the inoculum slug introduction, a process water sample was immediately (within 30 seconds, a time established by visually observing the amber inoculum solution passing by a window in the manifold conduit) drawn from the manifold drop-port; whereas, process water samples from the flotation tank, after the particle filter, and at the vortex return were taken after one hour of circulation to ensure a majority of inoculum passed through all parts of the processing system. The flotation tank holds ~75% of the total system's water and completely exchanges its volume after 90 minutes of total system recirculation. Approximately 2 L of water was collected from each sample port into a gallon-sized Ziplock bag (Johnson and Johnson Co., Racine, Wis., USA), and samples were taken to the on-site laboratory for immediate processing and analysis.

Parameters for the Preliminary Inoculated Meat Processing Study

The preliminary inoculated meat study began 48 hours after the completion of the preliminary water-only study. Approximately 12 hours following the preliminary water-only study, the company processed ~3000 lbs of non-inoculated beef trim (25/75 lean to fat) over a 4-h period to calibrate and equilibrate the system in preparation for beginning the preliminary inoculated beef study.

Each day before meat processing began, it was confirmed that the Cesco-NAN-02 technology processing water was equilibrated to 5 ppm FAC and pH 5 throughout the recirculating water. Each day 771 kg (1700 lbs) of beef was processed at 192-204 kg/hour over a 4-h period. At the beginning of each test day after 30 minutes of non-inoculated trim processing, the first 25-lb lug of surrogate-inoculated coarse ground beef was introduced onto the processing belt immediately after the grinder head, and this inoculated beef trim then passed through the nitrogen tunnel becoming crust frozen, and subsequently dropping through the bond breaker into the vortex. After approximately 2 hours of processing (the middle of production), the second 25-lb lug of inoculated ground trim was similarly introduced into the system.

Meat samples were collected at five successive sampling points in the process—the vortex (post-freezing but pre-introduction into the antimicrobial water solution), the manifold drop-port, after the dewatering centrifuge (final lean product), from the bottom of the flotation tank (representing secondarily recovered lean), and from the top of the flotation tank (representing fat)—using a sanitized wire mesh food strainer (Good Cook Touch, Rancho Cucamonga, Calif.) and transferred aseptically into Ziplock bags. The frozen shattered meat sample collected at the vortex was timed to ensure actual sampling of inoculated meat, as opposed to the continuously introduced non-inoculated ground trim from the grinder head, by timing the belt speed through the nitrogen tunnel. Meat samples at the other points were collected at 30-90 sec time intervals (dependent on valve openings) successively as the meat progressed through the recirculation system. Additionally, a matching set of meat samples were collected 20-45 minutes after the inoculated meat had exited the system to evaluate the level of surrogate organisms picked-up by non-inoculated beef product.

The ~23,000 L system filled with Cesco-NAN-02 technology water was recirculated continuously at approximately 151 L/minute. Water temperature was maintained between 4 and 10° C. during a 4-h meat production run, and between 10 and 15° C. during the 4-h period of recirculating water-only (water containing 5 ppm FAC at pH 5, but no meat entering the system) and overnight. Room temperature was maintained between 8 and 17° C.

Processing water samples were collected three times daily: 10 minutes after inoculated meat entered the system at the beginning and middle of the day, and after the 4-hour disinfection period. Water samples were collected from four locations: the manifold at the drop-port, the flotation tank, after the particle filter (before re-infusion of Aquaox 5000™ concentrated chlorine solution and $CO_2$), and at the vortex (after re-infusion where meat would enter the recirculating system) as described above.

Due to the nature of a recirculating solution system, replications are differentiated by day with each day being an experimental replication (for a total of 6 replications). Each replication (day) was characterized by a new combo tote of beef trim, newly prepared and administered surrogate inoculum cocktail, and a production break consisting of the 4-h disinfection period plus overnight recirculation of processing water through the conduits and its associated equipment.

Pre-Operation and Environmental Sponges

Sterile sampling sponges (Nasco, Fort Atkinson, Wis., USA) rehydrated in 25 mL of DE Neutralizing Broth (DE broth; Difco, Becton, Dickinson and Co., Sparks, Md., USA) were used to swab major pieces of equipment—the grinder conveyor belt, the bond breaker, and the inside lid and drop chute of the dewatering centrifuge—prior to production starting on Day 3. Using rehydrated sponges, environmental samples were also collected to determine if rif-resistant organisms were present outside of the beef processing system on items such as door handles, lab coats, floors, etc.

Chemical Analysis of Process Water pH and oxidation-reduction potential (ORP) of the recirculating Cesco-NAN-02 technology water were monitored continuously with in-line probes (M300; Mettler Toledo, Columbus, Ohio). Free available chlorine (FAC) and total chlorine (TC) levels were determined by amperometry (Chlorosense, Palintest, Erlanger, Ky., USA). These readings were recorded three times per day on water samples within 5 min of collection. Independent readings of the FAC level (Service Complete Kit; Taylor Technologies, Sparks, Md., USA), pH, and ORP were taken by Cesco Solutions technicians to determine an overall profile of system operations and to continuously adjust the processing water to 5 ppm FAC and pH 5.

Microbiological Analysis

Meat Samples—Twenty-five gram portions of each meat sample were added to a Whirl-Pak bag (Nasco, Fort Atkinson, Wis., USA) containing 100 mL DE broth within 2 min of collection from the processing system. Bags were stomached (Stomacher 400 Lab Blender, Seward Laboratory Systems Inc., Fla., USA) at 230 RPM for 60 seconds and plated on Aerobic Plate Count Petrifilm (APC; 3M Corporation, Saint Paul, Minn., USA) to determine overall microbial populations. To determine recovery of rifampicin-resistant surrogates, 10 mL of the original homogenized sample in DE broth was removed from the original bag and added to 0.1 g/L rif and plated onto E. coli/Coliform (ECC) Petrifilm using Phosphate Buffered Saline (PBS; AMRESCO, LLC., Solon, Ohio, USA) blanks containing 0.1 g/L rif (PBS+rif). All ECC and APC Petrifilm were incubated at 35° C. for 24 hours.

Water Samples—A 500 mL aliquot of each water sample was immediately pre-filtered through a No. 1 Whatman filter (United Scientific Supplies, Waukegan, Ill., USA) using a sanitized plastic or ceramic Buchner funnel (Sigma-Aldrich, Darmstadt, Germany) fitted onto a sanitized 1-L side-armed flask connected to a mechanical vacuum pump to remove suspended organic particles. Portions of the pre-filtered water sample were subsequently filtered through two 1600-square hydrophobic grid membranes (Neogrid; Neogen, Lansing, Mich., USA), separately filtering 60-250 mL (dictated by how fast the filter became loaded) through each membrane filter under vacuum. One membrane was washed with a 5-mL aliquot of DE broth to remove any residual chlorine and placed onto a Sorbitol MacConkey Agar plate containing 0.1 g/L rifampicin (SMAC-R) to enumerate surviving surrogate populations; the other membrane was inserted into a sterile conical tube (VWR International, Randor, Pa.) containing 45 mL TSB+rif for enrichment and subsequent qualitative detection of viable surrogate populations present in process water but below the direct plating detection level of the Iso-Grid procedure (1 CFU/60-250 mL filtered). Both the membrane grids on SMAC-R plates and in enrichments were incubated at 37° C. for 24 hours. Each water sample was also directly plated using APC Petrifilm to determine overall microbial levels, and using ECC Petrifilm diluted with PBS+rif to recover rif-resistant surrogates in the processing water.

Sponges—Environmental sponges in their respective Whirl-pak bags were hand massaged for 1 min. To recover rifampicin-resistant surrogates, 10 mL of the original DE Neutralizing broth squeezed from the sponge was removed and added to 0.1 g/L rif and plated using PBS+rif dilution blanks onto ECC. Each sample was also directly plated onto ECC. All ECC Petrifilm plates were incubated at 35° C. for 24 hours.

2.2 Optimized Validation Study to Evaluate the Effectiveness of the Cesco-NAN-02 Technology Recycling Process Water System for Controlling STEC Surrogates During a 6-Day Processing Scenario Antimicrobial Process Water Source The production and application of the chlorinated Cesco-NAN-02 technology nanobubble water in the proprietary ground beef manufacturing system are described above.

Meat Source

Six tons of 25/75% (lean/fat) beef trim was obtained from a large beef processor approximately 7 days following production, as described above. Upon receipt, the meat was held on a refrigerated truck at −1° C. for the duration of the study.

Bacterial Cultures and Inoculum Preparation

USDA-approved E. coli surrogate cultures, preparation of inoculum, and the inoculation procedure of 25-lb lugs of beef trim are described above.

System Sanitation and Disinfection

When this novel ground beef manufacturing system is actually utilized to commercially process beef trim into finished ground beef product, it is envisioned that the production schedule would be 20 hours of continuous separation and treatment of lean and fat from combo beef trim, followed by a 4-hour running of the recirculated water with all processed meat removed from the system and no new meat introduced. During this 4-h period, the recirculating Cesco-NAN-02 technology water would be infused with concentrated chlorine (Aquaox 5000) to elevate the FAC level to 50 ppm for a 30-min period as a total system disinfection step, with a decline in FAC back to 5 ppm by the end of the 4-hour period, at which time the same beef trim processing schedule would be utilized. This 20-h process and 4-h disinfection rotation would be repeated daily for 6 days. On the seventh day, a total breakdown of all equipment and conduit components for cleaning and disinfection would occur.

In this surrogate-inoculated beef trim study, a 4-h disinfection period was incorporated into the study design directly following production at the end of every day, as would occur during regular commercial processing for this establishment. The Cesco-NAN-02 technology process water, now 'red water', continued to recirculate throughout the system. During the disinfection period of the recirculating process water loop, major pieces of external equipment were taken off-line and manually cleaned and disinfected, specifically, the interior lid and drop chute of the dewatering centrifuge, the bond breaker, the particle filter, and the conveyor belt at the grinder. Equipment was rinsed with 82° C. water followed by a quaternary-ammonium based foaming surfactant cleaner (Cesco Hurricane; Cesco Solutions, Bellingham, Wash.), manually scrubbed, re-rinsed with 82° C. water, and disinfected (Cesco Avalanche Chip; Cesco Solutions, Bellingham, Wash., USA). Equipment normally included within the Cesco-NAN-02 technology water processing loop (dewatering centrifuge and particulate filter) was temporarily by-passed from the recirculating solution during cleaning and disinfection. Following equipment disinfection, the FAC in the recirculating system was brought up to 50 ppm with 150-190 L Aquaox 5000™ manually added to the top of flotation with 5-gal buckets for a period of 30 minutes to disinfect the water, internal equipment parts, flotation tank fat skimming paddles, and manifold piping. This elevated level of FAC was then reduced by adding 1,200-2,000 mL of sodium thiosulfate (Cesco Antichlor No. 3, Cesco Solutions, Bellingham, Wash., USA) at the end of the disinfection period to return the system to the 5 ppm FAC target operational level. In this inoculated study, after the 4-h elevated chlorine disinfection process, the process water continued recirculating overnight for 12-15 hours with 30 mL Aquaox 5000™/min being continuously added at the point of chlorine infusion.

Water-Only Inoculation Study to Evaluate Effectiveness of an Optimized Set of Operational Parameters and an Elevated Chlorine Disinfection Step The morning (~5 h) prior to initiating the inoculated meat processing study, the Cesco-NAN-02 chlorinated nanobubble system circulating at 151 L/min and equilibrated to 5 ppm FAC, pH 5 was inoculated with a 4-L slug of surrogate cocktail (~9 log CFU/mL in TSB) in a similar manner as described elsewhere herein. Water temperature was maintained between 4 and 10° C. Room temperature was maintained between 8 and 17° C. The goal of this evaluation was to determine if the 4-h disinfection period, specifically the increase of FAC to 50 ppm for 30 minutes, would reduce the overall surrogate population in the processing water to below detectable levels. Water samples were collected from four locations—the manifold, the flotation tank, and after the particle filter (before re-infusion of electrolyzed chlorinated water and $CO_2$), the vortex (after re-infusion where meat would enter the recirculating system)—before and after the 50 ppm FAC spike. After the 4 L inoculum slug introduction, a sample was immediately (within 30 seconds) drawn from the manifold; whereas, water samples from the flotation tank, after the particle filter, and at the vortex were taken after one hour to ensure passage of the inoculum through all parts of the system (conduits, valves, and processing equipment within the recirculating loop). The flotation tank holds ~75% of the system's water volume and completely exchanges its volume over a 90-min period. Approximately 2 L of water were collected from each sample port into a gallon-sized Ziplock bag, which was immediately transported to the onsite laboratory for microbiological analysis.

Inoculated Meat Study Parameters

The inoculated meat validation study began 30 minutes after the completion of the water-only study described elsewhere herein. Before initiating ground beef processing, the FAC and pH levels of the recirculating Cesco-NAN-02 technology water system were confirmed to be 5 ppm and 5, respectively, throughout the recirculation loop.

On each of the six consecutive days, 771 kg of beef trim (25/75 percent lean/fat) was processed at 192-204 kg/h over 4 hours. This protocol was similar to section the preliminary inoculated meat processing study except the experimental design called for inoculated beef trim to be added to the processing flow on days 1, 3 and 5 and non-inoculated meat to be processed on days 2, 4 and 6. On the inoculated meat processing days, a 25-lb lug of inoculated course ground (¾" plate) beef trim was dumped at the start-up of the production run in a single layer onto the conveyor belt exiting the grinder head, allowing this trim to pass through the nitrogen freeze tunnel and bond breaker into the vortex (point where trim enters the Cesco-NAN-02 technology water processing loop). A second 25-lb lug of inoculated trim was dumped once again in the middle of the 4-h production run. After each inoculated batch of trim entered the vortex, meat samples were collected as described above. Non-inoculated beef trim was coarse ground, crust frozen, shattered, and processed through the Cesco-NAN-02 technology water system after each inoculated lug dump in a continuous manner. On these days, beef component samples were collected 45 minutes after each inoculated lug had exited the recirculating system to evaluate the level of surrogate organisms picked-up by subsequently processed non-inoculated beef trim (representing a highly contaminated batch of trim going through the system to determine propensity for contamination to spread to non-contaminated product.

Production runs on days 2, 4 and 6 were conducted, whereby only non-inoculated beef trim was processed through the same manufacturing system on the day following the previous evening's 4-h disinfection process. The goal of this part of the study was to determine if *E. coli* surrogates might survive the Cesco-NAN-02 technology water disinfection protocol at points along the processing continuum and potentially contaminate the next day's production run. Lean and/or fat beef samples were collected at the beginning, middle, and end of the 4-hour beef trim processing run. For both inoculated and non-inoculated study components, meat samples were collected from 5 sampling points in the Cesco-NAN-02 technology recirculating loop as described above.

Throughout the study, the ~23,000 L system, filled with pH 5, 5 ppm Cesco-NAN-02 technology water, was recirculated continuously at approximately 151 L/minute. Water temperature was maintained between 4 and 10° C. during production and between 10 and 15° C. during the disinfection period and overnight. Room temperature was maintained between 8 and 17° C. Water samples for microbiological analysis were collected three times daily as described above. On inoculated meat processing days, Cesco-NAN-02 technology process water was collected 10 minutes after inoculated meat entered the system at the beginning and middle of the day, and after the 4-hour disinfection period. On non-inoculated meat processing days, process water samples were collected at the beginning and end of beef production, and after the 4-hour disinfection period. Water samples were collected as described in the water-only study.

Due to the nature of a recirculating solution, and whereby new meat, new inoculum, daily 4-hour disinfection occurred, three experimental replications were determined. Replication 1 was defined as production days 1 and 2, replication 2 as days 3 and 4, and replication 3 as days 5 and 6.

Pre-Operation Environmental Sponges to Identify Presence of Viable Surrogate Bacteria To gauge the effectiveness of nightly processing room and equipment sanitation during the 6-day experiment, sterile cellulose sampling sponges rehydrated in 25 mL of DE Neutralizing Broth were used to swab major pieces of equipment—the grinder conveyor belt, the bond breaker, the inside lid and drop chute of the dewatering centrifuge—previously identified as potential microbial harborage points in the preliminary in-plant study after daily sanitation. Using rehydrated sponges, 3-7 additional environmental samples were taken on items such as door handles, lab coats, floors, etc. every other day to determine if rif-resistant organisms were present outside of the inoculated beef processing system.

Chemical Analysis of Cesco-NAN-02 Technology Processing Water Samples

Free available chlorine (FAC), total chlorine, pH, and oxidation-reduction potential (ORP) readings of processing water were collected as described above. These analyses were conducted on-site using an amperometric meter (Chlorosense, Palintest, Erlanger, Ky., USA) for FAC and total chlorine and in-line probes for ORP and pH.

The method used for trihalomethane analysis was a modification of Dos Santos and colleagues using a solid phase microextraction fiber (SPME) coupled with gas chromatography-mass spectrometry (GC-MS) operated in the SIM/SCAN mode (Dos Santos, M. S., et al. (2011). Determination of THMs in soft drink by solid-phase microextraction and gas chromatography. *Food Chemistry*, 127(1), 290-295). Process water samples for analysis were obtained before production, after production, and after the 4-hour disinfection period at the vortex and flotation tank daily. Water was collected in 120-mL glass amber bottles certified for chemical residue detection in potable water systems (Cat. No. 241-1020; Thermo Scientific, Rockwood, Tenn.) and immediately frozen on-site. Samples were then shipped overnight for analysis at the Kansas State University Food Chemistry Laboratory directed by Dr. J. Scott Smith. Upon receipt at the lab, samples were held at −20° C. until analyzed.

The frozen process water samples were removed from −20° C. storage and held at room temperature for about 2 hours with occasional shaking until thawed. From each sample, a 0.75 or 1.5 mL aliquot was pipetted into a 4-mL glass vial with a silver seal cap having a PTFE/silicone liner. A solid phase microextraction fiber (75 µm CAR-PDMS, Supelco, USA) was exposed to the sample headspace for 15 minutes, withdrawn and inserted into the GC injection port for 1 minute at 280° C. GC/MS (Agilent Technology Inc., Santa Clara, Calif.) separation was achieved on a HP-5MS (60 m×0.25 mm×0.25 µm) column with a temperature program of: hold 40° C. for 4 min, increase to 180° C. at a rate of 40° C./min, and hold at 180° C. for 4 min. The helium carrier gas was at a flow rate of 1 mL/min. The MS data was collected in either the SCAN or SIM modes. For the SCAN mode, ions were collected between 35-600 m/z and peaks were checked for compound identification with the NIST/EPA/NIH Mass Spectral Library (version: NIST 14).

Quantification of trichloromethane was with the MS operated in the SIM mode set for the major fragment ions of trichloromethane (m/z 83, 85, 118, and 120 ions). A standard curve of trichloromethane levels versus concentration was achieved by measuring integrated peak areas of the major ions of standards of 1, 25, 50, 100, and 150 ppb in the headspace vial. Reagent grade chloroform (Acros Organics, 99.8+%, stabilized with ethanol, CAS 67-66-3) was used to make the standard dilutions from a 100 ppm standard stock solution diluted with halogen-free LC/MS water (Optima, Fisher Chemicals).

Microbiological Analysis of Meat and Process Water Samples

Meat Samples—Samples were processed as described above. For enrichment of meat samples, 10 mL of original homogenized sample was added to 90 mL TSB+rif and incubated at 37° C. for 24 hours. 24-hour enrichments were subsequently streaked using sterile cotton swabs onto SMAC-R agar plates and incubated at 37° C. Results were read as positive (growth) or negative (no growth) for qualitative detection of surviving organisms below the detection limit (0.4 log CFU/mL) after 24 hours.

Water Samples—Samples were prepared and processed similar to the methods described above with several modifications. A 500-mL aliquot of each water was immediately pre-filtered through a series of ~4 Whatman filters decreasing in size (Q5, P4; Fisher Scientific, Pittsburgh, Pa., USA; #1; United Scientific Supplies, Waukegan, Ill., USA) to remove particles larger than 4 µm. The used pre-filters were aseptically placed into a Whirl-pak with 100 mL of TSB+rif for enrichment using sterilized forceps to qualitatively determine if surrogates potentially were attached to larger organic particles in the process water, thus being filtered out by the pre-filter process. Of each resultant pre-filtered water sample, a 60-250 mL portion (dictated by how fast the filter became loaded) was filtered through a 1600-square hydrophobic grid membrane (Neogrid; Neogen, Lansing, Mich., USA) under vacuum, subsequently washed with 5 mL of DE broth, and placed onto a SMAC-R plate to enumerate viable STEC surrogates. The Whatman pre-filter enrichments were incubated at 37° C. for 24 hours. After 24 hours, pre-filter enrichments were streaked onto SMAC-R agar plates and incubated for 24 hours at 37° C. Each water sample was also directly plated onto APC Petrifilm to determine overall microbial concentration in the process water and on ECC Petrifilm diluted with PBS+rif to enumerate rif-resistant surrogates. Sponges—Sponges were prepared and processed as described above.

Statistical Analysis of Meat Sample Microbiological Data

There are two points in the overall beef trim processing system where pathogens can be reduced on meat tissues: 1) During the cryofreeze as shown from the inoculated meat to the vortex due to general freeze injury and possibly dehydration, and 2) From exposure to the free available chlorine in the recirculating water as shown at the post-surge tank, final lean, fat tank and final fat. Therefore, two statistical analyses were completed. Both analyzes were performed using the MIXED procedure in SAS 9.4 (SAS Institute Inc., Cary, N.C., USA). For each analysis, a randomized complete block design was assumed and type 3 tests of fixed effects were evaluated to determine significance of interactions and/or main effects based on a P-value of $\alpha=0.05$.

The first analysis, determining the effect of the cryofreeze, utilized Fisher's Protected LSD based on initial review of the model and graphical diagnostics, which showed two variances. For the second analysis, treatments were separated into 7 scenarios: 1) AM inoculated meat, 2) AM same-day pick-up meat, 3) PM inoculated meat, 4) PM same-day pick-up meat, 5) 24-hour pick-up meat beginning of day, 6) 24-hour pick-up meat middle of day, and 7) 24-hour pick-up meat end of day and evaluated using a Tukey-Kramer adjustment for all comparisons.

Units (MPNGU) calculated as described in Equation 1 (Patel, P. D. (Ed.). (1995). *Rapid Analysis Techniques in Food Microbiology*. Boston, Mass.: Springer US).

Preliminary Water Studies

In a worst-case scenario, a high level of contamination may be present in recirculating water following a day of beef processing. To determine the sanitizing power of the recirculating water alone, without organic material in the system, inoculum was added via the 4-L concentrated inoculum slug that, through theoretical calculation, would result in a level of $1.6 \times 10^5$ CFU/mL of *E. coli* surrogates in the water if no lethality occurred. During the first preliminary water-only study that occurred before the preliminary meat processing validation study, no apparent immediate lethality was seen at the manifold; this is most likely due to an initial dilution factor of the inoculum entering the system as a 'slug' and subsequent immediate binding of chlorine as the slug passed through (Table 4). There was no recovery of surrogates after 4 hours of recirculating process water at an average $3.4 \pm 1.6$ ppm FAC. This indicates that simply recirculating Cesco-NAN-02 technology water during a 4-hour sanitation period (with no enhanced-level chlorine spiking) would reduce pathogen populations in the water to undetectable levels.

TABLE 4

Water-only Study Results, Preliminary Validation Study.

| | Manifold | | Flotation Tank | | Post-Particle Filter | | Vortex | |
|---|---|---|---|---|---|---|---|---|
| | Beginning | End | Beginning | End | Beginning | End | Beginning | End |
| FAC | 0.02 | 3.9 | 2.6 | 5.6 | 2.8 | 4.2 | 3.6 | 5.0 |
| Total Cl | — | 4.8 | 4.8 | 6.2 | 3.7 | 4.7 | 4.8 | 5.0 |
| pH | 5.67 | 5.69 | 5.69 | 5.69 | 5.65 | 5.53 | 5.55 | 5.55 |
| ORP | 472 | 885 | 884 | 910 | 890 | 913 | 895 | 917 |
| CFU/mL | 7.7 Log | — | 235* | — | — | — | — | — |

Beginning-Samples taken directly after inoculum introduced to system; Manifold-30 seconds; Flotation Tank, Post-Particle Filter, Vortex-1 hour post-inoculum introduction; End-Samples taken at the end of the 4-hr sanitation (water recirculating at 3.4 ± 1.6 ppm FAC).
*Determined by positive enrichment ISO-GRID, calculated based on detection limit.

Results and Discussion

Water Samples

A hydrophobic grid membrane filter (HGMF) method, a common form of enumeration in water microbiology, were used in this study to improve detection limits from process water samples. Benefits of HGMF include no need for serial dilutions, reduced labor, reduced counting error due to grid-colony distinction, and the filtration of larger volumes of water than can be analyzed by direct plating (Patel, P. D. (Ed.). (1995). *Rapid Analysis Techniques in Food Microbiology*. Boston, Mass.: Springer US). ISO-GRID HGMF consists of a 1600-grid extended Most Probably Number (MPN) test with accuracy up to 4 log cycles of growth, reported as Most Probable Number of Growth Forming Similar results are reported for the water-only study that included the implementation of a 50 ppm FAC boost during the 4-hour sanitation period. *E. coli* surrogates were added in to the system at the same level as previously described, but were immediately recovered at much lower levels. High levels of surrogate organisms were recovered at the manifold, albeit slightly lower than the previous 5 ppm FAC water-only study, indicating that aside from an initial dilution factor, free chlorine had an initial impact before being completely bound (Table 5). A low level of surrogates was still detectable at the beginning of the 50 ppm chlorine boost; however, surrogates were not recovered anywhere in the system after the 4-hour elevated chlorine disinfection period.

TABLE 5

Water-only Study Results, Optimized Validation Study.

| | Manifold | | Flotation Tank | | Post-Particle Filter | | Vortex | |
|---|---|---|---|---|---|---|---|---|
| | Beginning | End | Beginning* | End | Beginning* | End | Beginning | End |
| FAC | 0.14 | 4.1 | 27.5 | 4.4 | 41.5 | 3.9 | 43* | 5.1 |
| Total Cl | 3.9 | 4.1 | 29 | 4.9 | 41.5 | 4.7 | 43 | 5.8 |
| pH | 5.64 | 4.88 | 5.68 | 4.92 | 5.64 | 4.92 | 5.04 | 4.93 |

TABLE 5-continued

Water-only Study Results, Optimized Validation Study.

|  | Manifold | | Flotation Tank | | Post-Particle Filter | | Vortex | |
| --- | --- | --- | --- | --- | --- | --- | --- | --- |
|  | Beginning | End | Beginning* | End | Beginning* | End | Beginning | End |
| ORP | 850 | 926 | 967 | 945 | 706 | 636 | 956 | 834 |
| CFU/mL | ~4 logs¥ | — | 0.028 | — | — | — | — | — |

*1-hr sampling point occurred during beginning of 50 ppm chlorine boost to system;
¥ISO- GRID overgrown, no growth on ECC direct plate, estimated approximately 4 logs MPNGU in water due to ISO-GRID sensitivity.

Equation 1: Most Probable Number of Growth Forming Units (MPNGU) CFU/mL reported for samples with growth on 1600 MPN grids calculated as:

$$\left(-1600 * \frac{LOG^{1600-\# \text{ of positive grids}}}{1600}\right) \div \# \text{ of mLs passed through grid}$$

Chlorine Demand and Surrogate Recovery During Meat Processing

A major limitation of chlorine in a meat processing system is that it is easily bound and deactivated by organic matter (Sohaib, M., et al. (2016). Postharvest intervention technologies for safety enhancement of meat and meat based products; a critical review. *Journal of Food Science and Technology,* 53(1), 19-30). Although the particle filter removes coarse debris from the recirculating water solution, soluble organic matter continues to accumulate over time which accelerates free chlorine depletion (Yang, Y., et al. (2012). Enhanced Chlorine Efficacy against Bacterial Pathogens in Wash Solution with High Organic Loads: Enhanced Chlorine Efficacy against Pathogens. *Journal of Food Processing and Preservation,* 36(6), 560-566; Zhou, B., et al. (2015). Inactivation dynamics of *Salmonella enterica, Listeria monocytogenes,* and *Escherichia coli* O157:H7 in wash water during simulated chlorine depletion and replenishment processes. *Food Microbiology,* 50, 88-96).

Chlorine dosing, especially when done manually as was performed during this study, can be difficult to determine and, therefore, difficult to maintain consistent free chlorine levels. Yang et al. (2012) showed that an initial level of 35 ppm FAC was reduced to 0 ppm after only 4 lettuce dip washes; replenishing the solution with the same amount of NaClO as originally used only resulted in FAC restoration levels between 7.2 and 17 ppm. This observation indicated that higher levels of NaClO were needed over time to maintain FAC in solution. When levels of FAC are low in a recirculating solution, pathogens have a potential opportunity to survive and cross-contaminate meat in the system. However, Zhou and colleagues determined that organic loading and initial chlorine concentration do not directly affect chlorine efficacy in solution, contrary to prior belief. Chlorine demand in protein-containing (i.e. beef and poultry) solutions is quite high compared to other food matrices (Zhou, B., et al. (2015). Inactivation dynamics of *Salmonella enterica, Listeria monocytogenes,* and *Escherichia coli* O157:H7 in wash water during simulated chlorine depletion and replenishment processes. *Food Microbiology,* 50, 88-96). In a study conducted by Waters and Hung, up to 82.5% and 75-92.5% of total free chlorine was lost in beef and turkey solutions, respectively, compared to relatively low chlorine loss observed in starch, fat, and mineral solutions (Waters, B. W., & Hung, Y.-C. (2014). The effect of organic loads on stability of various chlorine-based sanitisers. *International Journal of Food Science & Technology,* 49(3), 867-875). Zhou and colleagues determined that a minimum FAC level of 3.66 ppm at pH 5.12 to 6.97 and an ORP above 850 mV in a recirculating produce wash water system was sufficient to reduce *Salmonella enterica, E. coli* O157:H7, and *Listeria monocytogenes* by 6 log cycles after a 30 second contact time independent of organic loading and initial chlorine concentration (Zhou, B., et al. (2015). Inactivation dynamics of *Salmonella enterica, Listeria monocytogenes,* and *Escherichia coli* O157:H7 in wash water during simulated chlorine depletion and replenishment processes. *Food Microbiology,* 50, 88-96).

During the optimized study, the average FAC and ORP across the system was lower than the 3.66 ppm and 850 mV observed by Zhou and colleagues to be successful for pathogen reduction in produce wash water: Vortex 3.31±0.92 ppm, Manifold 1.31±1.39 ppm, Flotation Tank 1.74±1.26 ppm, Post-Particle Filter 1.62±1.23 ppm and an average ORP of 715±161 mV as recorded by KSU personnel (Zhou, B., et al. (2015). Inactivation dynamics of *Salmonella enterica, Listeria monocytogenes,* and *Escherichia coli* O157:H7 in wash water during simulated chlorine depletion and replenishment processes. *Food Microbiology,* 50, 88-96). However, no viable organisms were recovered on any ISO-GRID. A few of the Whatman filter enrichments (FIG. 26 and FIG. 27) were found to be positive following introduction of inoculated meat into the system, indicating that surrogates were still in the recirculating red water at low levels, but were attached to filterable organic material. Whereas, no pre-filter enrichments were found to be positive following the 4-h disinfection period after production. It is likely that there were antimicrobial effects from chloramine formation—which was not measured in this study. In the presence of proteins, chlorine will form chloramines and retain residual antimicrobial effects even after depletion of free available chlorine. Block (1991) reported 100% reductions of *Salmonella pullorum* in a 130 ppm hypochlorite solution with 5% organic matter although there was no measurable level of FAC, showing the sanitizing capacity of chloramines.

In the preliminary meat processing study, Whatman pre-filters were not enriched to determine presence of surrogates attached to filterable particulates. However, similar results were observed overall compared to the optimized beef processing study. The average FAC at the manifold, flotation tank, and post-particle filter were relatively lower in the preliminary meat processing study than in the optimized study—Vortex 3.47±0.91 ppm, Manifold 0.66±0.92 ppm, Flotation Tank 0.24±0.30 ppm, Post-Particle Filter 0.26±0.33 ppm—but, the ORP throughout the system was similar between studies, with an average ORP of 717±164 mV. During the preliminary study, several ISO-GRID membranes recovered rif-resistant surrogates: 0 of 18 Vortex samples, 6 of 18 Manifold samples (including 1 after the 4-hr water recirculation disinfection period), 1 of 18 Flotation Tank samples, and 2 of 18 Post-Particle Filter samples.

This is most likely due to decreased free chlorine levels in the manifold, flotation tank, and after the particle filter as compared to the optimized study. Based on the results from the preliminary study and knowing chlorine would bind with the organic material from the meat and in the water almost immediately, the goal of the optimized study was to maintain a level of 5 ppm chlorine, or at least residual chlorine, throughout the system in order to continuously allow for chlorine to contact the meat surface and reduce the level of surrogate organisms recovered in the water. This was an effective strategy. In the future, in-line chlorine meters should be installed and used to operate the mechanical injection of Aquaox 5000™ into the system to maintain better control of free chlorine levels throughout the recirculating water. In processing environments, chlorine is extremely effective at controlling pathogen levels in wash water, yet minimally impacting the levels of pathogens on the surface of produce or poultry (Zhou, B., et al. (2015). Inactivation dynamics of *Salmonella enterica*, *Listeria monocytogenes*, and *Escherichia coli* O157:H7 in wash water during simulated chlorine depletion and replenishment processes. *Food Microbiology*, 50, 88-96), thus supporting the minimal levels of rif-resistant surrogates recovered in both studies.

Chlorine By-Product Results in Recycled Processing Water

The values reported (Table 6) were obtained with the MS operated in the SIM mode. Many samples were diluted with halogen-free water in order to fit on the standard curve. The method used was unable to identify other organohalogen compounds, such as dichloromethane, when analyzed with the MS in the SCAN mode and, is not suitable for the detection of trihaloacetic acids. All of the water samples analyzed report levels of THMs higher than 0.08 mg/L or 80 ppb (Table 6), the maximum residual disinfectant level for potable water in the United States (EPA, 2001). This is interesting because levels of chlorine are much higher in commercial poultry establishments yet yield much lower levels of disinfection by-products, generally below 0.08 mg/L (Najjar, M. B., & Meng, J. (2009). *Risk Assessment of Disinfection Byproducts in Poultry Chilled in Chlorinated Water*. Joint Institute for Food Safety and Nutrition and Department of Nutrition and Food Science; Vizzier-Thaxton, Y., et al. (2010). Generation and detection of trihalomethanes in chicken tissue from chlorinated chill water. *The Journal of Applied Poultry Research*, 19(2), 169-173). These by-products are volatile and reported to dissipate in an open environments, especially in agitated chill tanks (Vizzier-Thaxton, Y., et al. (2010). Generation and detection of trihalomethanes in chicken tissue from chlorinated chill water. *The Journal of Applied Poultry Research*, 19(2), 169-173), often leading to non-hazardous levels within water.

Risk assessments have been conducted evaluating levels of residual disinfection by-products on the surface of chicken tissues; chicken skin and fat exposed to a traditional chlorinated chill tank water system (50 ppm FAC). Results from these assessments concluded that either no or extremely low levels (<4.5 ppm) of THMs were present on the surface of exposed poultry tissues (Najjar, M. B., & Meng, J. (2009). *Risk Assessment of Disinfection Byproducts in Poultry Chilled in Chlorinated Water*. Joint Institute for Food Safety and Nutrition and Department of Nutrition and Food Science; Vizzier-Thaxton, Y., et al. (2010). Generation and detection of trihalomethanes in chicken tissue from chlorinated chill water. *The Journal of Applied Poultry Research*, 19(2), 169-173). Poultry chiller water maintained at 50 ppm chlorine accounts for 0.3-1% of human THM exposure, thus not signifying a significant risk for cancer or other health conditions from consuming poultry products (Najjar, M. B., & Meng, J. (2009). *Risk Assessment of Disinfection Byproducts in Poultry Chilled in Chlorinated Water*. Joint Institute for Food Safety and Nutrition and Department of Nutrition and Food Science).

The meat in this novel ground beef manufacturing system is only exposed to a maximum level of 5 ppm FAC for a matter of minutes. Despite the level of THMs in the water, there should not be a health hazard from consuming the lean beef recovered in the final product.

TABLE 6

Trichloromethane Analysis of Recirculating Water during Optimized Validation Study.

| Day | Time | Location | mg/L |
| --- | --- | --- | --- |
| 1 | Before Study | Vortex | 0.1-0.3* |
| 1 | Before Study | Flotation tank | 0.293 |
| 1 | After Preliminary Water Study | Vortex | 0.211 |
| 1 | After Preliminary Water Study | Flotation tank | 0.1-0.3* |
| 1 | After Production | Vortex | 0.1-0.3* |
| 1 | After Production | Flotation tank | 0.188 |
| 2 | Before Production | Vortex | 0.1-0.3* |
| 2 | Before Production | Flotation tank | 0.1-0.3* |
| 2 | After Production | Vortex | 0.24 |
| 2 | After Production | Flotation tank | 0.221 |
| 2 | After Sanitation | Vortex | 0.176 |
| 2 | After Sanitation | Flotation tank | 0.201 |
| 3 | Before Production | Vortex | 0.109 |
| 3 | Before Production | Flotation tank | 0.091 |
| 6 | After Production | Vortex | 0.226 |
| 6 | After Production | Flotation tank | 0.198 |
| 6 | After Sanitation | Vortex | 0.205 |

*Samples higher than the standard curve levels and thus can only be estimated between 100-300 ppb.

Pre-Operation and Environmental Samples

Pre-Operation samples targeting rif-resistant surrogates were taken daily, starting on the third day of the production run when the research team learned the plant operations staff had not been cleaning equipment daily between each day. Due to a lack of cleaning the dewatering centrifuge and bond breaker were opened and noticeable build-up was present.

Although major pieces of equipment, including the grinder belt, dewatering centrifuge lid and drop chute, and the bond breaker, were cleaned daily, low levels of contamination were still present at the bond breaker which continued to contaminate non-inoculated meat entering the system at the beginning of every day as indicated by pre-inoculated vortex and manifold meat samples (Table 7, Table 8).

TABLE 7

Preliminary Study Pre-Operation Equipment Samples.
ECC Log CFU/cm$^2$

| | | Day | | | |
|---|---|---|---|---|---|
| | | 3* | 4 | 5 | 6 |
| Sampling Location | Grinder Conveyor Belt | 0.002 | 0.0 | 0.0 | 0.0 |
| | Centrifuge Drop Chute | 0.002 | 0.0 | 0.0 | 0.0 |
| | Bond Breaker | 1.8 | 0.10 | 0.009 | 0.011 |
| | Centrifuge Lid | — | 0.0 | — | — |
| | Manifold Sample Pipe | 0.0 | 0.0 | — | — |
| | Crytotunnel Conveyor Belt | 0.015 | — | — | — |
| | FFT sample pipe | 0.0 | — | — | — |
| | Centrifuge conveyor belt | 0.001 | — | — | — |

*Daily cleaning of equipment began after Day 3.

The build-up within the centrifuge was highly contaminated (Table 8), thus acting as a secondary inoculating point during processing if not thoroughly cleaned at least daily. Aside from the build-up within the centrifuge lid, the high levels of contamination present on non-inoculated meat exiting the centrifuge as a final product 24 hours following introduction of inoculated meat into the system indicates that 1) the inner-workings of the centrifuge are not being effectively disinfected by the 5 ppm FAC recirculating solution overnight (~20 hours), and 2) the centrifuge currently in place is not cleanable within the anticipated 4-hour sanitation period and may need to be replace with more cleanable equipment.

TABLE 8

Preliminary Study Indicators of Equipment Cleanliness.
Meat Samples (ECC Log CFU/g)

| | | Day | | | |
|---|---|---|---|---|---|
| | | 3* | 4 | 5 | 6 |
| Sampling Location | Centrifuge Lid build-up | 3.0 | 4.2 | — | — |
| | Particle Filter build-up | 0.0 | 0.0 | — | — |
| | Pre-Inoculated Meat at Vortex | 0.0 | 0.0 | 0.0 | 2.2 |
| | Pre-Inoculated Meat at Manifold | 1.0 | 0.0 | 2.4 | 0.7 |
| | Pre-Inoculated Meat at Centrifuge | 1.9 | 3.1 | 1.8 | 2.2 |

*Daily cleaning of equipment began after Day 3.

TABLE 9

Preliminary Study Environmental Samples.

| Sampling Point | ECC Log CFU/cm2 |
|---|---|
| Edible bin | 0.0 |
| Technician sleeves | 0.0 |
| Operator gloves | 0.0 |
| Doorknob | 0.0 |
| Manifold sampling knob | 0.0 |
| Pipet used to filter water samples | 0.0 |

Production and laboratory environment was evaluated for rif-resistant surrogate contamination on the fifth production day. No level of surrogates was found in any of the samples collected. The results from these pre-operation equipment and indicator meat samples prompted the implementation of better equipment cleaning and water sanitation practices during the optimized study, as described above.

Pre-Operation samples targeting both rif-resistant and total aerobic bacteria were collected daily during the optimized validation study. Starting on the fourth day of production, equipment samples were taken at the end of each following cleaning in preparation for the following day's production. No surrogates were recovered on the equipment and very low levels of aerobic bacteria were recovered (Table 10) indicating much improved sanitation practices compared to the preliminary study. This directly correlates to essentially no surrogates recovered in non-inoculated meat samples prior to introduction of inoculum (Table 11) thus indicating the necessity of proper equipment and recirculating red water sanitation. Unlike, the preliminary study, inoculated meat was introduced every other day, thus pre-inoculum non-inoculated samples were taken every other day. On the fifth production day, it was noticed that fat was building up within the water exit ports of the centrifuge; the build-up was collected and enumerated revealing 2.6 Log CFU/g rif-resistant surrogates if not addressed (Table 10).

TABLE 10

Optimized Study Pre-Operation Equipment Samples.
Log CFU/cm$^2$

| | | Day | | | | | | End of 6-Day Run |
|---|---|---|---|---|---|---|---|---|
| | | 1 | 2 | 3 | 4* | 5 | 6 | |
| | | ECC | | | | | | |
| Sampling Location | Grinder Conveyor Belt | | 0.0 | 0.0 | 0.0 | 0.0 | 0.0 | 0.0 |
| | Bond Breaker | 0.0 | 0.0 | 0.0 | 0.0 | 0.0 | 0.0 | 0.0 |
| | Centrifuge drop Chute | 0.0 | 0.0 | 0.0 | 0.0 | 0.0 | 0.0 | 0.0 |
| | Centrifuge Lid | — | 0.0 | 0.0 | 0.0 | 0.0 | 0.0 | 0.0 |
| | Grinder Belt Conveyor 'fins' | 0.0 | — | 0.0 | 0.0 | 0.0 | 0.0 | 0.0 |
| | | APC | | | | | | |
| Sampling Location | Grinder Conveyor Belt | 0.0005 | 0.0 | 0.0007 | 0.0004 | 0.0 | — | — |
| | Bond Breaker | 0.0 | 0.0 | 0.0 | 0.0196 | 0.0124 | 0.0 | 0.0 |

TABLE 10-continued

Optimized Study Pre-Operation Equipment Samples.
Log CFU/cm$^2$

| | Day | | | | | | |
|---|---|---|---|---|---|---|---|
| | 1 | 2 | 3 | 4* | 5 | 6 | End of 6-Day Run |
| Centrifuge drop Chute | 0.0 | 1.37 | 0.0034 | 0.0038 | 0.0022 | 0.0023 | 0.0043 |
| Centrifuge Lid | — | 0.0 | 0.0017 | 0.0018 | 0.0 | 0.0 | 0.0 |
| Grinder Belt | — | — | — | — | — | — | — |
| Conveyor 'fins' | 2.54 | — | — | — | — | — | — |

*Collecting samples in evening after sanitation instead of morning before production.

The centrifuge exit ports were immediately cleaned in preparation for the last production day. A sample was taken from the same port following the last day of production and no surrogates were recovered; this could indicate that the 2.6 Log CFU/g recovered the previously day was partially due to 5-days build-up over the course of the study. It is possible that this could be indicative of a day's worth of surrogate build-up that would be reduced during the 50 ppm chlorine boost that recirculates through the centrifuge.

TABLE 11

Optimized Study Indicators of Equipment Cleanliness
Meat Samples (Log CFU/g)

| | | Day | | | | | |
|---|---|---|---|---|---|---|---|
| | | 1 | 2 | 3 | 4 | 5 | 6 |
| | | EC | | | | | |
| Sampling | Centrifuge build-up | — | — | — | — | 2.6 | 0.0 |
| | Pre-Inoculated Meat at Vortex | 0.0 | — | 0.0 | — | 0.0 | — |
| | Pre-Inoculated Meat at Manifold | 0.0 | — | 0.0 | — | 0.0 | — |
| | Pre-Inoculated Meat at Centrifuge | 0.0 | — | 0.0 | — | 0.0 | — |
| | | AP | | | | | |
| Sampling | Centrifuge build-up | — | — | — | — | 5.7 | 3.7 |
| | Pre-Inocualted Meat at Vortex | 5.8 | — | 6.7 | — | 4.6 | — |
| | Pre-Inocualted Meat at Manifold | 5.3 | — | 6.5 | — | 4.4 | — |
| | Pre-Inoculated Meat at Centrifuge | 5.0 | — | 6.1 | — | 4.3 | — |

Environmental samples (Table 12) were collected every other day, with the exception of a positive control sample taken on Day 5 of gloves used to inoculate beef trim for Day 6 inoculation. Rif-resistant surrogates were only recovered in one floor sample, indicating that relatively little environmental contamination occurred throughout the study. APC counts across samples were extremely low indicating good manufacturing practices and cleanliness was maintained throughout the production floor and the laboratory areas.

TABLE 12

Optimized Study Environmental Samples
(Log CFU/cm$^2$)

| | Sampling Point | ECC | APC |
|---|---|---|---|
| Day 2 | Doorknob | 0.0 | 0.0 |
| | Vortex Port Handle | 0.0 | 0.1 |
| | Edible Bin | 0.0 | 0.0 |

TABLE 12-continued

Optimized Study Environmental Samples
(Log CFU/cm$^2$)

| | Sampling Point | ECC | APC |
|---|---|---|---|
| Day 4 | Fat drop chute | 0.0 | 0.00068 |
| | Grinder Drop Chute | 0.0 | 0.0016 |
| | Flotation Tank Port Handle | 0.0 | 0.0 |
| | Lab Stomacher | 0.0 | 0.0 |
| | Lab Pipetter | 0.0 | 0.0 |
| Day 5 | Inoculated Glove (Positive Control) | 4.98 | 5.25 |
| Day 6 | Lab Benchtop | 0.0 | 0.0 |
| | Technician jacket sleeves | 0.0 | 0.022 |
| | Drain | 0.0 | 0.023 |
| | Worker Boots | 0.0 | 0.076 |
| | Plastic buchner funnel post-sanitation | 0.0 | 0.091 |
| | Blue Tote, holds Ziplock Water Samples | 0.0 | 0.022 |
| | Red Squeegie | 0.0 | 0.0 |
| | Floor by Centrifuge | 0.0065 | 0.23 |
| | Worker Glove | 0.0 | 1.11 |

Meat Samples

Inoculated Meat—There are two points where pathogens can be reduced in the system: 1) During the cryofreeze as shown from the inoculated meat to the vortex and 2) From exposure to the chlorine in the recirculating water as shown at the post-surge tank, final lean, fat tank, and final fat.

Figure 20:
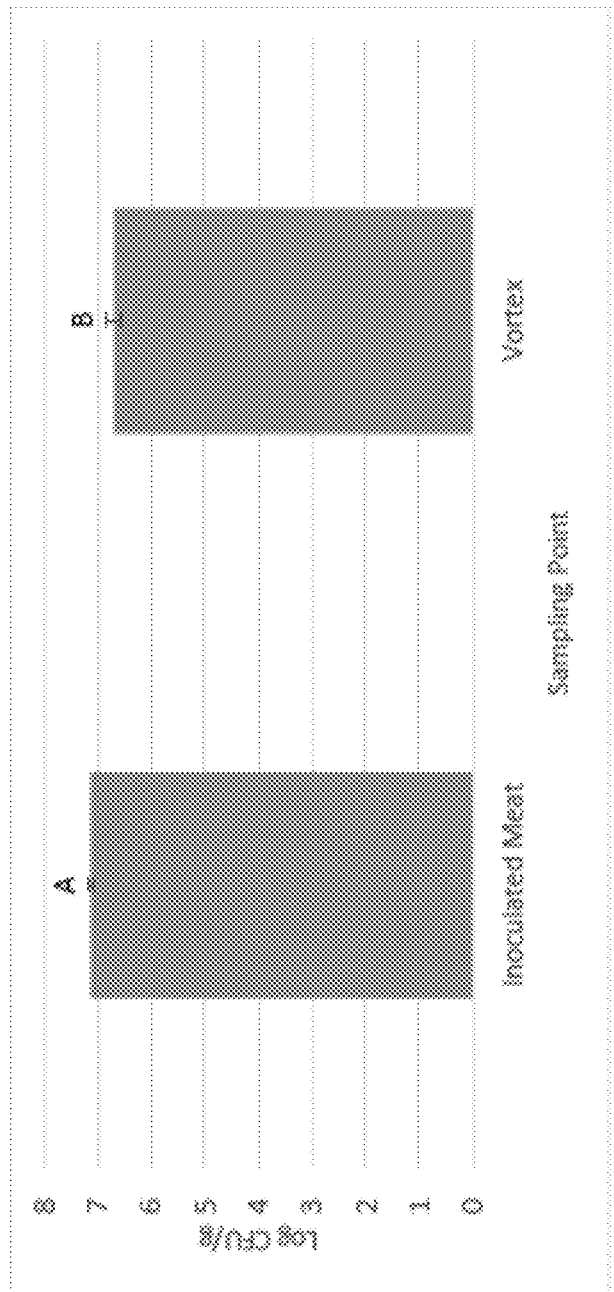
FIG. 20 shows Recovery of Surrogates (ECC) Before and After the Cryofreeze Tunnel; A-B different letters indicate significant differences ($P \le 0.01$).

Parameters from the preliminary study to the optimized study did not change between the introduction of inoculated meat to the vortex, therefore we can accurately describe a reduction in surrogate organisms due to freezing from 18 total observations. Due to the nature of sampling and limited effect of freezing on E. coli and surrogate organisms, variation is expected to be higher in vortex samples thus requiring the use of Fisher's Protected LSD for statistical analysis. Freezing alone results in a significant 0.4 log CFU/g reduction ($P \leq 0.05$) as described in FIG. 20.

Figure 21:
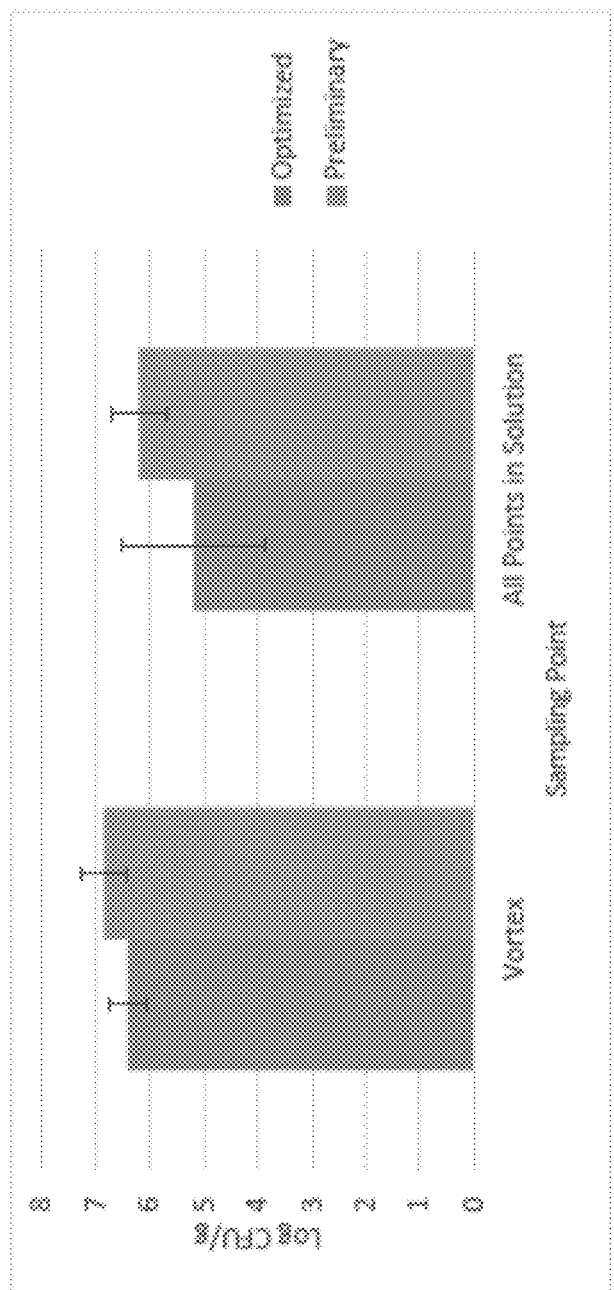
FIG. 21 shows Recovery of Surrogates (ECC) Averaged Across All Sampling Points in Contact with Chlorinated Nanobubble Process Water.
Figure 22:
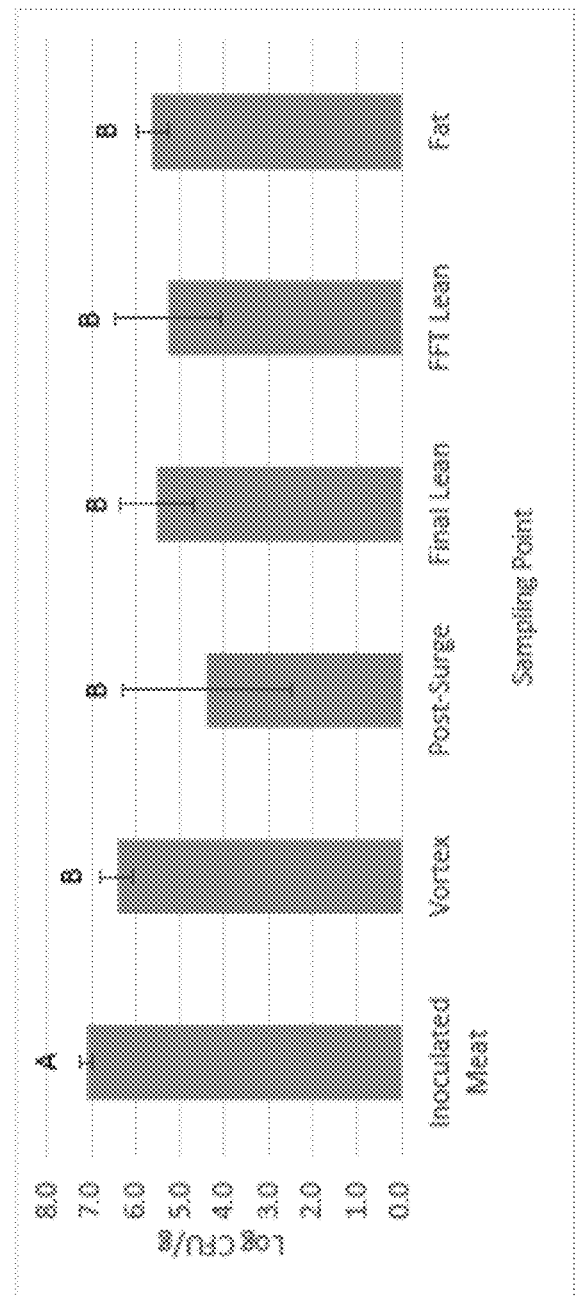
FIG. 22 shows Average Recovery of Surrogates (ECC) on Inoculated Meat at Different Sampling Points Throughout the System, A-B different letters indicate significant differences ($P \le 0.05$).
Figure 23:
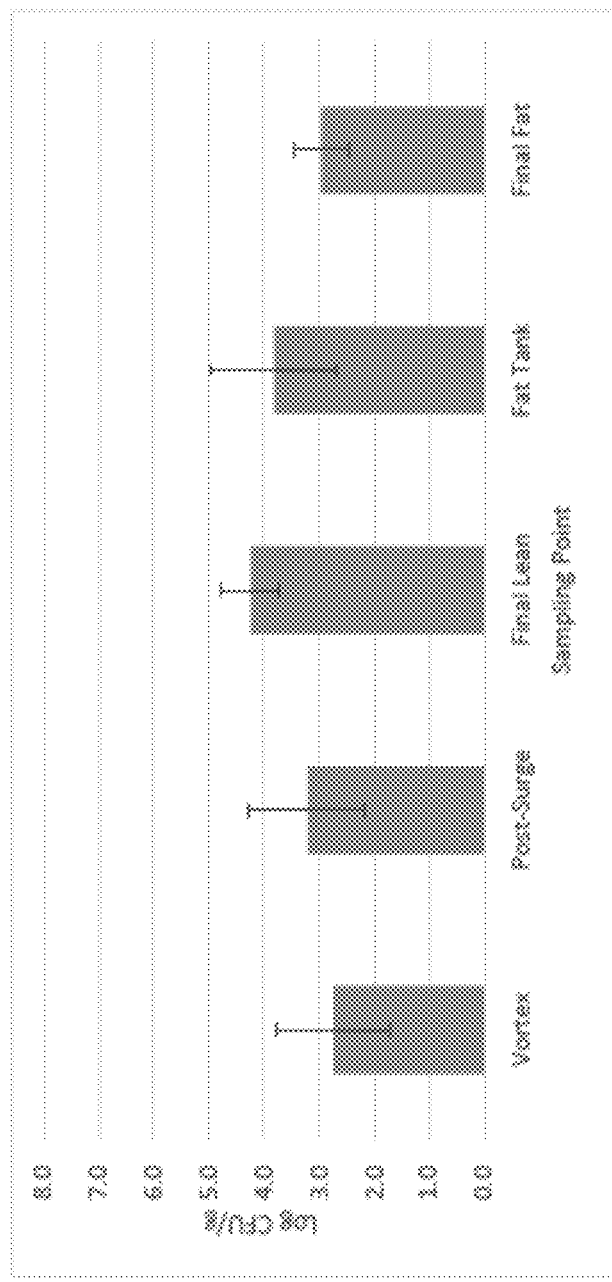
FIG. 23 shows Average Recovery of Surrogates (ECC) on Same-Day Pick-Up Meat at Different Sampling Points Throughout the System, A-B different letters indicate significant differences ($P \le 0.05$).
Figure 24:
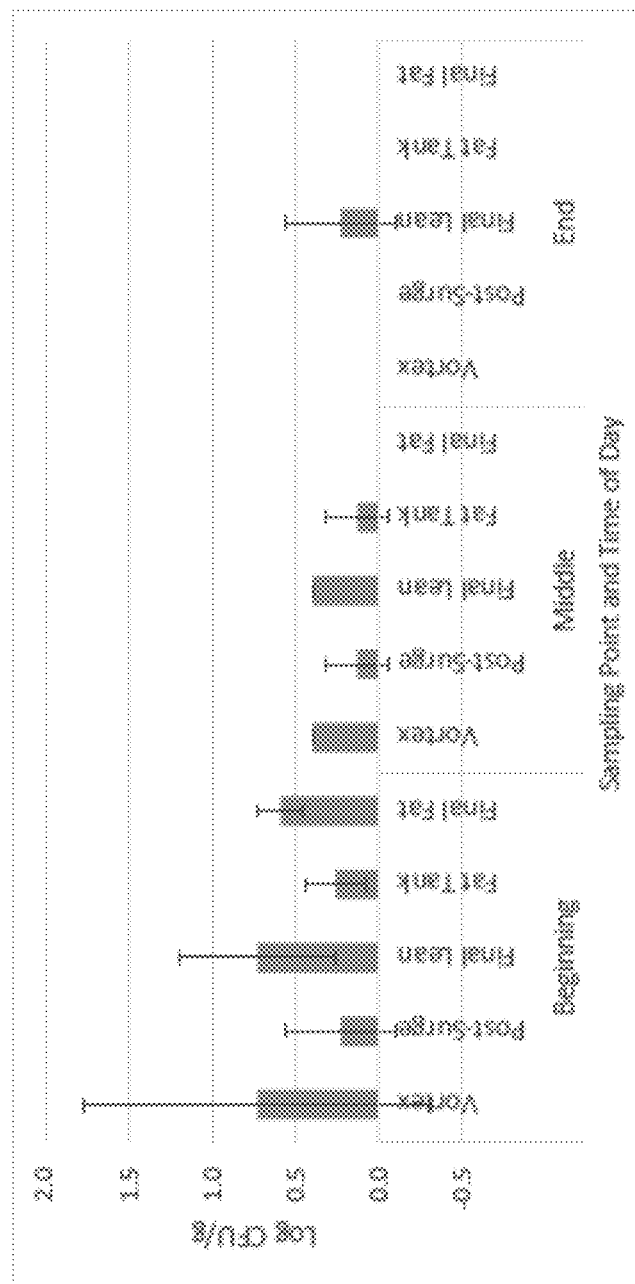
FIG. 24 shows Average Recovery of Surrogates (ECC) on 24-hour Pick-Up Meat at Different Sampling Points Throughout the System at the Beginning, Middle, and End of the production Day.

During the optimized study, an average 1.2 Log CFU/g reduction of surrogates from the vortex to all points exposed to chlorine solution (i.e. the combination of the Post-Surge Tank, Final Lean, FFT lean/Fat Tank, and Final Fat) was observed. This totals to an average 1.6 Log CFU/g reduction of surrogates on the inoculated meat across the system whereas, an average total 1.0 Log CFU/g reduction of surrogates on inoculated meat samples across the system was observed in the preliminary study. Statistical analysis of the optimized study revealed that, while we had significant kill, there was no difference between the individual sampling points (P>0.05) as described in FIG. 21.

Same-day Pick-up Meat—Similar to the preliminary study, approximately 2.7 Log CFU/g of the *E. coli* surrogates were picked up on non-inoculated meat between the grinder conveyor belt and the bond breaker and introduced into the recirculating antimicrobial solution during the optimized study. From the vortex to the final lean product, an additional 1.5 Log CFU/g is picked up, most likely from harborage of organisms in the centrifuge. While >2.9 Log CFU/g was collected on the non-inoculated meat, relatively little contamination is acquired from the recirculating solution, however, contamination picked-up is not necessarily reduced by the average 3.3 ppm FAC chlorine in solution before the final lean or final fat products.

This indicates that any level of contamination, especially a high level, may be carried over into previously 'clean' meat and the recirculating solution due to dirty equipment. There are is no significant difference across sampling points (P>0.05); however, the same-day pick-up samples are significantly lower than the inoculated meat samples (P≤0.05).

24 hour Pick-up Meat—During the optimized study, meat was inoculated every other day. The results from the 24-hr pick up meat indicate that there is a small level of surrogate contamination carrying over onto non-inoculated meat, which is mostly likely from bacteria harbored on equipment before the vortex (i.e. grinder conveyor belt, cryofreeze tunnel, and/or bond breaker) and in the centrifuge. The presence of surrogates in meat samples could also be due to biofilm build-up within the manifold, fluid transport pipes, or flotation tank; although, these areas are not accessible except during full system breakdown and were not sampled. However, much of this contamination was found by enrichment and indicates that surrogates were present in levels less than the detectable limit of 0.4 Log CFU/g. As few as 1 cell would cause a positive enrichment but, this is important because only one STEC or *Salmonella* cell can cause illness in high risk human populations. It should be noted that any contamination present at or before the vortex clears out of the system over the course of a 4-hour production day however (Table 11), contamination in still present in the centrifuge. No significant differences were found (P>0.05) between time of day (beginning, middle, or end) in 24-hour pick-up samples.

A significant interaction (P≤0.05) was observed between treatment and sampling point. There are also slightly significant (P≤0.05) sample and treatment effects. Most notably, the significant differences between combined inoculated meat samples and same-day pick-up meat samples (P≤0.05), and same-day pick-up samples and 24-hour pick-up (P≤0.05) samples show a strong decreasing trend in recovery of organisms over time. These results support the use of the chlorinated nanobubble recirculating solution as an antimicrobial in this system and the implementation of equipment cleaning (albeit this still needs to be addressed due to the positive samples) and the 50 ppm FAC boost to the system for 30 minutes during the sanitation period.

It is often recommended that surrogate organisms marked with antimicrobial resistance genes, such as the surrogates used in this study, should be avoided and are unnecessary due to the unnaturally high level of controlled inoculum that is added in validation studies (USDA Food Safety and Inspection Service. (2015). *Sampling verification activities for shiga toxin-producing Escherichia coli (STEC) in raw beef products* (No. FSIS Directive 10,010.1 Rev. 4). Washington D.C.); however, in this study, the Aerobic Plate Counts (APC) were higher than in a standard meat processing environment due to the age of the meat obtained and length of storage. In addition, no statistical difference was observed between sampling groups (Inoculated Meat, Same-Day Pick-Up Meat, and 24-hour Pick-Up Meat) and the APC were not reduced significantly (p>0.05) by freezing or by exposure to chlorine in the recirculating water and, therefore, are not a good indicator of process efficiency at any point in this system. Had non-rif-resistant organisms been used, the lethality contributions of the system would not have been accurately characterized.

Conclusion

Zhou and colleagues described chlorine as having a limited capacity to inactivate pathogens on the surface of products but extremely effective at controlling pathogen levels in wash water (Zhou, B., et al. (2015). Inactivation dynamics of *Salmonella enterica, Listeria monocytogenes*, and *Escherichia coli* O157:H7 in wash water during simulated chlorine depletion and replenishment processes. *Food Microbiology*, 50, 88-96). Most commercially available chlorine based sanitizers only reduce pathogens on the surface of produce by 1-2 log cycles (Yang, Y., et al. (2012). Enhanced Chlorine Efficacy against Bacterial Pathogens in Wash Solution with High Organic Loads: Enhanced Chlorine Efficacy against Pathogens. *Journal of Food Processing and Preservation*, 36(6), 560-566). This phenomenon was evident in the results from the water and meat samples in this study.

Relative to the novel ground beef commercial manufacturing system evaluated in this research, the optimized system that utilized chlorinated Cesco-NAN-02 technology nanobubble water showed excellent potential for success in reducing contamination present in beef trim in a 6-day continuous run processing scenario. The combined reduction from freezing (average of 0.4 log CFU/g) and chlorine exposure (average of 1.2 log CFU/g) on inoculated meat provides a total process reduction of 1.6 log CFU/g of final ground beef. The implementation of nightly manual equipment cleaning and a 50 ppm chlorine spike reduced levels of target organisms >6 log CFU/g picked up on meat 24-hours after inoculated meat entered the system. No surrogate organisms were recovered in Cesco-NAN-02 technology process water samples indicating the sanitizing properties of the water. However, surrogates were recovered on Whatman filter enrichments indicating the organisms were attaching to small organic particles within the recirculating water. Thus, during meat processing operations, low levels of viable surrogates were present in recirculating water, but the 4-hour elevated chlorine period at the end of each production day eliminated this contamination, thereby managing the risk of contamination carrying over into the next production day.

The cleaning protocols utilized during the optimized study should be included, strictly outlined in Sanitation Standard Operating Procedures (SSOPs), and implemented daily during production, paying special attention to the centrifuge and all pieces of equipment before the vortex (i.e. bond breaker, grinder conveyor belt, grinder, open areas of the cryofreeze belt). The nightly 50 ppm chlorine boost provides a thorough disinfection of the recirculating red water and must be implemented to establish a break in the multi-day continuous run process (i.e., defining each day's meat production as a manufacturing lot). Precautions should be taken to ensure employee safety and compliance with OSHA regulations during the chlorine boost period.

Example 3

Salmon Roe (Ikura) Processing

Salmon roe (or Ikura as it is called in Japan) was washed in a processing plant with Cesco-NAN-02 technology water with 1-2 ppm active Aquaox AX-5000 (HOCl).

Results

Samples of processed (Cesco-NAN-02-Aquaox) and unprocessed ('Green") Ikura were submitted to Edge analytical for Total Aerobic Plate Counts (AOAC990.12 Petrifilm), *E. coli* (AOAC991.14 Petrifilm) and Total Coliform (AOAC991.14 Petrifilm) testing (Tests 1-4 attached). Test 4 (Green Ikura) had a Total Aerobic Plate Count mean average of 852 CFU/g, which exceeds the measurable range of 30-300 colonies for AOAC990.12. *E. coli* measured in all ten (10) samples at <10 CFU/g, which is below the measurable range of AOAC991.14 (15-150 colonies). However, six of the ten samples tested positive for Total Coliforms, having a mean average of 30, which falls well within the measurable range of this test.

Results for the Cesco-NAN-02-Aquaox processed Ikura were very good for Tests 1-3. Test 1 measured 10 ppm free chlorine during the Egg Wash stage and 2.0 ppm for the process water (at Broken Shell stage). Five (5) samples were analyzed. Total Aerobic Plate Counts on four (4) of the samples measured at <10 CFU/g, which is below the range of AOAC990.12. There was one sample that measured 70 CFU/g, however this data point must be an outlier (contaminated test) when one considers that there were twenty-five (25) Cesco-NAN-02-Aquaox samples submitted for Tests 1-3 and it is the lone sample that tested positive within the range of AOAC990.12. Test 1 counts for *E. coli* and Total Coliform all measured at <10 CFU/g, which is below the measurable range of AOAC991.14.

Test 2 measured 18 ppm free chlorine during the Egg Wash stage and 1.6 and 1.2 ppm for the process water (at Broken Shell and Brine Agitator stages respectively). Ten (10) samples were analyzed. Total Aerobic Plate Counts on all samples measured below the range of AOAC990.12. However, there was one lone sample of this set that measured at 20 CFU/g (still below the test range), but we are still noting it in this report. Test 2 counts for *E. coli* and Total Coliform all measured at <10 CFU/g, which is below the measurable range of AOAC991.14.

Test 3 measured 1.8 ppm free chlorine during the Egg Wash stage and 1.6 and 1.4 ppm for the process water (at Broken Shell and Brine Agitator stages respectively). Ten (10) samples were analyzed. Total Aerobic Plate Counts on eight (8) samples measured <10 CFU/g and two (2) measured at 10 CFU/g (below the range of AOAC990.12). Test 3 counts for *E. coli* and Total Coliform all measured at <10 CFU/g, which is below the measurable range of AOAC991.14.

Conclusions

Results indicate that the Cesco-NAN-02-Aquaox technologies provide improved food safety, while reducing the use of hazardous chemicals and operational costs. Based on Test 3, any seafood plant running their process water by injecting AX-5000 (HOCl) into the Cesco-NAN-02 technology can expect to generate an ORP of nearly 800 mV with a chlorine residual of only 1.6-1.8 ppm. Based on this study, we are recommending 2 ppm chlorine residual for all seafood plants that utilize Cesco-NAN-02-Aquaox for their process water. The potential reduction in chemicals and improvements for processing plant personnel and consumer safety are substantial for all seafood products. For example, instead of using hazardous chemicals such as Sodium Hypochlorite or Chlorine Dioxide (ClO2), processing plants can now consider utilizing a much safer approach that uses Cesco-NAN-02 technology and Aquaox AX-5000 to produce high ORP water with incredibly low amounts of chemistry as compared to standard protocol.

Based on the Ikura Test 3, Cesco-NAN-02-Aquaox can generate 800 ORP at 2.0 ppm chlorine residual. This represents a 98% reduction in chlorine at the Egg Wash stage and 80% chlorine reduction in the process water. We expect similar results for other seafood products (i.e. smoked salmon and other processed fish designated for consumers). Additionally, there will be further cost reductions in cleaning and sanitizing chemicals for plants that utilize this program.

Example 4

Water Purification

Various water samples were tested for particle concentration and size as follows:

Sample 1—City water, 8.9 pH, 1.0 ppm FAC

Sample 2—Cesco-NAN-02 technology water, 7.4 pH, 0.5 ppm FAC (no carbon dioxide gas or hypochlorous acid added)

Sample 3—Cesco-NAN-02 technology water, 5.0 pH, 0.5 ppm FAC (carbon dioxide gas added to drive down pH but no hypochlorous acid added)

Sample 4—City water, 9.0 pH, 31 ppm FAC

Sample 5—Cesco-NAN-02 technology water, 7.2 pH, 32 ppm FAC (no carbon dioxide gas added, hypochlorous acid added)

Sample 6—Cesco-NAN-02 technology water, 5.4 pH, 31 ppm FAC (carbon dioxide gas and hypochlorous acid added)

A Nanosight Model NS300 instrument was used to measure size and particle concentration in the water samples. Samples were stored at room temperature and shaken gently before loading into instrument, no dilution. Three movies of 30 seconds each were recorded for each sample. Samples were measured in flow mode, using a syringe pump at flow setting 15. 2 mL of Mili-Q water were flushed between samples.

Results

Mili-Q water was included for comparison. As shown in Table 13, mean particle size of all samples was between 118-202 nm.

TABLE 13

Mean particle size and concentration in treated and untreated water samples

| Sample | Mean Size (nm) | Particle Concentration (particles/mL) |
| --- | --- | --- |
| 1 | 118 | 6.29E+07 |
| 2 | 119 | 4.30E+07 |
| 3 | 202 | 6.20E+07 |
| 4 | 145 | 7.40E+07 |
| 5 | 121 | 3.30E+07 |
| 6 | 128 | 8.60E+06 |
| Mili Q Water | 161 | 1.70E+07 |

Figure 25:
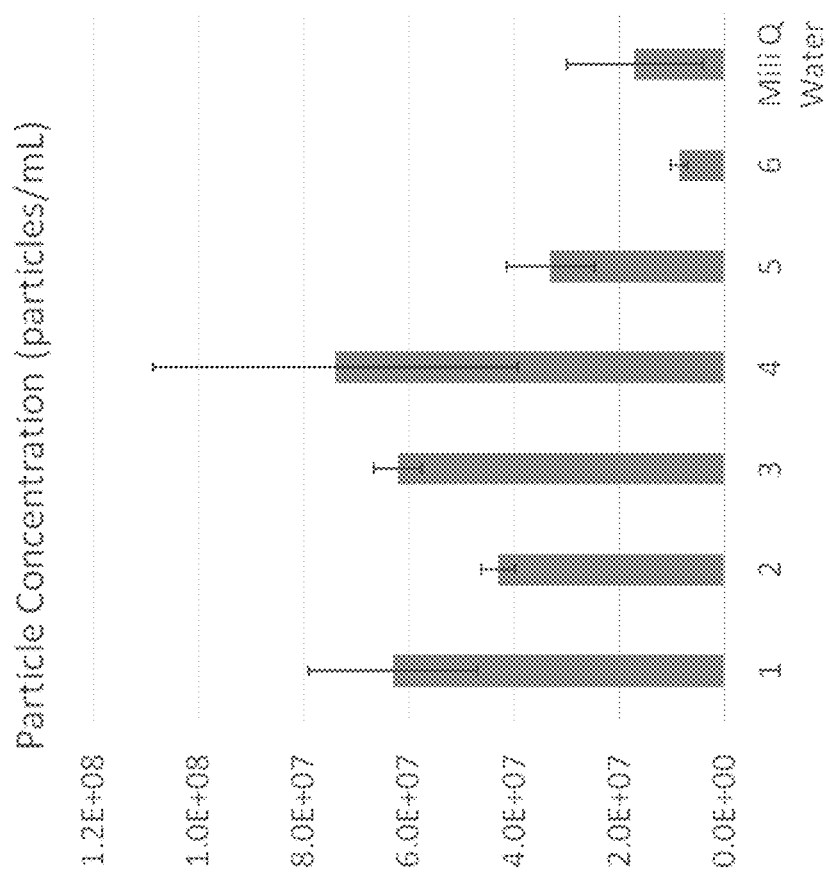
FIG. 25 shows Particle Concentration in various treated and untreated water samples as comparted to Mili-Q water.

All samples were polydisperse from ~50-250 nm. All sample particle concentrations ranged from E+06 to E+07 particles/mL. Except for sample 6, all particle concentrations were higher than Mili-Q water (see Table 13 and FIG. 25).

What is claimed is:

1. A method of treating a food product to reduce microbial content, comprising:
    contacting a food product with a chlorinated nanobubble solution, wherein the chlorinated nanobubble solution comprises electrolyzed water, and wherein the microbial content of the food product is reduced by at least about 0.3 log CFU/g; and recirculating the chlorinated nanobubble solution for continual introduction to food product; wherein recirculating includes, on an as needed basis, introducing carbon dioxide gas into the recirculating chlorinated nanobubble solution to maintain a pre-selected acidic pH; continuously chlorinating the recirculating chlorinated nanobubble solution to maintain a preselected ppm of free available chlorine (FAC); filtering the recirculating chlorinated nanobubble solution; and passing the recirculating chlorinate nanobubble solution through a nanobubble generator to maintain a preselected concentration FAC and nanobubbles;

wherein chlorinating the recirculating nanobubble solution occurs after filtering and before passing the recirculating chlorinated nanobubble solution through a nanobubble generator.

2. The method of claim 1, wherein the electrolyzed water has an enhanced concentration of low zeta potential crystal and is generated by passing source water through a low zeta potential crystal generator and changing the crystalline structure of minerals in the source water.

3. The method of claim 1, wherein the chlorinated nanobubble solution comprises nanobubbles having a diameter of less than 200 nm.

4. The method of claim 1, wherein the chlorinated nanobubble solution comprises free available chlorine in an amount of less than or equal to 300 ppm.

5. The method of claim 1, wherein the chlorinated nanobubble solution comprises free available chlorine in an amount of between 0.5 ppm and 50 ppm.

6. The method of claim 1, wherein the chlorinated nanobubble solution has a pH of at least 5 and less than 7.

7. The method of claim 1, wherein the food product is selected from the group consisting of meat, vegetables, fruit, and eggs in their shell.

8. The method of claim 7, wherein the meat is selected from the group consisting of beef, poultry, and pork and the preselected pH is in a range of 5 to 5.5.

9. The method of claim 1, wherein the recirculating chlorinated nanobubble solution is cooled to a preselected temperature.

10. The method of claim 1, wherein filtering the recirculating chlorinated nanobubble solution removes particles from the food product carried by the recirculating chlorinated nanobubble solution.

11. The method of claim 8, wherein the preselected ppm for available chlorine is 5 ppm.

* * * * *